US010537109B2

(12) United States Patent
Bramlett et al.

(10) Patent No.: US 10,537,109 B2
(45) Date of Patent: Jan. 21, 2020

(54) COMPOSITIONS AND METHODS FOR CONTROLLING PLANT PESTS

(71) Applicants: SYNGENTA PARTICIPATIONS AG, Basel (CH); SYNGENTA CROP PROTECTION LLC, Greensboro, NC (US)

(72) Inventors: Matthew Richard Bramlett, Zwijnaarde Ghent (BE); Katherine Seguin, Research Triangle Park, NC (US); Vance Cary Kramer, Research Triangle Park, NC (US); Mark Scott Rose, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/534,199

(22) PCT Filed: Dec. 3, 2015

(86) PCT No.: PCT/US2015/063620
§ 371 (c)(1),
(2) Date: Jun. 8, 2017

(87) PCT Pub. No.: WO2016/094165
PCT Pub. Date: Jun. 16, 2016

(65) Prior Publication Data
US 2017/0339964 A1 Nov. 30, 2017

Related U.S. Application Data

(60) Provisional application No. 62/090,900, filed on Dec. 12, 2014.

(51) Int. Cl.
*C07K 14/325* (2006.01)
*A01N 63/00* (2006.01)
*C12N 15/82* (2006.01)
*A01N 63/02* (2006.01)

(52) U.S. Cl.
CPC ............ *A01N 63/02* (2013.01); *A01N 63/00* (2013.01); *C07K 14/325* (2013.01); *C12N 15/8286* (2013.01); *Y02A 40/162* (2018.01)

(58) Field of Classification Search
None
See application file for complete search history.

(56) References Cited

U.S. PATENT DOCUMENTS

| 3,993,756 | A | * | 11/1976 | Kaneda | ................. | A61K 36/48 424/757 |
| 7,629,504 | B2 | * | 12/2009 | Flannagan | ............. | A01N 63/02 800/302 |
| 2005/0138685 | A1 | | 6/2005 | Flannagan et al. | | |
| 2013/0055469 | A1 | | 2/2013 | Sampson et al. | | |

FOREIGN PATENT DOCUMENTS

CA 2860864 A1 7/2013

OTHER PUBLICATIONS

Guo et al, 2004, Proc. Natl. Acad. Sci. USA 101: 9205-9210.*
De Maagd et al, 1999, Appl. Environ. Microbiol. 65:4369-4374.*
Aaronson et al, 2001, FEMS Microbiol. Lett. 195:1-8.*
De Maagd et al, 2001, Trends Genet. 17:193-199.*
Su, H et al., "Bacillus Thuringiensis Strain T03C001 cry9Aa-like Protein Gene", Complete Cds., National Center for Biotechnology Information, Genbank entry, Dec. 31, 2012, Retrieved Mar. 15, 2016, Retrieved from the internet URL:http://www>ncbi.nlm.nih.gov/nuccore/gq249294.1.
International search report cited in International Application No. PCT/US15/63620 filed Dec. 3, 2015, dated Apr. 27, 2016.

* cited by examiner

*Primary Examiner* — Anne Kubelik
(74) *Attorney, Agent, or Firm* — Gregory W. Warren

(57) ABSTRACT

Novel insecticidal proteins isolated from *Bacillus thuringiensis* that are active against lepidopteran insect pests are disclosed. The DNA encoding the insecticidal proteins can be used to transform various prokaryotic and eukaryotic organisms to express the insecticidal proteins. These recombinant organisms can be used to control lepidopteran insects in various environments.

17 Claims, No Drawings

Specification includes a Sequence Listing.

SEQUENCE LISTING

```
<160> NUMBER OF SEQ ID NOS: 31

<210> SEQ ID NO 1
<211> LENGTH: 3507
<212> TYPE: DNA
<213> ORGANISM: Bacillus thuringiensis
```

<400> SEQUENCE: 1

```
atgaatcgaa ataatcaaaa tgaatatgaa gttattgatg ccccacattg tgggtgtccg        60
gcagatgatg ttgtaaaata tcctttgaca gatgatccga atgctggatt gcaaaatatg       120
aactataagg aatatttaca aacgtatggt ggagactata cagatcctct tattaatcct       180
aacttatctg ttagtggaaa agatgtaata caagttggaa ttaatattgt agggagatta       240
ctaagctttt ttggattccc cttttctagt caatgggtta ctgtatatac ctatcttta       300
aacagcttgt ggccggatga cgagaattct gtatgggacg cttttatgga gagagtagaa       360
gaacttattg atcaaaaaat ctcagaagca gtaaagggta gggcattgga tgacctaact       420
ggattacaat ataattataa tttatatgta gaagcattag atgagtggct gaatagacca       480
aatggcgcaa gggcatcctt agtttctcag cgatttaaca ttttagatag cctatttaca       540
caatttatgc caagctttgg ctctggtcct ggaagtcaaa attatgcaac tatattactt       600
ccagtatatg cacaagcagc aaaccttcat ttgttattat taaaagatgc agacatttat       660
ggagctagat gggggctgaa tcaaactcaa atagatcaat tccattctcg tcaacaaagc       720
cttactcaga cttatacaaa tcattgtgtt actgcgtata atgatggatt agcggaatta       780
agaggcacaa gcgttgcgag ttggctcaaa tatcatcaat accgtaggga atgacagta       840
acggcaatgg atttagtggc attattccca tactataatg ttagacaata tccaaatggg       900
gcaaatccac aacttacacg tgaggtatat acagatccaa tcgtatttaa tccgcctgag       960
cgtccaagtg gcgctttctg cgaaagtttt tatactatcc gagcggctcg agaacgttta      1020
acttttttcgc aacttgaaca tgcaataatt cgtccgccgc gcttgtttga aggtttcaa     1080
gctttaggga tttatacagg cgaggcgcga ctgaatgcaa atagtgctcc aatgaactat      1140
tggattggac attttataag aaatacacgt ttaggtgact caacaacaat tactacaaat      1200
tatgaaacaa ccaataatcg tttaactaac ttcagtatgc cttctgatgt ttatcaaatc      1260
aattcaacct caagtaattt agccgctatt ttaggcactt tatatggggt tactagagca      1320
caattccatt ttggatcagg aagttttttcg acgtatgtcg acaaaatag cgttcttcca      1380
caatgtcatc aaaaactataa ttcaatagaa gaattaccaa accaaagcga tgaacctaca      1440
gttagaagtt atagccatag attatctcat atcacctctt ttaatttcaa tgtacagctt      1500
aataatcctt taatttctgc gggcaatatg cctgtatatg tgtggacaca tcgcagtgtg      1560
gaccttacta acaggatttc ttcagataga attactcaaa taccagtggt aaaggcatat      1620
gagctaagta gtggtgctac tgtcgtgaaa ggtccaggat tcacaggagg agatgtaatc      1680
cgaagaacaa atactggtgg attcggagca ataagggtgt cggtcactgg accgctaaca      1740
caacgatatc gcataaggtt ccgttatgct tcgacaatag attttgattt ctttgtaaca      1800
cgtggaggaa ctactataaa taattttaga tttacacgta caatgaacag gggacaggaa      1860
tcaagatatg aatcctatcg tactgtagag tttacaactc cttttaactt tacacaaagt      1920
caagatataa ttcgaacatc tatccaggga cttagtggaa atggggaagt ataccttgat      1980
agaattgaaa tcatccctgt aaatccaaca cgagaagcgg aagaggattt agaagcggcg      2040
aagaaagcgg tggcgagctt gtttacacgc acaagggacg gattacaagt aaatgtgaaa      2100
gattatcaag tcgatcaagc ggcaaattta gtgtcatgct tatcagatga acaatatggg      2160
tatgacaaaa agatgttatt ggaagcggta cgcgcggcaa aacgcctcag ccgagaacgt      2220
aacttacttc aggacccaga ttttaataca atcaatagta cagaagaaaa tggatggaaa      2280
```

```
gcaagtaacg cgttactat tagtgagggc ggtccattct ataaaggccg tgcacttcag      2340
ctagcaagtg cacgagaaaa ttatccaaca tacatttatc aaaaagtaga tgcatcggag      2400
ttaaaacctt atacacgata tagactagat gggttcgtga agagtagtca agatttagaa      2460
attgatctca ttcaccatca taaagtccat cttgtgaaaa atgtaccaga taatttagta      2520
tctgatactt acccagatga ttcttgtagt ggaatcaatc gatgtcagga acaacagatg      2580
gtaaatgcgc aactggaaac agagcatcat catccgatgg attgctgtga agcagctcaa      2640
acacatgagt tttcttccta tattgataca ggggatttaa attcgactgt agaccaggga      2700
atctggtgta tctttaaagt tcgaacaacc gatggttatg cgacgttagg aaatcttgaa      2760
ttggtagagg tcggaccgtt attgggtgaa cctctagaac gtgaacaaag agaaaatgcg      2820
aaatggaatg cagagttagg aagaaaacgt gcagaaacag atcgcgtgta tcaagatgcc      2880
aaacaatcca tcaatcattt atttgtggat tatcaagatc aacaattaaa tccagaaata      2940
gggatggcag atattatgga cgctcaaaat cttgtcgcat caatttcaga tgtatatagc      3000
gatgccgtac tgcaaatccc tggaattaac tatgagattt acacagagct gtccaatcgc      3060
ttacaacaag catcgtatct gtatacgtct cgaaatgcgg tgcaaaatgg gactttaac      3120 aacgggctag atagctggaa tgcaacagcg ggtgcatcgg tacaacagga tggcaatacg      3180
catttcttag ttctttctca ttgggatgca caagtttctc aacaatttag agtgcagccg      3240
aattgtaaat atgtattacg tgtaacagca gagaaagtag gcggcggaga cggatacgtg      3300
actatccggg atgatgctca tcatacagaa acgcttacat ttaatgcatg tgattatgat      3360
ataaatggca cgtacgtgac tgataatacg tatctaacaa agaagtggt attctattca      3420 catacagatc acatgtgggt agaggtaagt gaaacagaag gtgcatttca tatagatagt      3480
attgaattcg ttgaaacaga aaagtaa                                         3507

<210> SEQ ID NO 2
<211> LENGTH: 3471
<212> TYPE: DNA
<213> ORGANISM: Bacillus thuringiensis

<400> SEQUENCE: 2
atgaatcaaa ataaacacgg aattattggc gcttccaatt gtggttgtgc atctgatgat       60
gttgcgaaat atcctttagc caacaatcca tattcatctg ctttaaattt aaattcttgt      120
caaaatagta gtattctcaa ctggattaac ataataggcg atgcagcaaa agaagcagta      180
tctattggga caaccatagt ctctcttatc acagcacctt ctcttactgg attaatttca      240
atagtatatg accttatagg taaagtacta ggaggtagta gtggacaatc catatcagat      300
ttgtctatat gtgacttatt atctattatt gatttacggg taagtcagag tgtcttaaat      360
gatgggattg cagattttaa tggttctgta ctcttataca ggaactattt agaggctctg      420
gatagctgga ataagaatcc taattctgct tctgctgaag aactccgtac tcgttttaga      480
atcgccgact cagaatttga tagaatttta acccgagggt ctttaacgaa tggtggctcg      540
ttagctagac aaaatgccca atattatta ttaccttctt ttgcgagcgc tgcatttttc      600
catttattac tactaaggga tgctactaga tatggcacta ttgggggct atacaatgct      660 acacctttta taaattatca atcaaaacta gtagagctta ttgaactata tactgattat      720
tgcgtacatt ggtataatcg aggtttcaac gaactaagac aacgaggcac tagtgctaca      780
gcttggttaa aatttcatag atatcgtaga gagatgacat tgatggtatt agatatagta      840
gcatcatttt caagtcttga tattactaat tacccaatag aaacagattt tcagttgagt      900
```

```
agggtcattt atacagatcc aattggtttt gtacatcgta gtagtcttag gggagaaagt      960
tggtttagct ttgttaatag agctaattc tcagatttag aaaatgcaat acctaatcct     1020
agaccgtctt ggttttaaa taatatgatt atatctactg gttcacttac attgccggtt     1080
agcccaagta ctgatagagc gagggtatgg tatggaagtc gagatcgaat ttcccctgct     1140
aattcacaat ttattactga actaatctct ggacaacata cgactgctac acaaactatt     1200
ttagggcgaa atatatttag agtagattct caagcttgta atttaaatga taccacatat     1260
ggagtgaata gggcggtatt ttatcatgat gcgagtgaag ttctcaaag atccgtgtac     1320
gaggggtata ttcgaacaac tgggatagat aaccctagag ttcaaaatat taacacttat     1380
ttacctggag aaaattcaga tatcccaact ccagaagact atactcatat attaagcaca     1440
acaataaatt taacaggagg acttagacaa gtagcatcta atcgccgttc atctttagta     1500
atgtatggtt ggacacataa aagtctggct cgtaacaata ccattaatcc agatagaatt     1560
acacagatac cattgacgaa ggttgatacc cgaggcacag gtgtttctta tgtgaatgat     1620
ccaggattta taggaggagc tctacttcaa aggactgacc atggttcgct ggagtattg     1680
agggtccaat ttccacttca cttaagacaa caatatcgca ttagagtccg ttatgcttct     1740
acaacaaata ttcgattgag tgtgaatggc agtttcggta ctatttctca aaatctccct     1800
agtacaatga gattaggaga ggatttaaga tacggatctt ttgctataag agagtttaat     1860
acttctatta gacccactgc aagtccggac caaattcgat tgacaataga accatctttt     1920
attagacaag aggtctatgt agatagaatt gagttcattc cagttaatcc gacgcgagag     1980
gcgaaagagg atctagaagc agcaaaaaaa gcggtggcga gcttgtttac acgcacaagg     2040
gacggattac aagtaaatgt gaaagattat caagtcgatc aagcggcaaa tttagtgtca     2100
tgcttatcag atgaacaata tgggtatgac aaaaagatgt tattggaagc ggtacgtgcg     2160
gcaaaacgac ttagccgaga acgcaactta cttcaggatc cagattttaa tacaattaat     2220
agtacagaag aaaatggatg gaaagcaagt aacggcgtta ctattagtga gggcgggcca     2280
ttctataaag gccgtgcaat tcagctagca agcgcacgag aaaattatcc aacatacatt     2340
tatcaaaaag tagatgcatc ggagttaaag ccatatacac gctatagact ggatggattc     2400
gtgaagagta gtcaagattt agaaattgat ctcattcacc atcataaagt ccatcttgtg     2460
aaaaatgtac cagataattt agtacttgat acttacccag atgattcctg caacggaatt     2520
aaccgttgtg atgaacagaa gatggtaaat gcgcaactgg aaacagaaca tcatcatccg     2580
atggattgct gtgaagcggc tcaaacacat gagttttctt cctatattaa tacaggcgat     2640
ctaaatgcaa gtgtagatca aggcatttgg gttgtattga agttcgaac aacagatggt     2700
tatgcgacgc taggaaatct tgaattggta gaggtcggac cgttatcggg tgaatctcta     2760
gaacgtgaac aaagggataa tgcgaaatgg agtgcagagc taggaagaaa gcgtgcagaa     2820
acagagagag tatattatgc tgccaaacaa tccatcaatc atttatttgt ggattatcga     2880
gatcaacaat taaatccaca aatagggatg gcagatatta tggacgctca aatcttgtc     2940
gcatcaattt cagatgtata tagcgatgcc gtactgcaaa tccctggaat taactatgag     3000
atttacacag agctatccaa tcgcttacaa caagcatcgt atctgcatat gtctcgaaat     3060
gcgatgcaaa atgggggactt taacagcggt ctagatagtt ggaatgcaac agcgggtgct     3120
acggtacaac aggatggcaa tacgcatttc ttagttcttt ctcattggga tgcacaagtt     3180
tctcaacaat ttagagtgca gccgaattgt aaatatgtat tacgtgtaac agcagagaaa     3240
```

```
gtaggcggcg agacggata cgtgacaatc cgggatggtg ctcatcatac agaaacgctt    3300
acatttaatg catgtgatta tgatataaat ggcacgtacg tgactgataa tacgtatcta    3360
acaaaagaag tggtattcca tccggagaca caacatatgt gggtagaggt aagtgaaaca    3420
gaaggtgttt tccatataga cagtgttgag ttcatggaaa cccaacagta a             3471
```

<210> SEQ ID NO 3
<211> LENGTH: 3471
<212> TYPE: DNA
<213> ORGANISM: Bacillus thuringiensis

<400> SEQUENCE: 3

```
atgaatcaaa ataaacacgg aattattggc gcttccaatt gtggttgtgc atctgatgat    60
gttgcgaaat atccctttagc caacaatcca tattcatctg ctttaaattt aaattcttgt   120
caaaatagta gtattctcaa ctggattaac ataataggcg atgcagcaaa agaagcagta   180
tctattggga caaccatagt ctctcttatc acagcaccctt ctcttactgg attaatttca   240
atagtatatg accttatagg taaagtacta ggaggtagta gtggacaatc catatcagat   300
ttgtctatat gtgacttatt atctattatt gatttacggg taagtcagag tgtcttaaat   360
gatgggattg cagattttaa tggttctgta ctcttataca ggaactatttt agaggctctg   420 gatagctgga ataagaatcc taattctgct tctgctgaag aactccgtac tcgttttaga   480
atcgccgact cagaatttga tagaatttta acccgagggt ctttaacgaa tggtggctcg   540
ttagctagac aaaatgccca atattatta ttaccttctt ttgcgagcgc tgcatttttc    600
catttattac tactaaggga tgctactaga tatggcacta attgggggct atacaatgct   660
acacctttta taaattatca atcaaaacta gtagagctta ttgaactata tactgattat   720
tgcgtacatt ggtataatcg aggtttcaac gaactaagac aacgaggcac tagtgctaca   780
gcttggttag aatttcatag atatcgtaga gagatgacat tgatggtatt agatatagta   840
gcatcatttt caagtcttga tattactaat tacccaatag aaacagattt tcagttgagt   900
agggtcattt atacagatcc aattggtttt gtacatcgta gtagtcttag gggagaaagt   960
tggtttagct ttgttaatag agctaattttc tcagatttag aaaatgcaat acctaatcct  1020
agaccgtctt ggtttttaaa taatatgatt atatctactg gttcacttac attgccggtt  1080
agcccaagta ctgatagagc gagggtatgg tatggaagtc gagatcgaat ttcccctgct  1140
aattcacaat ttattactga actaatctct ggacaacata cgactgctac acaaactatt  1200
ttagggcgaa atatttag agtagattct caagcttgta atttaaatga taccacatat  1260
ggagtgaata gggcggtatt tatcatgat gcgagtgaag gttctcaaag atccgtgtac  1320 gagggggtata ttcgaacaac tgggatagat aaccctagag ttcaaaatat taacacttat  1380
ttacctggag aaaattcaga tatcccaact ccagaagact atactcatat attaagcaca  1440
acaataaatt taacaggagg acttagacaa gtagcatcta atcgccgttc atctttagta  1500
atgtatggtt ggacacataa aagtctggct cgtaacaata ccattaatcc agatagaatt  1560
acacagatac cattgacgaa ggttgatacc cgaggcacag gtgtttctta tgtgaatgat  1620
ccaggattta taggaggagc tctacttcaa aggactgacc atggttcgct tggagtattg  1680
agggtccaat tccacttca cttaagacaa caatatcgca ttagagtccg ttatgcttct  1740
acaacaaata ttcgattgag tgtgaatggc agtttcggta ctatttctca aaatctccct  1800
agtacaatga gattaggaga ggatttaaga tacggatctt ttgctataag agagtttaat  1860
acttctatta gacccactgc aagtccggac caaattcgat tgacaataga accatcttt   1920
```

```
attagacaag aggtctatgt agatagaatt gagttcattc cagttaatcc gacgcgagag    1980
gcgaaagagg atctagaagc agcaaaaaaa gcggtggcga gcttgtttac acgcacaagg    2040
gacggattac aagtaaatgt gaaagattat caagtcgatc aagcggcaaa tttagtgtca    2100
tgcttatcag atgaacaata tgggtatgac aaaaagatgt tattggaagc ggtacgtgcg    2160
gcaaaacgac ttagccgaga acgcaactta cttcaggatc cagattttaa tacaattaat    2220
agtacagaag aaaatggatg gaaagcaagt aacggcgtta ctattagtga gggcgggcca    2280
ttctataaag gccgtgcaat tcagctagca agcgcacgag aaaattatcc aacatacatt    2340
tatcaaaaag tagatgcatc ggagttaaag ccatatacac gctatagact ggatggattc    2400
gtgaagagta gtcaagattt agaaattgat ctcattcacc atcataaagt ccatcttgtg    2460
aaaaatgtac cagataattt agtacttgat acttacccag atgattcctg caacggaatt    2520
aaccgttgtg atgaacagaa gatggtaaat gcgcaactgg aaacaggaca tcatcatccg    2580
atggattgct gtgaagcggc tcaaacacat gagttttctt cctatattaa tacaggcgat    2640
ctaaatgcaa gtgtagatca aggcatttgg gttgtattga agttcgaac aacagatggt    2700 tatgcgacgc taggaaatct tgaattggta gaggtcggac cgttatcggg tgaatctcta    2760
gaacgtgaac aaagggataa tgcgaaatgg agtgcagagc taggaagaaa gcgtgcagaa    2820
acagagagag tatattatgc tgccaaacaa tccatcaatc atttatttgt ggattatcaa    2880
gatcaacaat taaatccaca aataggggatg gcagatatta tggacgctca aatcttgtc    2940 gcatcaattt cagatgtata tagcgatgcc gtactgcaaa tccctggaat taactatgag    3000
atttacacag agctatccaa tcgcttacaa caagcatcgt atctgcatac gtctcgaaat    3060
gcgatgcaaa atggggactt taacagcggt ctagatagtt ggaatgcaac agcgggtgct    3120
acggtacaac aggatggcaa tacgcatttc ttagttcttt ctcattggga tgcacaagtt    3180
tctcaacaat ttagagtgca gccgaattgt aaatatgtat tacgtgtaac agcagagaaa    3240
gtaggcggcg gagacggata cgtgacaatc cgggatggtg ctcatcatac agaaacgctt    3300
acatttaatg catgtgatta tgatataaat ggcacgtacg tgactgataa tacgtatcta    3360
acaaaagaag tggtattcca tccggagaca caacatatgt gggtagaggt aagtgaaaca    3420
gaaggtgttt tccatataga cagtgttgag ttcatggaaa cccaacagta a              3471
```

<210> SEQ ID NO 4
<211> LENGTH: 3459
<212> TYPE: DNA
<213> ORGANISM: Bacillus thuringiensis

<400> SEQUENCE: 4

```
atgaatcgaa ataatccaaa tgaatatgaa attattgatg cccctattg tgggtgtccg     60 tcagatgatg atgtgaggta tcctttggca agtgacccaa atgcagcgtt ccaaaatatg    120
aactataaag agtatttaca aacgtatgat ggagactaca caggttctct tatcaatcct    180
aacttatcta ttaatcctag agatgtacta caaacaggta ttaatattgt gggaagaata    240
ctagggtttt taggtgttcc atttgcgggt caactagtta cttctctata cttttctctta    300 aatcagttgt ggccaactaa tgataatgca gtatgggaag cttttatggc gcaaatagaa    360
gagctaatcg atcaaaaaat atcggcgcaa gtagtaagga atgcactcga tgacttaact    420
ggattacacg attattatga ggagtattta gcagcattag aggagtggct ggaaagaccg    480
aacggagcaa gagctaactt agttacacag aggtttgaaa acctgcatac tgcatttgta    540
```

```
actagaatgc caagctttgg tacgggtcct ggtagtcaaa gagatgcggt agcgttgttg    600
acggtatatg cacaagcagc gaatttgcat ttgttattat taaaagatgc agaaatctat    660
ggggcaagat ggggacttca acaagggcaa attaacttat atttttaatgc tcaacaagaa   720 cgtactcgaa tttataccaa tcattgcgtg gaaacatata atagaggatt agaagatgta    780
agaggaacaa atacagaaag ttggttaaat taccatcgat tccgtagaga gatgacatta    840
atggcaatgg atttagtggc cttattccca tactataatg tgcgacaata tccaaatggg    900
gcaaatccac agcttacacg tgaaatatat acggacccaa tcgtatataa tccaccagct    960
aatcagggaa tttgccgacg ttgggggaat aatccgtata atacattttc tgaacttgaa   1020
aatgctttta ttcgcccgcc acatcttttt gataggttga atagattaac tatttctaga   1080
aaccgatata cagctccaac aactaatagc tacctagact attggtcagg tcatacttta   1140
caaagccagt atgcaaataa cccgacgaca tatgaaacta gttacggtca gattacctct   1200
aacacacgtt tattcaatac gactaatgga gccaatgcaa tagattcaag ggcaagaaat   1260
tttggtaact tatacgctaa tttgtatggc gttagcagct tgaacatttt cccaacaggt   1320
gtgatgagtg aaatcacctc agcccctaat acgtgttggc aagacttac tacaactgag    1380 gaactaccac tagtgaataa taattttaat cttttatctc atgttacttt cttacgcttc   1440
aatactactc agggtggccc ccttgcaact gtagggtttg tacccacata tgtgtggaca   1500
cgtcaagatg tagattttaa taatataatt actcccaata gaattactca ataccagtg    1560 gtaaaggcat atgagctaag tagtggtgct actgtcgtga aggtccagg attcacagga    1620 ggagatgtaa tccgaagaac aaatactggt ggattcggag caataagggt gtcggtcact   1680
ggaccgctaa cacaacgata tcgcataagg ttccgttatg cttcgacaat agattttgat   1740
ttctttgtaa cacgtggagg aactactata aataatttta gatttacacg tacaatgaac   1800
aggggacagg aatcaagata tgaatcctat cgtactgtag agtttacaac tccttttaac   1860
tttacacaaa gtcaagatat aattcgaaca tctatccagg gacttagtgg aaatggggaa   1920
gtataccttg atagaattga aatcatccct gtaaatccaa cacgagaagc ggaagaggat   1980
ttagaagcgg cgaagaaagc ggtggcgagc ttgtttacac gcacaaggga cggattacaa   2040
gtaaatgtga cagattatca agtcgatcaa gcggcaaatt tagtgtcatg cttatcagat   2100
gaacaatatg cgcatgataa aaagatgtta ttggaagcgg tacgcgcggc aaaacgcctc   2160
agccgagaac gtaacttact tcaggaccca gattttaata caatcaatag tacagaagaa   2220
aatggatgga aagcaagtaa cggcgttact attagtgagg gcggtccatt ctataaaggc   2280
cgtgcacttc agctagcaag tgcacgagaa aattacccaa catacatcta tcaaaaagta   2340
gatgcatcgg agttaaaacc ttatacacga tatagactgg atgggttcgt gaagagtagt   2400
caagatttag aaattgatct cattcaccat cataaagtcc atcttgtgaa aaatgtacta   2460
gataatttag tatctgatac ttacccagat gattcttgta gtggaatcaa tcgatgtgag   2520
gaacaacaga tggtaaatgc gcaactggaa acagaacatc atcatccgat ggattgctgt   2580
gaagcagctc aaacacatga gttttcttcc tatattgata cagggatttt aaattcgact   2640
gtagaccagg gaatctgggt gatctttaaa gttcgaacaa cagatggtta tgcgacgcta   2700
ggaaatcttg aattggtaga ggtcggaccg ttattgggtg aacctctaga acgtgaacaa   2760
agagaaaatg cgaaatggaa tgcagagtta ggaagaaaac gtgcagaaac agatcgcgtg   2820
tatcaagatg ccaaacaatc catcaatcat ttatttgtgg attatcaaga tcaacaatta   2880
aatccacaaa tagggatggc agatattatg gacgctcaaa atcttgtcgc atcaatttca   2940
```

-continued

| | |
|---|---|
| gatgtatata gcgatgcagt actgcaaatc cctggaatta actatgagat ttacacagag | 3000 |
| ctgtccaatc gcttacaaca agcatcgtat ctgtatacgt ctcgaaatgc ggtgcaaaat | 3060 |
| ggggacttta caacgggct agatagctgg aatgcaacag cgggtgcatc ggtacaacag | 3120 |
| gatggcaata cgcatttctt agttcttcct cattgggatg cacaagtttc ccaacaattt | 3180 |
| agagtgcagc cgaattgtaa atatgtatta cgtgtaacag cagagaaagt aggcggcgga | 3240 |
| gacggatacg tgactatccg ggatggtgct catcatacag aaacgcttac atttaatgca | 3300 |
| tgtgattatg atataaatgg cacgtacgtg actgataata cgtatctaac aaaagaagtg | 3360 |
| atattctatt cacatacaga acacatgtgg gtagaggtaa atgaaacaga aggtgcattt | 3420 |
| catatagata gtattgaatt cgttgaaaca gaaaagtaa | 3459 |

<210> SEQ ID NO 5
<211> LENGTH: 3468
<212> TYPE: DNA
<213> ORGANISM: Bacillus thuringiensis

<400> SEQUENCE: 5

| | |
|---|---|
| atgaatcgaa ataatcaaga tgaatatgaa attattgacg cttccacttg tggttgttcg | 60 |
| tcagatgatg ttgttcaata ccctttggca agagatccga atgctgtatt ccaaaatatg | 120 |
| cattataaag attatttgca aacgtatgat ggagactata caggttctct tataaatcct | 180 |
| aacttatcta ttaatcctag agatgtactg caaactggaa ttaatattgt gggaagatta | 240 |
| ctaggatttc taggtgttcc atttgctggt cagttagtta cttttctatac ctttcttta | 300 |
| aatcaactgt ggccaacaaa tgataatgca gtatgggaag cttttatggc acaaatagaa | 360 |
| gagcttatta tcaaagaat atccgaagca gtagtaggga cagcagcgga tcatttaacg | 420 |
| ggattacacg ataattatga gttatatgta gaggcattgg aggaatggct ggaaagaccg | 480 |
| aatgctgcta gaactaatct actttttaat agatttacca ccctagatag tcttttttaca | 540 |
| caatttatgc caagctttgg tactggacct ggaagtcaaa actacgcagt tccattactt | 600 |
| acagtatacg cacaagcagc gaaccttcat ttgttattat taaggatgc tgaaatatat | 660 |
| ggagcaagat ggggactgaa ccaaaatcag attaactcat ccatacgcg ccaacaagaa | 720 |
| cgtactcaat attatacaaa tcattgcgta acgacgtata ataccggttt agatagatta | 780 |
| agaggcacaa atactgaaag ttggttaaat tatcatcgtt tccgtagaga gatgacatta | 840 |
| atggcaatgg atttagtagc gctattccca tattataatg tacgacaata tccaaatgga | 900 |
| gcaaatcctc agcttacacg tgaaatatat acagatccaa ttgtatttaa tccaccagct | 960 |
| aatgtgggat tatgtagacg ttggggcaat aacccatata atagattttc tgaactagaa | 1020 |
| aacgcttta tccgccgcc acatctttt gatagattga ataccttaac aattagtaga | 1080 |
| aatagatttg acgttgggtc aaactttata gaaccgtggt ctggacatac gttacgccgt | 1140 |
| agttattcga ataattcgac agtatatgaa gatagttatg ccaaattac agccacaaga | 1200 |
| acaacaatta atctgccggc taatggaact ggccgagtag aatcaacagc agtagatttt | 1260 |
| cgtagcgcgc ttgtggggat atacggtgtt aatagagctt cttttattcc aggtggtgtg | 1320 |
| tttagtggca cgactcagcc ttctactgga ggatgtagag atttgtatga ttcaagtgat | 1380 |
| gaattaccac cagacgaaag tactggaagt tttgcccata gactatctca tgttaccttt | 1440 |
| ttaagtttta caactaatca ggccggttcc atagccaatt caggacgcgt ccctacttat | 1500 |
| gtctggaccc atcgcgatgt ggactttaat aatacaatta accccaatag aattactcaa | 1560 |

```
ataccagtgg taaaggcata tgagctaagt agtggtgcta ctgtcgtgaa aggtccagga    1620
ttcacaggag gagatgtaat ccgaagaaca aatattggtg ggttcggagc aataagggtg    1680
tcggtcactg gaccgctaac acaacgatat cgcataaggt tccgttatgc ttcgacaata    1740
gattttgatt tctttgtaac acgtggagga actactataa ataattttag atttacacgt    1800
acaatgaaca ggggacagga atcaagatat gaatcctatc gtactgtaga gtttacaact    1860
ccttttaact ttacacaaag tcaagatata attcgaacat ctatccaggg acttagtgga    1920
aatggggaag tataccttga tagaattgaa atcatccctg taaatccaac acgagaagcg    1980
gaagaggatc tagaagcagc gaagaaagcg gtggcgagct tgtttacacg tacaagggac    2040
ggattacaag taaatgtgac agattatcaa gtcgatcaag cggcaaattt agtgtcatgc    2100 ttatcgatg aacaatatgg gcatgacaaa aagatgttat tggaagcggt aagagcggca    2160
aaacgcctca gccgagaacg caacttactt caagatccag attttaatac aatcaatagt    2220
acagaagaaa atggatggaa agcaagtaac ggcgttacta ttagcgaggg cggtccattc    2280
tataaaggcc gtgcgcttca gctagcaagc gcaagagaaa attacccaac atacatttat    2340
caaaaagtaa atgcatcaga gttaaagccg tatacgtt atagactgga tgggttcgtg    2400
aagagtagtc aagatttaga aattgatctc attcaccatc ataaagtcca tctcgtgaaa    2460
aatgtaccag ataatttagt atccgatact tactcggatg gttcttgcag tggaatgaat    2520
cgatgtgagg aacaacagat ggtaaatgcg caactggaaa cagaacatca tcatccgatg    2580
gattgctgtg aagcggctca aacacatgag ttttcttcct atattaatac aggcgatcta    2640
aattcaagtg tagatcaagg catttgggtt gtattgaaag ttcgaacaac cgatggttat    2700
gcgacgctag gaaatcttga attggtagag gtcggaccgt tatcgggtga atctctagaa    2760
cgtgaacaaa gggataatgc gaaatggagt gcagagctag aagaaagcg tgcagaaaca    2820 gatcgcgtgt atcaagatgc caaacaatcc atcaatcatt tatttgtgga ttatcaagat    2880
caacaattaa atccagaaat agggatggca gatattattg acgctcaaaa tcttgtcgca    2940
tcaatttcag atgtgtatag cgatgcagta ctgcaaatcc ctggaattaa ctatgagatt    3000
tacacagagc tatccaatcg cttacaacaa gcatcgtatc tgtatacgtc tcgaaatgcg    3060
gtgcaaaatg gggactttaa cagcggtcta gatagttgga atgcaacagg ggggctacg    3120 gtacaacagg atggcaatac gcatttctta gttctttctc attgggatgc acaagtttct    3180
caacaattta gagtgcagcc gaattgtaaa tatgtattac gtgtaacagc agagaaagta    3240
ggcggcggag acggatacgt gacaatccgg gatggtgctc atcatacaga aaagcttaca    3300
tttaatgcat gtgattatga tataaatggc acgtacgtga ctgataatac gtatctaaca    3360
aaagaagtgg tattctattc acatacgaaa cacatgtggg tagaggtaag tgaaacagaa    3420
ggtgcatttc atatagatag tattgaattc gttgaaacag aaaagtaa              3468

<210> SEQ ID NO 6
<211> LENGTH: 3471
<212> TYPE: DNA
<213> ORGANISM: Artificial Sequence
<220> FEATURE:
<223> OTHER INFORMATION: Synthetic Cry Gene

<400> SEQUENCE: 6
atgaatcaga acaagcacgg catcattggg gcctcgaact gcggctgcgc ctccgacgat      60
gtggctaagt accctctcgc taacaaccct tactccagcg ccctgaacct caattcctgc     120
cagaactcgt ctatcctcaa ttggattaac atcattgggg acgccgcgaa ggaggctgtc     180
```

```
agcatcggca ccacgattgt ttcactgatc acggccccgt ccctgacagg cctcatcagc    240
attgtgtacg acctcatcgg gaaggtccta ggcgggtcat ccggccagag catttcggac    300
ctgtcgatct gcgatctcct gtctatcatt gacctcaggg tgtctcagtc agtcctgaac    360
gacgggatcg ccgatttcaa tggctcagtg ctcctgtacc gcaactacct ggaggcgctc    420
gactcctgga acaagaatcc caactccgct agcgctgagg agctgaggac caggttcagg    480
attgccgact ccgagttcga tcgcatcctc actcgcggct cactgaccaa tggcggctcc    540
ctcgcccgcc agaacgctca gatcctcctg ctccctagct tcgcgtcggc tgccttcttc    600
cacctgctcc tgctcaggga cgctacgcgc tacggaacca actggggcct ctacaatgct    660
actccgttca taaactacca gtccaagctg gtcgagctga tcgagctgta caccgactac    720
tgcgttcact ggtacaatag ggggttcaac gagctgaggc agaggggcac gagcgctaca    780
gcttggctgg agttccatcg ctaccgcagg gagatgacgc tcatggttct ggacatcgtg    840
gccagcttca gctcgctcga tattactaac tacccctatc gagaccgactt ccagctgtcg    900 cgcgtgattt acaccgaccc gatcgggttc gtccaccgct cttcactgag gggcgagtct    960
tggttctcat tcgtcaatag ggcgaacttc tcggacctcg agaatgctat cccgaacccc    1020
cggccatctt ggttcctgaa caatatgatc atttccactg gcagcctgac cctccccgtt    1080
tcgccatcta cggatcgcgc gagggtgtgg tacggctcac gggaccgcat ctcaccggct    1140
aactcccagt tcattacaga gctgatctct ggccagcaca caactgctac acagactatt    1200
ctgggccgga atatcttccg cgtggacagc caggcctgca atctcaacga taccacgtac    1260
ggcgtcaaca gggctgtttt ctaccatgac gcctcggagg gctctcagcg ctcagtctac    1320
gagggataca tcaggacaac tggcatcgat aatcctcggg tgcagaatat taacacgtac    1380
ctcccgggcg agaacagcga catccctacg ccggaggatt acacacacat tctgtcgacc    1440
acaatcaacc tcaccggcgg gctgaggcag gtcgcttcta acaggcgctc cagcctcgtt    1500
atgtacggct ggactcataa gtcactggcg cgcaacaaca caatcaaccc tgataggatc    1560
actcagattc cgctcaccaa ggtggacact aggggaccg gcgtgtcgta cgtcaacgat    1620
cccggcttca tcggcggggc cctgctccag cgcaccgacc acggctccct cggggttctg    1680
cgggtgcagt tcccactgca tctccgccag cagtacagga ttcgggtccg ctacgcgtcc    1740
acaactaaca tccgcctcag cgtgaatggg tcgttcggca cgatctccca gaacctgccc    1800
agcacaatga ggctcgggga ggacctgcgc tacggctcct tcgccattcg ggagttcaac    1860
acgagcatcc gccccacagc gtcgccagat cagattaggc tcactatcga gccaagcttc    1920
atcaggcagg aggtctacgt tgaccggatc gagttcattc ctgtcaaccc gacgagggag    1980
gctaaggagg atctggaggc tgctaagaag gctgtggcta gcctcttcac caggacgagg    2040
gacggcctgc aagtgaatgt caaggactac caggttgatc aggccgcgaa cctcgtgtcc    2100
tgcctgagcg acgagcagta cggctacgat aagaagatgc tgctcgaggc ggtcagggct    2160
gctaagaggc tctccaggga gaggaacctg ctccaggacc ctgatttcaa tacgatcaac    2220
agcacagagg agaacgggtg gaaggcgtct aatggcgtga ccatttcaga gggcggccca    2280
ttctacaagg gcagggctat ccagctggct tcggctcggg agaactaccc cacgtacatc    2340
taccagaagg tcgacgcctc tgagctgaag ccatacacac gctaccgcct ggatggcttc    2400
gtgaagtcgt ctcaggacct cgagatcgat ctgattcacc atcacaaggt ccacctggtt    2460
aagaatgtgc ccgacaacct ggtcctcgac acctacccag acgattcctg caatggcatc    2520
```

```
aacaggtgcg acgagcagaa gatggtgaac gcccagctcg agaccgagca tcaccatccg    2580
atggactgct gcgaggcggc tcagacgcac gagttctcat cctacattaa cacagggac     2640 ctgaatgcca gcgtggatca gggcatctgg gtggtcctca aagtcaggac cacggacggg    2700
tacgctacgc tgggcaacct ggagctggtt gaagtggggc cactctcggg cgagtctctg    2760
gagagggagc agagggacaa cgccaagtgg agcgctgagc tgggcaggaa gagggctgag    2820
accgagaggg tctactacgc cgcgaagcag tcgatcaatc acctcttcgt ggactacagg    2880
gatcagcagc tgaaccccca gattggcatg gctgacatca tggatgccca gaacctcgtc    2940
gcgtcaatct ccgacgtgta ctccgatgcg gtcctgcaga tcccaggcat caactacgag    3000
atctacacgg agctgagcaa ccggctgcag caggcctcgt acctccacat gtctcgcaat    3060
gcgatgcaga acgggacctt caattctggc ctggattcat ggaatgcgac tgctggggcc    3120
accgttcagc aggacggcaa cacccacttc ctggtgctct cccattggga tgcccaagtt    3180
agccagcagt tccgcgtgca gccgaactgc aagtacgtcc tgagggttac tgctgagaag    3240
gtcggcgggg gcgacggcta cgttaccatc cgcgatggcg ctcaccatac agagactctc    3300
accttcaacg cctgcgacta cgatatcaat ggcacgtacg tgacagacaa cacttacctg    3360
accaaggagg ttgtgttcca cccggagacc cagcatatgt gggtcgaggt tagcgagacg    3420
gagggcgtgt tccacataga cagcgttgag ttcatggaga cccagcagta g             3471
```

<210> SEQ ID NO 7
<211> LENGTH: 3471
<212> TYPE: DNA
<213> ORGANISM: Artificial Sequence
<220> FEATURE:
<223> OTHER INFORMATION: Synthetic Cry Gene

<400> SEQUENCE: 7

```
atgaatcaga acaagcacgg catcattggg gcctcgaact gcggctgcgc ctccgacgat      60
gtggctaagt accctctcgc taacaaccct tactccagcg ccctgaacct caattcctgc    120
cagaactcgt ctatcctcaa ttggattaac atcattgggg acgccgcgaa ggaggctgtc    180
agcatcggca ccacgattgt ttcactgatc acggccccgt ccctgacagg cctcatcagc    240
attgtgtacg acctcatcgg gaaggtccta ggcgggtcat ccggccagag catttcggac    300
ctgtcgatct gcgatctcct gtctatcatt gacctcaggg tgtctcagtc agtcctgaac    360
gacgggatcg ccgatttcaa tggctcagtg ctcctgtacc gcaactacct ggaggcgctc    420
gactcctgga acaagaatcc caactccgct agcgctgagg agctgaggac caggttcagg    480
attgccgact ccgagttcga tcgcatcctc actcgcggct cactgaccaa tggcggctcc    540
ctcgcccgcc agaacgctca gatcctcctg ctccctagct tcgcgtcggc tgccttcttc    600
cacctgctcc tgctcaggga cgctacgcgc tacggaacca actggggcct ctacaatgct    660
actccgttca taaactacca gtccaagctg gtcgagctga tcgagctgta caccgactac    720
tgcgttcact ggtacaatag ggggttcaac gagctgaggc agaggggcac gagcgctaca    780
gcttggctgg agttccatcg ctaccgcagg gagatgacgc tcatggttct ggacatcgtg    840
gccagcttca gctcgctcga tattactaac taccctatcg agaccgactt ccagctgtcg    900
cgcgtgattt acaccgaccc gatcgggttc gtccaccgct cttcactgag ggcgagtct    960 tggttctcat tcgtcaatag ggcgaacttc tcggacctcg agaatgctat cccgaacccc    1020
cggccatctt ggttcctgaa caatatgatc atttccactg gcagcctgac cctccccgtt    1080
tcgccatcta cggatcgcgc gagggtgtgg tacggctcac gggaccgcat ctcaccggct    1140
```

```
aactcccagt tcattacaga gctgatctct ggccagcaca caactgctac acagactatt    1200
ctgggccgga atatcttccg cgtggacagc caggcctgca atctcaacga taccacgtac    1260
ggcgtcaaca gggctgtttt ctaccatgac gcctcggagg gctctcagcg ctcagtctac    1320
gagggataca tcaggacaac tggcatcgat aatcctcggg tgcagaatat aaacacgtac    1380
ctcccgggcg agaacagcga catccctacg ccggaggatt acacacacat tctgtcgacc    1440
acaatcaacc tcaccggcgg gctgaggcag gtcgcttcta acaggcgctc cagcctcgtt    1500
atgtacggct ggactcataa gtcactggcg cgcaacaaca caatcaaccc tgataggatc    1560
actcagattc cgctcaccaa ggtggacact aggggaccg gcgtgtcgta cgtcaacgat     1620
cccggcttca tcggcggggc cctgctccag cgcaccgacc acggctccct cggggttctg    1680
cgggtgcagt tcccactgca tctccgccag cagtacagga ttcgggtccg ctacgcgtcc    1740
acaactaaca tccgcctcag cgtgaatggg tcgttcggca cgatctccca gaacctgccc    1800
agcacaatga ggctcgggga ggacctgcgc tacggctcct tcgccattcg ggagttcaac    1860
acgagcatcc gccccacagc gtcgccagat cagattaggc tcactatcga gccaagcttc    1920
atcaggcagg aggtctacgt tgaccggatc gagttcattc ctgtcaaccc gacgagggag    1980
gctaaggagg atctggaggc tgctaagaag gctgtggcta gcctcttcac caggacgagg    2040
gacggcctgc aagtgaatgt caaggactac caggttgatc aggccgcgaa cctcgtgtcc    2100
tgcctgagcg acgagcagta cggctacgat aagaagatgc tgctcgaggc ggtcagggct    2160
gctaagagc tctccaggga gaggaacctg ctccaggacc ctgatttcaa tacgatcaac      2220
agcacagagg agaacgggtg gaaggcgtct aatggcgtga ccatttcaga gggcggccca    2280
ttctacaagg gcagggctat ccagctggct tcggctcggg agaactaccc cacgtacatc    2340
taccagaagg tcgacgcctc tgagctgaag ccatacacac gctaccgcct ggatggcttc    2400
gtgaagtcgt tcaggacct cgagatcgat ctgattcacc atcacaaggt ccacctggtt      2460
aagaatgtgc ccgacaacct ggtcctcgac acctacccag acgattcctg caatggcatc    2520
aacaggtgcg acgagcagaa gatggtgaac gcccagctcg agaccgagca tcaccatccg    2580
atggactgct gcgaggcggc tcagacgcac gagttctcat cctacattaa cacaggggac    2640
ctgaatgcca gcgtggatca gggcatctgg gtggtcctca aagtcaggac cacggacggg    2700
tacgctacgc tgggcaacct ggagctggtt gaagtggggc cactctcggg cgagtctctg    2760
gagagggagc agagggacaa cgccaagtgg agcgctgagc tgggcaggaa gagggctgag    2820
accgagaggg tctactacgc cgcgaagcag tcgatcaatc acctcttcgt ggactacagg    2880
gatcagcagc tgaaccccca gattggcatg gctgacatca tggatgccca gaacctcgtc    2940
gcgtcaatct ccgacgtgta ctccgatgcg gtcctgcaga tcccaggcat caactacgag    3000
atctacacgg agctgagcaa ccggctgcag caggcctcgt acctccacat gtctcgcaat    3060
gcgatgcaga acgggacttt caattctggc ctggattcat ggaatgcgac tgctggggcc    3120
accgttcagc aggacggcaa cacccacttc ctggtgctct cccattggga tgcccaagtt    3180
agccagcagt tccgcgtgca gccgaactgc aagtacgtcc tgagggttac tgctgagaag    3240
gtcggcgggg gcgacggcta cgttaccatc cgcgatggcg ctcaccatac agagactctc    3300
accttcaacg cctgcgacta cgatatcaat ggcacgtacg tgacagacaa cacttacctg    3360
accaaggagg ttgtgttcca cccggagacc cagcatatgt gggtcgaggt tagcgagacg    3420
gagggcgtgt tccacataga cagcgttgag ttcatggaga cccagcagta g              3471
```

<210> SEQ ID NO 8
<211> LENGTH: 3471
<212> TYPE: DNA
<213> ORGANISM: Artificial Sequence
<220> FEATURE:
<223> OTHER INFORMATION: Synthetic Cry gene

<400> SEQUENCE: 8

```
atgaatcaga acaagcacgg catcattggg gcctcgaact gcggctgcgc ctccgacgat      60
gtggctaagt accctctcgc taacaaccct tactccagcg ccctgaacct caattcctgc     120
cagaactcgt ctatcctcaa ttggattaac atcattgggg acgccgcgaa ggaggctgtc     180
agcatcggca ccacgattgt ttcactgatc acggccccgt ccctgacagg cctcatcagc     240
attgtgtacg acctcatcgg gaaggtccta ggcgggtcat ccggccagag catttcggac     300
ctgtcgatct gcgatctcct gtctatcatt gacctcaggg tgtctcagtc agtcctgaac     360
gacgggatcg ccgatttcaa tggctcagtg ctcctgtacc gcaactacct ggaggcgctc     420
gactcctgga acaagaatcc caactccgct agcgctgagg agctgaggac caggttcagg     480
attgccgact ccgagttcga tcgcatcctc actcgcggct cactgaccaa tggcggctcc     540
ctcgcccgcc agaacgctca gatcctcctg ctccctagct tcgcgtcggc tgccttcttc     600
cacctgctcc tgctcaggga cgctacgcgc tacggaacca actggggcct ctacaatgct     660
actccgttca taactacca gtccaagctg gtcgagctga tcgagctgta caccgactac     720
tgcgttcact ggtacaatag ggggttcaac gagctgaggc agaggggcac gagcgctaca     780
gcttggctgg agtccatcg ctaccgcagg agatgacgc tcatggttct ggacatcgtg     840
gccagcttca gctcgctcga tattactaac taccctatcg agaccgactt ccagctgtcg     900
cgcgtgattt acaccgaccc gatcgggttc gtccaccgct cttcactgag gggcgagtct     960
tggttctcat tcgtcaatag ggcgaacttc tcggacctcg agaatgctat cccgaacccc    1020
cggccatctt ggttcctgaa caatatgatc atttccactg cagcctgac cctccccgtt    1080
tcgccatcta cggatcgcgc gagggtgtgg tacggctcac gggaccgcat ctcaccggct    1140
aactcccagt tcattacaga gctgatctct ggccagcaca caactgctac acagactatt    1200
ctgggccgga atatcttccg cgtggacagc caggcctgca atctcaacga taccacgtac    1260
ggcgtcaaca gggctgtttt ctaccatgac gcctcggagg ctctcagcg ctcagtctac    1320
gagggataca tcaggacaac tggcatcgat aatcctcggg tgcagaatat taacacgtac    1380
ctcccgggcg agaacagcga catccctacg ccggaggatt acacacacat tctgtcgacc    1440
acaatcaacc tcaccggcgg gctgaggcag gtcgcttcta acaggcgctc cagcctcgtt    1500
atgtacggct ggactcataa gtcactggcg cgcaacaaca caatcaaccc tgataggatc    1560
actcagattc cgctcaccaa ggtggacact aggggaccg gcgtgtcgta cgtcaacgat    1620
cccggcttca tcggcggggc cctgctccag cgcaccgacc acggctccct cggggttctg    1680
cgggtgcagt tcccactgca tctccgccag cagtacagga ttcgggtccg ctacgcgtcc    1740
acaactaaca tccgcctcag cgtgaatggg tcgttcggca cgatctccca gaacctgccc    1800
agcacaatga ggctcgggga ggacctgcgc tacggctcct tcgccattcg ggagttcaac    1860
acgagcatcc gccccacagc gtcgccagat cagattaggc tcactatcga gccaagcttc    1920
atcaggcagg aggtctacgt tgaccggatc gagttcattc ctgtcaaccc gacgagggag    1980
gctaaggagg atctggaggc tgctaagaag gctgtggcta gcctcttcac caggacgagg    2040
gacggcctgc aagtgaatgt caaggactac caggttgatc aggccgcgaa cctcgtgtcc    2100
```

```
tgcctgagcg acgagcagta cggctacgat aagaagatgc tgctcgaggc ggtcagggct    2160
gctaagaggc tctccaggga gaggaacctg ctccaggacc ctgatttcaa tacgatcaac    2220
agcacagagg agaacggggtg gaaggcgtct aatggcgtga ccatttcaga gggcggccca   2280
ttctacaagg gcagggctat ccagctggct tcggctcggg agaactaccc cacgtacatc    2340
taccagaagg tcgacgcctc tgagctgaag ccatacacac gctaccgcct ggatggcttc    2400
gtgaagtcgt ctcaggacct cgagatcgat ctgattcacc atcacaaggt ccacctggtt    2460
aagaatgtgc ccgacaacct ggtcctcgac acctacccag acgattcctg caatggcatc    2520
aacaggtgcg acgagcagaa gatggtgaac gcccagctcg agaccggaca tcaccatccg    2580
atggactgct gcgaggcggc tcagacgcac gagttctcat cctacattaa cacaggggac    2640
ctgaatgcca gcgtggatca gggcatctgg gtggtcctca agtcaggac cacggacggg     2700
tacgctacgc tgggcaacct ggagctggtt gaagtggggc cactctcggg cgagtctctg    2760
gagagggagc agagggacaa cgccaagtgg agcgctgagc tgggcaggaa gagggctgag    2820
accgagaggg tctactacgc cgcgaagcag tcgatcaatc acctcttcgt ggactaccaa    2880
gatcagcagc tgaaccccca gattggcatg gctgacatca tggatgccca gaacctcgtc    2940
gcgtcaatct ccgacgtgta ctccgatgcg gtcctgcaga tcccaggcat caactacgag    3000
atctacacgg agctgagcaa ccggctgcag caggcctcgt acctccacac gtctcgcaat    3060
gcgatgcaga acggggactt caattctggc ctggattcat ggaatgcgac tgctggggcc    3120
accgttcagc aggacggcaa cacccacttc ctggtgctct cccattggga tgcccaagtt    3180
agccagcagt tccgcgtgca gccgaactgc aagtacgtcc tgagggttac tgctgagaag    3240
gtcggcgggg gcgacggcta cgttaccatc cgcgatggcg ctcaccatac agagactctc    3300
accttcaacg cctgcgacta cgatatcaat ggcacgtacg tgacagacaa cacttacctg    3360
accaaggagg ttgtgttcca cccggagacc cagcatatgt gggtcgaggt tagcgagacg    3420
gagggcgtgt tccacataga cagcgttgag ttcatggaga cccagcagta g             3471
```

<210> SEQ ID NO 9
<211> LENGTH: 3459
<212> TYPE: DNA
<213> ORGANISM: Artificial Sequence
<220> FEATURE:
<223> OTHER INFORMATION: Synthetic Cry Gene

<400> SEQUENCE: 9

```
atgaacagga caacccaaa cgagtacgag attattgatg ctccatactg cggctgcccc      60
tccgatgacg atgtgcgcta ccccctcgcc agcgacccga acgccgcgtt ccagaatatg    120
aactacaagg agtacctgca gacctacgac ggcgattaca cggggtcact gattaatcca    180
aacctctcca tcaatcctcg cgacgtcctc cagaccggaa tcaacattgt tggccgcatc    240
ctcggcttcc tgggcgtgcc gttcgctggc cagctggtta cctttctacac gttcctcctg   300
aaccagctct ggcctacgaa tgacaacgcg gtgtgggagg ccttcatggc gcagatcgag    360
gagctgattg atcagaagat ctccgctcag gtggtcagga cgccctcga cgatctgacc     420
ggcctccacg actactacga ggagtacctg ctgctctcg aggagtggct cgagaggcca     480
aacggcgctc gcgctaatct ggtcacgcag cgcttcgaga acctccatac cgccttcgtg    540
acgaggatgc cgagcttcgg gacaggcccc gggtcgcaga gggacgcggt tgctctcctg    600
actgtgtacg cgcaggcggc taacctgcac ctcctgctcc tgaaggatgc tgagatctac    660
```

```
ggcgctcggt gggggctgca gcagggccag atcaacctct acttcaatgc ccagcaggag    720
cgcacaagga tctacactaa ccactgcgtt gagacctaca ataggggct cgaggacgtg     780
cggggcacga acacagagag ctggctgaat taccatcgct tccgcaggga gatgacgctc    840
atggcgatgg acctcgtggc gctcttcccc tactacaacg tccgccagta cccaaatggc    900
gccaaccctc agctgacaag ggagatctac actgacccga tcgtgtacaa cccaccagct    960
aatcagggga tctgcaggcg ctggggcaac aatccctaca acaccttctc tgagctggag   1020
aatgcgttca ttaggccacc tcacctcttc gaccgcctga acaggctcac catctcccgg   1080
aatcgctaca cggctccaac cacgaactcg tacctggatt actggtctgg ccataccctc   1140
cagtcacagt acgcgaacaa tcctacaact tacgagacgt cctacggcca gattacaagc   1200
aacactcgcc tcttcaatac cacgaacggc gctaatgcta tcgacagcag ggcccggaac   1260
ttcgggaatc tgtacgcgaa tctctacggc gtctccagcc tgaacatttt cccaaccggc   1320
gttatgtcag agatcacctc cgcccctaac acgtgctggc aggacctcac aactaccgag   1380
gagctgccac tggtgaacaa taacttcaat ctcctgtccc acgtcacatt cctgaggttc   1440
aacacgacac agggcggccc actcgcgact gttggcttcg tgcccaccta cgtgtggacg   1500
cggcaggacg tcgatttcaa taacatcatt acaccaaacc gcatcactca gattcctgtt   1560
gtgaaggcgt acgagctgtc gtctggcgct acagtcgtta agggcccggg gttcactggc   1620
ggggacgtca ttaggaggac taacaccggc gggttcgggg ctatcagggt gagcgtcaca   1680
ggcccctca ctcagcgcta caggattcgg ttccgctacg cgtcgaccat cgacttcgat   1740
ttcttcgtca cgcgcggcgg gactaccatc aataacttcc ggttcacgcg caccatgaac   1800
aggggccagg agagccggta cgagtcgtac cgcaccgtgg agttcacgac accgttcaac   1860
ttcacacaga gccaggacat cattcgcact tctattcagg gcctgtcagg caacggggag   1920
gtttacctcg accggatcga gatcattcca gtgaacccaa ccagggaggc tgaggaggat   1980
ctcgaggctg cgaagaaggc tgtggcctcg ctgttcacta ggacccggga cggcctccag   2040
gttaatgtga cggactacca ggtggatcag gctgccaacc tggtctcgtg cctctctgac   2100
gagcagtacg ctcacgataa aaagatgctc ctggaggccg tccgcgctgc taagaggctg   2160
tcgagggaga ggaacctcct gcaggaccca gatttcaaca ccattaattc tacggaggag   2220
aacgggtgga aggcgtcgaa tggcgtgacc atctctgagg gcgggccttt ctacaagggc   2280
cgcgctctcc agctggcttc agctagggag aactacccga catacatcta ccagaaggtc   2340
gacgcctccg agctgaagcc ctacacgcgc taccgcctcg atggcttcgt gaagtcatcc   2400
caggacctgg agatcgatct cattcaccat cacaaggtcc acctggttaa gaacgtgctg   2460
gacaatctcg tcagcgatac ctacccggac gattcttgct caggcatcaa tcgctgcgag   2520
gagcagcaga tggtgaacgc ccagctcgag accgagcatc accatccgat ggactgctgc   2580
gaggctgctc agacgcatga gttcagctcg tacatcgaca caggggatct gaactccact   2640
gtggaccagg gcatctgggt catcttcaag gtgcgcacta ccgatgggta cgcgacccct   2700
ggcaacctcg agctggtcga ggttgggccg ctcctgggcg agccactgga gagggagcag   2760
agggagaacg ctaagtggaa tgctgagctg ggcaggaagc gggctgagac cgaccgcgtc   2820
taccaggatg ctaagcagtc catcaatcac ctgttcgtgg actaccagga tcagcagctc   2880
aacccacaga ttggcatggc tgacatcatg gatgcccaga acctggtcgc gtccatcagc   2940
gacgtctact ctgatgccgt tctccagatc cctggcatta attacgagat ctacacagag   3000
ctgtcaaacc ggctccagca ggcctcctac ctgtacacta gccgcaacgc ggtgcagaat   3060
```

```
ggggacttca ataacggcct cgattcctgg aatgctacag ctggggctag cgtccagcag    3120
gacggcaaca ctcacttcct cgttctgtct cattgggatg cccaggtttc acagcagttc    3180
agggtgcagc cgaactgcaa gtatgtgctg agggttaccg ctgagaaggt tggcgggggc    3240
gacggctacg tgacgatcag ggatggcgct caccatacgg agacactgac tttcaacgcc    3300
tgcgactacg atatcaatgg cacctacgtc acggacaaca catacctcac taaggaggtc    3360
atattctaca gccacaccga gcatatgtgg gtggaggtca acgagacgga gggcgccttc    3420
cacatagact cgattgagtt cgtggagacc gagaagtga                          3459
```

<210> SEQ ID NO 10
<211> LENGTH: 3468
<212> TYPE: DNA
<213> ORGANISM: Artificial Sequence
<220> FEATURE:
<223> OTHER INFORMATION: Synthetic Cry Gene

<400> SEQUENCE: 10

```
atgaatagga ataaccagga cgagtacgag atcattgacg cttcgacttg cgggtgcagc      60
tcagacgatg ttgttcagta ccccctcgct cgcgatccca atgccgtgtt ccagaacatg     120
cactacaagg actacctcca gacatacgac ggcgattaca ctgggtcgct cattaaccca     180
aatctgtcta tcaatcctcg cgacgtcctg cagacgggaa tcaacattgt tgggaggctc     240
ctgggcttcc tcggggttcc gttcgctggc cagctggtga cattctacac tttcctcctg     300
aaccagctct ggcccaccaa cgacaatgcg gtctgggagg ccttcatggc gcagatcgag     360
gagctgatta ccagcgcat ctccgaggct gtggtcggca ccgctgctga tcacctcacg     420
gggctgcatg acaactacga gctttacgtg gaggctctcg aggagtggct ggagaggcca     480
aacgctgcta ggacgaacct cctgttcaat aggttcacca cgctcgactc cctgttcaca     540
cagttcatgc catcattcgg gactggcccc ggctcccaga actacgccgt ccctctcctg     600
accgtttacg cgcaggcggc taacctccac ctcctgctcc tgaaggacgc tgagatctac     660
ggcgctcgct gggggctgaa ccagaatcag atcaacagct tccacacaag gcagcaggag     720
cggacccagt actacacgaa tcattgcgtg acaacttaca caccggcct cgataggctg     780 agggggacca atacggagtc ctggctcaac taccataggt tccgcaggga gatgaccctg     840
atggcgatgg acctcgtggc gctgttcccg tactacaacg tccggcagta cccaaacggc     900
gctaatccac agctcacccg cgagatctac acggacccaa tcgtcttcaa cccaccagct     960
aatgttggcc tgtgcaggcg ctgggggaac aatccttaca tcgcttcag cgagctggag    1020 aacgccttca tcaggccacc tcacctgttc gatcggctca atacactgac tatttcgagg    1080
aaccggttcg acgtcggcag caatttcatc gagccgtggt cgggccatac gctgaggagg    1140
tcctacagca caattcaac agtgtacgag gattcctacg ccagattac cgctacgagg    1200 accacgatca cctccctgc caatggcaca gggcgggtgg agtctactgc tgtcgacttc    1260
cgctcagccc tggttggcat ctacggggtg aacagggcga gcttcatccc gggcggggtc    1320
ttcagcggca caactcagcc atcgaccggc gggtgcaggg acctctacga ttccagcgac    1380
gagctgccac cagacgagag cacgggctcg ttcgctcaca ggctctctca tgtcacattc    1440
ctgtcattca ccacgaacca ggctggctcg atcgccaatt ctgggagggt tccgacatac    1500
gtgtggactc accgggacgt ggatttcaac aataccatca acccaaatcg catcacgcag    1560
attcctgttg tgaaggcgta cgagctgtcc tccggcgcta ccgtcgttaa gggcccgggg    1620
```

```
ttcacgggcg gggacgtgat tcgcaggaca aacatcggcg ggttcggcgc tatcagggtc    1680
tccgttaccg gccccctgac gcagcgctac aggattcggt tccgctacgc ctccactatc    1740
gacttcgatt tcttcgtcac ccggggcggg acaactatca acaatttccg cttcacaagg    1800
actatgaaca ggggccagga gtcacggtac gagtcctacc gcaccgtgga gttcaccacg    1860
cccttcaact tcacgcagtc ccaggacatc attaggacat ccattcaggg cctcagcggc    1920
aacggggagg tttacctgga tcgcatcgag atcattccag tgaaccctac gagggaggct    1980
gaggaggacc tcgaggctgc gaagaaggct gtggctagcc tcttcaccag gacgagggat    2040
ggcctgcaag tgaatgtcac cgattaccag gtggaccagg ctgccaacct cgtctcttgc    2100
ctgtcagatg agcagtacgg ccacgacaag aagatgctcc tggaggccgt ccgcgctgct    2160
aagaggctgt ccagggagag gaacctcctg caggacccag atttcaacac aatcaatagc    2220
actgaggaga atggctggaa ggcgtccaac ggggtgacca tcagcgaggg cgggcctttc    2280
tacaagggcc gcgctctcca gctggcttcg gctagggaga attacccaac ttacatctac    2340
cagaaggtca acgcctctga gctgaagcct tacacgcgct accgcctgga tggcttcgtg    2400
aagtcatccc aggatctcga gatcgacctg attcaccatc acaaggtgca cctcgtcaag    2460
aacgttccgg acaatctggt cagcgatacg tactcggacg gctcgtgctc tgggatgaat    2520
cgctgcgagg agcagcagat ggtgaacgcg cagctcgaga cagagcatca ccatccgatg    2580
gactgctgcg aggccgcgca gactcatgag ttcagctcgt acattaatac cggcgatctg    2640
aactcttcag tcgaccaggg catctgggtg gtcctcaagg ttcgcacaac tgatggctac    2700
gccacgctgg gaacctcga gctggttgaa gtgggcccac tctccgggga gagcctggag    2760
agggagcaga gggacaacgc gaagtggtcc gctgagctgg caggaagcg ggctgagacc    2820
gatagggttt accaggacgc taagcagtcc atcaatcacc tcttcgtgga ttaccaggac    2880
cagcagctga acccggagat tggcatggct gatatcattg acgcccagaa cctcgtcgcg    2940
tcaatctccg atgtctacag cgacgccgtt ctgcagatcc ccggcattaa ttacgagatc    3000
tacacggagc tgtcgaacag gctgcagcag gcctcgtacc tctacacatc tcggaacgcg    3060
gtgcagaatg gcgatttcaa ctctgggctg gactcatgga atgctaccgg cggggctacg    3120
gtgcagcagg atggcaacac ccacttcctc gtcctgtccc attgggacgc tcaggtgagc    3180
cagcagttcc gggtccagcc gaactgcaag tatgtgctga gggtcactgc tgagaaggtt    3240
ggcgggggcg atggctacgt gaccatcagg gacggggctc accatacaga gaagctcact    3300
ttcaacgcct gcgactacga tatcaatggc acctacgtca cggacaacac atacctaact    3360
aaggaggttg tgttctactc gcacactgag catatgtggg tcgaggtttc tgagaccgag    3420
ggcgccttcc acatagactc aattgagttc gtggagaccg agaagtga                3468
```

<210> SEQ ID NO 11
<211> LENGTH: 3507
<212> TYPE: DNA
<213> ORGANISM: Artificial Sequence
<220> FEATURE:
<223> OTHER INFORMATION: Synthetic Cry Gene

<400> SEQUENCE: 11

```
atgaatagga ataaccagaa cgagtacgag gtcattgatg ctccccattg cggctgcccg     60
gcggacgatg ttgtgaagta cccactgacc gacgatccga acgccggcct gcagaacatg    120
aattacaagg agtacctcca gacctacggc ggggactaca ccgacccgct gatcaaccct    180
aatctctcgg tttctggcaa ggacgtgatt caggtcggaa tcaacattgt ggggcgcctc    240
```

```
ctgtccttct tcgggttccc attctccagc cagtgggtga cagtctacac ttacctcctg      300
aattcactgt ggcctgacga tgagaactcc gtttgggacg ccttcatgga gcgggtggag      360
gagctgatcg atcagaagat tagcgaggct gtcaagggcc gcgcgctcga cgatctgacc      420
gggctccagt acaactacaa cctctacgtg gaggcgctgg acgagtggct caacaggcca      480
aatggcgctc gggcctctct cgtgtcacag aggttcaaca tcctggattc cctcttcacc      540
cagttcatgc catccttcgg gagcggcccc gggagccaga attacgcgac gatcctcctg      600
cctgtgtacg ctcaggccgc gaacctgcac ctcctgctcc tgaaggacgc tgatatctac      660
ggcgccaggt gggggctcaa ccagacccag attgaccagt ccactctag gcagcagtca      720 ctcacccaga cgtacacaaa ccattgcgtg acagcctaca atgacggcct ggctgagctg      780 aggggggactt cggtcgcctc ttggctgaag taccaccagt accgcaggga gatgactgtc      840
accgcgatgg acctggttgc tctcttccca tactacaacg tgcgccagta cccgaacggc      900
gcgaatcccc agctcaccag ggaggtgtac acggacccaa tcgtcttcaa cccaccagag      960
aggccttctg gcgctttctg cgagtcattc tacaccatca gggctgctag ggagaggctg     1020
acgttctccc agctcgagca cgcgatcatt cgcccaccta ggctgttcga gcggttccag     1080
gctctcggca tctacacagg ggaggcccgc ctcaacgcta attccgcccc gatgaattac     1140
tggatcggcc atttcattag gaacacgagg ctggggggaca gcaccacgat cacaactaat     1200
tacggcacca cgaacaatag gctcaccaac ttctcaatgc cctccgacgt ctaccagatc     1260
aactccacgt cgtctaatct cgcggctatt ctgggcacac tctacggggt gactcgcgcc     1320
cagttccact tcggctcagg gtccttcagc acctacgtgg gccagaacag cgtcctgccg     1380
cagtgccatc agaactacaa tagcatcgag gagctgccaa accagtcgga cgagcctacc     1440
gttcgctcgt actctcacag gctgtcccat atcacgagct tcaacttcaa tgtgcagctg     1500
aacaatccgc tcatttctgc gggcaacatg cccgtttacg tgtggaccca caggtcagtc     1560
gacctgacga accggatctc atccgatcgc atcacccaga ttccggtggt caaggcttac     1620
gagctgtcct ccggcgctac agttgtgaag ggccccgggt tcactggcgg ggacgtgatc     1680
aggaggacga acacaggcgg gttcggcgcg attagggtct cggttaccgg gccgctcacg     1740
cagcgctacc gcatccgctt ccgctacgct tctaccattg acttcgattt cttcgtcacg     1800
cggggcggga caactatcaa caatttcagg ttcactcgga ccatgaacag gggccaggag     1860
tcgcggtacg agtcttaccg caccgtggag ttcaccacgc ccttcaactt cacacagtcc     1920
caggacatca ttcgcacttc aatccagggc ctgtccggca atggggaggt ctacctcgac     1980
cgcattgaga tcattccggt taaccccacg agggaggctg aggaggatct ggaggctgcg     2040
aagaaggcgg tggctagcct gttcacgagg acacgggacg gcctccaagt gaatgtcaag     2100
gactaccagg tcgatcaggc tgccaacctg gttagctgcc tctcggacga gcagtacggc     2160
tacgataaga agatgctcct ggaggccgtg cgcgctgcta agaggctctc gagggagagg     2220
aacctcctgc aggacccgga tttcaacaca atcaattcta ctgaggagaa cggctggaag     2280
gcttccaatg gggtgaccat tagcgagggc ggcccattct acaagggcag ggccctccag     2340
ctggcttcag ctcgggagaa ctacccaaca tacatctacc agaaggtcga cgccagcgag     2400
ctgaagcctt acactcgcta ccgcctcgat ggcttcgtga agtcttcaca ggacctggag     2460
atcgatctca ttcaccatca caaggttcac ctggtgaaga acgtccccgga caatctcgtc     2520 tccgatacgt accccgacga ttcatgctcc ggcatcaata ggtgccagga gcagcagatg     2580
```

| | |
|---|---:|
| gtgaacgccc agctggagac agagcatcac catccgatgg actgctgcga ggccgcgcag | 2640 |
| actcatgagt tctccagcta catcgacaca ggcgatctga acagcactgt ggaccagggg | 2700 |
| atctgggtca ttttcaaggt taggacaact gatggctacg cgaccctcgg gaacctcgag | 2760 |
| ctggttgaag tgggcccact cctgggggag cctctggaga gggagcagag ggagaacgcg | 2820 |
| aagtggaatg ctgagctggg caggaagcgg gctgagaccg accgcgtcta ccaggatgcc | 2880 |
| aagcagagca tcaatcacct gttcgttgac taccaggatc agcagctcaa cccagagatc | 2940 |
| ggcatggccg acattatgga tgcgcagaac ctggtcgcta gcatctcgga cgtttactcg | 3000 |
| gatgccgtgc tccagatccc tggcattaat tacgagatct acaccgagct gagcaacagg | 3060 |
| ctccagcagg cgagctacct gtacacgtcg cggaacgctg tgcagaatgg cgacttcaac | 3120 |
| aatgggctcg attcttggaa tgctaccgct ggcgcttcag tgcagcagga cgggaacacg | 3180 |
| cacttcctcg tcctgtcgca ttgggatgcc caggtttctc agcagttccg ggtgcagccg | 3240 |
| aactgcaagt atgtgctcag ggtgacagct gagaaagtgg gcgggggcga cggctacgtc | 3300 |
| actatccgcg acgatgccca ccatactgag accctgacgt tcaacgcgtg cgactacgat | 3360 |
| atcaatggca cctacgtcac ggacaacaca tacatcacta aggaggtcgt tttctactcc | 3420 |
| cacacagatc atatgtgggt cgaggttagc gagactgagg gcgccttcca catcgactcg | 3480 |
| cttgagttcg tggagaccga gaagtga | 3507 |

<210> SEQ ID NO 12
<211> LENGTH: 3471
<212> TYPE: DNA
<213> ORGANISM: Artificial Sequence
<220> FEATURE:
<223> OTHER INFORMATION: Synthetic Cry Gene

<400> SEQUENCE: 12

| | |
|---|---:|
| atgaatcaga acaagcacgg catcattggg gcctcgaact gcggctgcgc ctccgacgat | 60 |
| gtggctaagt accctctcgc taacaaccct tactccagcg ccctgaacct caattcctgc | 120 |
| cagaactcgt ctatcctcaa ttggattaac atcattgggg acgccgcgaa ggaggctgtc | 180 |
| agcatcggca ccacgattgt ttcactgatc acggccccgt ccctgacagg cctcatcagc | 240 |
| attgtgtacg acctcatcgg gaaggtcatc ggcgggtcat ccggccagag catttcggac | 300 |
| ctgtcgatct gcgatctcct gtctatcatt gacctcaggg tgtctcagtc agtcctgaac | 360 |
| gacgggatcg ccgatttcaa tggctcagtg ctcctgtacc gcaactacct ggaggcgctc | 420 |
| gactcctgga acaagaatcc caactccgct agcgctgagg agctgaggac caggttcagg | 480 |
| attgccgact ccgagttcga tcgcatcctc actcgcggct cactgaccaa tggcggctcc | 540 |
| ctcgcccgcc agaacgctca gatcctcctg ctccctagct tcgcgtcggc tgccttcttc | 600 |
| cacctgctcc tgctcaggga cgctacgcgc tacggaacca actggggcct ctacaatgct | 660 |
| actccgttca taaactacca gtccaagctg gtcgagctga tcgagctgta caccgactac | 720 |
| tgcgttcact ggtacaatag ggggttcaac gagctgaggc agaggggcac gagcgctaca | 780 |
| gcttggctgg agttccatcg ctaccgcagg gagatgacgc tcatggttct ggacatcgtg | 840 |
| gccagcttca gctcgctcga tattactaac taccctatcg agaccgactt ccagctgtcg | 900 |
| cgcgtgattt acaccgaccc gatcgggttc gtccaccgct cttcactgag gggcgagtct | 960 |
| tggttctcat tcgtcaatag ggcgaacttc tcggacctcg agaatgctat cccgaacccc | 1020 |
| cggccatctt ggttcctgaa caatatgatc atttccactg cagcctgac cctccccgtt | 1080 |
| tcgccatcta cggatcgcgc gagggtgtgg tacggctcac gggaccgcat ctcaccggct | 1140 |

```
aactcccagt tcattacaga gctgatctct ggccagcaca caactgctac acagactatt   1200
ctgggccgga atatcttccg cgtggacagc caggcctgca atctcaacga taccacgtac   1260
ggcgtcaaca gggctgtttt ctaccatgac gcctcggagg gctctcagcg ctcagtctac   1320
gagggataca tcaggacaac tggcatcgat aatcctcggg tgcagaatat aaacacgtac   1380
ctcccgggcg agaacagcga catccctacg ccggaggatt acacacacat tctgtcgacc   1440
acaatcaacc tcaccggcgg gctgaggcag gtcgcttcta acaggcgctc cagcctcgtt   1500
atgtacggct ggactcataa gtcactggcg cgcaacaaca caatcaaccc tgataggatc   1560
actcagattc cgctcaccaa ggtggacact aggggggaccg gcgtgtcgta cgtcaacgat   1620
cccggcttca tcggcggggc cctgctccag cgcaccgacc acggctccct cggggttctg   1680
cgggtgcagt tcccactgca tctccgccag cagtacagga ttcgggtccg ctacgcgtcc   1740
acaactaaca tccgcctcag cgtgaatggg tcgttcggca cgatctccca gaacctgccc   1800
agcacaatga ggctcgggga ggacctgcgc tacggctcct tcgccattcg ggagttcaac   1860
acgagcatcc gccccacagc gtcgccagat cagattaggc tcactatcga gccaagcttc   1920
atcaggcagg aggtctacgt tgaccggatc gagttcattc ctgtcaaccc gacgagggag   1980
gctaaggagg atctggaggc tgctaagaag gctgtggcta gcctcttcac caggacgagg   2040
gacggcctgc aagtgaatgt caaggactac caggttgatc aggccgcgaa cctcgtgtcc   2100
tgcctgagcg acgagcagta cggctacgat aagaagatgc tgctcgaggc ggtcagggct   2160
gctaagaggc tctccaggga gaggaacctg ctccaggacc ctgatttcaa tacgatcaac   2220
agcacagagg agaacgggtg gaaggcgtct aatggcgtga ccatttcaga gggcggccca   2280
ttctacaagg gcagggctat ccagctggct tcggctcggg agaactaccc cacgtacatc   2340
taccagaagg tcgacgcctc tgagctgaag ccatacacac gctaccgcct ggatggcttc   2400
gtgaagtcgt ctcaggacct cgagatcgat ctgattcacc atcacaaggt ccacctggtt   2460
aagaatgtgc ccgacaacct ggtcctcgac acctacccag acgattcctg caatggcatc   2520
aacaggtgcg acgagcagaa gatggtgaac gcccagctcg agaccgagca tcaccatccg   2580
atggactgct gcgaggcggc tcagacgcac gagttctcat cctacattaa cacaggggac   2640
ctgaatgcca gcgtggatca gggcatctgg gtggtcctca aagtcaggac cacggacggg   2700
tacgctacgc tgggcaacct ggagctggtt gaagtgggc cactctcggg cgagtctctg   2760
gagagggagc agagggacaa cgccaagtgg agcgctgagc tgggcaggaa gagggctgag   2820
accgagaggg tctactacgc cgcgaagcag tcgatcaatc acctcttcgt ggactacagg   2880
gatcagcagc tgaaccccca gattggcatg gctgacatca tggatgccca gaacctcgtc   2940
gcgtcaatct ccgacgtgta ctccgatgcg gtcctgcaga tcccaggcat caactacgag   3000
atctacacgg agctgagcaa ccggctgcag caggcctcgt acctccacat gtctcgcaat   3060
gcgatgcaga cgggggactt caattctggc ctggattcat ggaatgcgac tgctgggcc   3120
accgttcagc aggacggcaa cacccactc ctggtgctct cccattggga tgcccaagtt   3180
agccagcagt tccgcgtgca gccgaactgc aagtacgtcc tgagggttac tgctgagaag   3240
gtcggcgggg gcgacggcta cgttaccatc cgcgatggcg ctcaccatac agagactctc   3300
accttcaacg cctgcgacta cgatatcaat ggcacgtacg tgacagacaa cacttacctg   3360
accaaggagg ttgtgttcca cccggagacc cagcatatgt gggtcgaggt tagcgagacg   3420
gagggcgtgt tccacctgga cagcgttgag ttcatggaga cccagcagta g            3471
```

<210> SEQ ID NO 13
<211> LENGTH: 3471
<212> TYPE: DNA
<213> ORGANISM: Artificial Sequence
<220> FEATURE:
<223> OTHER INFORMATION: Synthetic Cry Gene

<400> SEQUENCE: 13

```
atgaatcaga acaagcacgg catcattggg gcctcgaact gcggctgcgc ctccgacgat      60
gtggctaagt accctctcgc taacaaccct tactccagcg ccctgaacct caattcctgc     120
cagaactcgt ctatcctcaa ttggattaac atcattgggg acgccgcgaa ggaggctgtc     180
agcatcggca ccacgattgt tcactgatca cggccccgt ccctgacagg cctcatcagc      240
attgtgtacg acctcatcgg aaggtcatc ggcgggtcat ccggccagag catttcggac      300
ctgtcgatct gcgatctcct gtctatcatt gacctcaggg tgtctcagtc agtcctgaac     360
gacgggatcg ccgatttcaa tggctcagtg ctcctgtacc gcaactacct ggaggcgctc     420
gactcctgga acaagaatcc caactccgct agcgctgagg agctgaggac caggttcagg     480
attgccgact ccgagttcga tcgcatcctc actcgcggct cactgaccaa tggcggctcc     540
ctcgcccgcc agaacgctca gatcctcctg ctccctagct tcgcgtcggc tgccttcttc     600
cacctgctcc tgctcaggga cgctacgcgc tacggaacca actggggcct ctacaatgct     660
actccgttca taaactacca gtccaagctg gtcgagctga tcgagctgta caccgactac     720
tgcgttcact ggtacaatag ggggttcaac gagctgaggc agaggggcac gagcgctaca     780
gcttggctgg agttccatcg ctaccgcagg gagatgacgc tcatggttct ggacatcgtg     840
gccagcttca gctcgctcga tattactaac taccctatcg agaccgactt ccagctgtcg     900
cgcgtgattt acaccgaccc gatcgggttc gtccaccgct cttcactgag gggcgagtct     960
tggttctcat tcgtcaatag ggcgaacttc tcggacctcg agaatgctat cccgaacccc    1020
cggccatctt ggttcctgaa caatatgatc atttccactg gcagcctgac cctccccgtt    1080
tcgccatcta cggatcgcgc gagggtgtgg tacggctcac gggaccgcat ctcaccggct    1140
aactcccagt tcattacaga gctgatctct ggccagcaca caactgctac acagactatt    1200
ctgggccgga atatcttccg cgtggacagc caggcctgca atctcaacga taccacgtac    1260
ggcgtcaaca gggctgtttt ctaccatgac gcctcggagg ctctcagcg ctcagtctac    1320
gagggataca tcaggacaac tggcatcgat aatcctcggg tgcagaatat taacacgtac    1380
ctcccgggcg agaacagcga catccctacg ccggaggatt acacacacat tctgtcgacc    1440
acaatcaacc tcaccggcgg gctgaggcag gtcgcttcta caggcgctc cagcctcgtt    1500
atgtacggct ggactcataa gtcactggcg cgcaacaaca caatcaaccc tgataggatc    1560
actcagattc cgctcaccaa ggtggacact aggggaccg gcgtgtcgta cgtcaacgat    1620
cccggcttca tcggcggggc cctgctccag cgcaccgacc acggctccct cggggttctg    1680
cgggtgcagt tcccactgca tctccgccag cagtacagga ttcgggtccg ctacgcgtcc    1740
acaactaaca tccgcctcag cgtgaatggg tcgttcggca cgatctccca gaacctgccc    1800
agcacaatga ggctcgggga ggacctgcgc tacggctcct tcgccattcg ggagttcaac    1860
acgagcatcc gccccacagc gtcgccagat cagattaggc tcactatcga gccaagcttc    1920
atcaggcagg aggtctacgt tgaccggatc gagttcattc ctgtcaaccc gacgagggag    1980
gctaaggagg atctggaggc tgctaagaag gctgtggcta gcctcttcac caggacgagg    2040
gacggcctgc aagtgaatgt caaggactac caggttgatc aggccgcgaa cctcgtgtcc    2100
```

-continued

```
tgcctgagcg acgagcagta cggctacgat aagaagatgc tgctcgaggc ggtcagggct    2160
gctaagaggc tctccaggga gaggaacctg ctccaggacc ctgatttcaa tacgatcaac    2220
agcacagagg agaacggggtg gaaggcgtct aatggcgtga ccatttcaga gggcggccca   2280
ttctacaagg gcagggctat ccagctggct tcggctcggg agaactaccc cacgtacatc    2340
taccagaagg tcgacgcctc tgagctgaag ccatacacac gctaccgcct ggatggcttc    2400
gtgaagtcgt ctcaggacct cgagatcgat ctgattcacc atcacaaggt ccacctggtt    2460
aagaatgtgc ccgacaacct ggtcctcgac acctacccag acgattcctg caatggcatc    2520
aacaggtgcg acgagcagaa gatggtgaac gcccagctcg agaccggaca tcaccatccg    2580
atggactgct gcgaggcggc tcagacgcac gagttctcat cctacattaa cacaggggac    2640
ctgaatgcca gcgtggatca gggcatctgg gtggtcctca agtcaggac cacggacggg     2700 tacgctacgc tgggcaacct ggagctggtt gaagtggggc cactctcggg cgagtctctg    2760
gagagggagc agagggacaa cgccaagtgg agcgctgagc tgggcaggaa gagggctgag    2820
accgagaggg tctactacgc cgcgaagcag tcgatcaatc acctcttcgt ggactaccaa    2880
gatcagcagc tgaaccccca gattggcatg gctgacatca tggatgccca gaacctcgtc    2940
gcgtcaatct ccgacgtgta ctccgatgcg gtcctgcaga tcccaggcat caactacgag    3000
atctacacgg agctgagcaa ccggctgcag caggcctcgt acctccacac gtctcgcaat    3060
gcgatgcaga acggggactt caattctggc ctggattcat ggaatgcgac tgctggggcc    3120
accgttcagc aggacggcaa cacccacttc ctggtgctct cccattggga tgcccaagtt    3180
agccagcagt tccgcgtgca gccgaactgc aagtacgtcc tgagggttac tgctgagaag    3240
gtcggcgggg gcgacggcta cgttaccatc cgcgatggcg ctcaccatac agagactctc    3300
accttcaacg cctgcgacta cgatatcaat ggcacgtacg tgacagacaa cacttacctg    3360
accaaggagg ttgtgttcca cccggagacc cagcatatgt gggtcgaggt tagcgagacg    3420
gagggcgtgt tccacctgga cagcgttgag ttcatggaga cccagcagta g             3471
```

<210> SEQ ID NO 14
<211> LENGTH: 5919
<212> TYPE: DNA
<213> ORGANISM: Artificial Sequence
<220> FEATURE:
<223> OTHER INFORMATION: Synthetic Cry Gene

<400> SEQUENCE: 14

```
atggacctgg atgggaataa gacagagaca gagaccgaga ttgtgaatgg gagcgagagc     60
agcattgacc cgagcagcgt ttcgtacgct gggaacaata gctactccag cgccctgaac    120
ctcaattcgt gccagaatag gggcatcgct cagtgggtta acacgctggg cggggctatt    180
gggcaggccg tgagcatcgg cacatctatc atttcactcc tggccgcgcc gacactcact    240
gggtctattt cactggcctt caatctcatc aggaggatgg ggaccggctc caacggctcg    300
tctatttccg acctgagcat ctgcgatctc ctgagcatca ttaacctgcg ggtttcgcag    360
gctgtgctca cgacgggat cgctgatttc aatggctccg ttgctgtgta cgacctgtac    420
ctccacgccc tgcgcagctg gaacaataac cctaacgctg ctactgctga ggagctgagg    480
acccgcttca ggatcgccga ttcggagttc gagaggattc tgacgagggg ctcgctcaca    540
catgcgggct ccctcgcccg ccaggacgct caggtcctcc tgctcccgtc cttcgttaac    600
gcggcttacc tgcacctgct catcctccgc gatgcttcgc gctacggggc ctcttgggc    660
```

```
ctcttcaaca ccacgccgca tatcaattac cccgtgaggc tgcagcagct cattggcagc    720
tacacgcact actgcacaca ttggtacaac caggggctga atgagatccg gcagcgcggc    780
aacactgccg tgaattggct cgagttccac cgctaccgcc gcgacatgac gctgatggtc    840
ctcgatgtgg tctcgctgtt ctctgccctc gacacgatcc gctacccgaa cgctacagtt    900
gtgcagctca gccgcactgt ctacaccgat ccgattggct tcgttaaccg cgggtcaggc    960
aataggctgt cctggttcga ctggaggaac caggcgaatt tctctactct cgagtcagag   1020
atgccgaccc cctcatcccc actgagcctc aaccacatgt cgatcttcac tgggcctctg   1080
accctcccag tgtcccctaa cacgcatagg gcccgggtct ggtacggcaa ccagaatatg   1140
ttcacaactg ggtcacagaa ctccggccag accacgaact ctattcagaa tatctcaggc   1200
ctggagattt tccgcatcga ctctcaggcg tgcaatctca ataacaattc atacggcgtg   1260
aacagggcgg agttcttcca cggggctagc cagggctcgc agcggtctgt ctaccaggga   1320
tacatccgcc agagcggcct ggacaaccct gtcgttatga atctgcagtc tttcctccca   1380
ggcgagaact cagccacccc tacggcgcag gattacaccc acattctgtc caacccggtt   1440
aatatcaggg gcgggctcag gcagattgtg gccgacaggc gctcctccgt ggtcgtttac   1500
ggctggacgc acaagtccct gagcaggagg tcactcgtgg ctccagacca gatcacccag   1560
gtcccagccg ttaaggcgtc cccttcttca cattgcacta tcattgccgg cccaggcttc   1620
accggcgggg acctggtgtc gctccagccc aacggccagc tcgtcatccc gttccaggtt   1680
tctgcgcccg agacgaacta ccacattcgc atctgctacg tctcgacgtc tgattgcagc   1740
attaacacaa tctgcaatga cgagacgcat ctgtccacac tcccgagcac aacttccagc   1800
ctggagaacc tccagtgcaa tcacctgcat tacttcaacg tgggcacttt caagccaacc   1860
atcgactcga agctgacgct cgtcaacaca tctcctaacg ctaacatcat tatcgacaag   1920
atcgagttca tcccggtgga taccgcccag cagcagaacg aggacctcga ggccgcgaag   1980
aaggctgtcg cctccctgtt cacacgcact agggacggcc tccaggtcaa tgttaaggac   2040
taccaggtgg atcaggctgc caacctggtc tcatgcctct ccgacgagca gtacggctac   2100
gataagaaga tgctgctcga ggccgtgagg gctgctaaga ggctgagcag ggagaggaac   2160
ctgctccagg accccgattt caacacaatc aactcgaccg aggagaacgg gtggaaggcg   2220
tcaaatggcg tcaccatctc cgagggcggg ccattctaca agggcagggc tattcagctc   2280
gcgtctgctc gggagaacta ccccacatac atctaccaga aggtggatgc ctccgagctg   2340
aagccataca cccgctaccg cctcgacggc ttcgtcaagt cgtctcagga cctggagatt   2400
gatctcatcc accatcacaa ggtgcacctg gtcaagaacg ttccggacaa tctcgtgagc   2460
atgaacagga acaacccaaa cgagtacgag attattgatg ctccatactg cggctgcccc   2520
tccgatgacg atgtgcgcta cccctcgcc agcgacccga cgccgcgtt ccagaatatg   2580 aactacaagg agtacctgca gacctacgac ggcgattaca cggggtcact gattaatcca   2640
aacctctcca tcaatcctcg cgacgtcctc cagaccggaa tcaacattgt tggccgcatc   2700
ctcggcttcc tgggcgtgcc gttcgctggc cagctggtta ccttctacac gttcctcctg   2760
aaccagctct ggcctacgaa tgacaacgcg gtgtgggagg ccttcatggc gcagatcgag   2820
gagctgattg atcagaagat ctccgctcag gtggtcagga acgccctcga cgatctgacc   2880
ggcctccacg actactacga ggagtacctg gctgctctcg aggagtggct cgagaggcca   2940
aacgcgcctc gcgctaatct ggtcacgcag cgcttcgaga acctccatac cgccttcgtg   3000
acgaggatgc cgagcttcgg gacaggcccc gggtcgcaga gggacgcggt tgctctcctg   3060
```

```
actgtgtacg cgcaggcggc taacctgcac ctcctgctcc tgaaggatgc tgagatctac    3120
ggcgctcggt gggggctgca gcagggccag atcaacctct acttcaatgc ccagcaggag    3180
cgcacaagga tctacactaa ccactgcgtt gagacctaca ataggggct cgaggacgtg     3240 cggggcacga acacagagag ctggctgaat taccatcgct tccgcaggga gatgacgctc    3300
atggcgatgg acctcgtggc gctcttcccc tactacaacg tccgccagta cccaaatggc    3360
gccaaccctc agctgacaag ggagatctac actgacccga tcgtgtacaa cccaccagct    3420
aatcagggga tctgcaggcg ctggggcaac aatccctaca acaccttctc tgagctggag    3480
aatgcgttca ttaggccacc tcacctcttc gaccgcctga acaggctcac catctcccgg    3540
aatcgctaca cggctccaac cacgaactcg tacctggatt actggtctgg ccataccctc    3600
cagtcacagt acgcgaacaa tcctacaact tacgagacgt cctacggcca gattacaagc    3660
aacactcgcc tcttcaatac cacgaacggc gctaatgcta tcgacagcag ggcccggaac    3720
ttcgggaatc tgtacgcgaa tctctacggc gtctccagcc tgaacatttt cccaaccggc    3780
gttatgtcag agatcaccte cgcccctaac acgtgctggc aggacctcac aactaccgag    3840
gagctgccac tggtgaacaa taacttcaat ctcctgtccc acgtcacatt cctgaggttc    3900
aacacgacac agggcggccc actcgcgact gttggcttcg tgcccaccta cgtgtggacg    3960
cggcaggacg tcgatttcaa taacatcatt acaccaaacc gcatcactca gattcctgtt    4020
gtgaaggcgt acgagctgtc gtctggcgct acagtcgtta agggcccggg gttcactggc    4080
ggggacgtca ttaggaggac taacaccggc gggttcgggg ctatcagggt gagcgtcaca    4140
ggccccctca ctcagcgcta caggattcgg ttccgctacg cgtcgaccat cgacttcgat    4200
ttcttcgtca cgcgcggcgg gactaccatc aataacttcc ggttcacgcg caccatgaac    4260
aggggccagg agagccggta cgagtcgtac cgcaccgtgg agttcacgac accgttcaac    4320
ttcacacaga gccaggacat cattcgcact tctattcagg gcctgtcagg caacggggag    4380
gtttacctcg accggatcga gatcattcca gtgaacccaa ccagggaggc tgaggaggat    4440
ctcgaggctg cgaagaaggc tgtggcctcg ctgttcacta ggacccggga cggcctccag    4500
gttaatgtga cggactacca ggtggatcag gctgccaacc tggtctcgtg cctctctgac    4560
gagcagtacg ctcacgataa gaagatgctc ctggaggccg tccgcgctgc taagaggctg    4620
tcgagggaga ggaacctcct gcaggaccca gatttcaaca ccattaattc tacggaggag    4680
aacgggtgga aggcgtcgaa tggcgtgacc atctctgagg gcgggccttt ctacaagggc    4740
cgcgctctcc agctggcttc agctagggag aactacccga catacatcta ccagaaggtc    4800
gacgcctccg agctgaagcc ctacacgcgc taccgcctcg atggcttcgt gaagtcatcc    4860
caggacctgg agatcgatct cattcaccat cacaaggtcc acctggttaa gaacgtgctg    4920
gacaatctcg tcagcgatac ctacccggac gattcttgct caggcatcaa tcgctgcgag    4980
gagcagcaga tggtgaacgc ccagctcgag accgagcatc accatccgat ggactgctgc    5040
gaggctgctc agacgcatga gttcagctcg tacatcgaca caggggatct gaactccact    5100
gtggaccagg gcatctgggt catcttcaag gtgcgcacta ccgatgggta cgcgaccctc    5160
ggcaacctcg agctggtcga ggttgggccg ctcctgggcg agccactgga gagggagcag    5220
agggagaacg ctaagtggaa tgctgagctg gcaggaagc gggctgagac cgaccgcgtc     5280
taccaggatg ctaagcagtc catcaatcac ctgttcgtgg actaccagga tcagcagctc    5340
aacccacaga ttggcatggc tgacatcatg gatgcccaga acctggtcgc gtccatcagc    5400
```

| | |
|---|---|
| gacgtctact ctgatgccgt tctccagatc cctggcatta attacgagat ctacacagag | 5460 |
| ctgtcaaacc ggctccagca ggcctcctac ctgtacacta gccgcaacgc ggtgcagaat | 5520 |
| ggggacttca ataacggcct cgattcctgg aatgctacag ctggggctag cgtccagcag | 5580 |
| gacggcaaca ctcacttcct cgttctgtct cattgggatg cccaggtttc acagcagttc | 5640 |
| agggtgcagc cgaactgcaa gtatgtgctg agggttaccg ctgagaaggt tggcgggggc | 5700 |
| gacggctacg tgacgatcag ggatggcgct caccatacgg agacactgac tttcaacgcc | 5760 |
| tgcgactacg atatcaatgg cacctacgtc acggacaaca catacctcac taaggaggtc | 5820 |
| ctcttctaca gccacaccga gcatatgtgg gtggaggtca acgagacgga gggcgccttc | 5880 |
| cacctcgact cgattgagtt cgtggagacc gagaagtga | 5919 |

<210> SEQ ID NO 15
<211> LENGTH: 3468
<212> TYPE: DNA
<213> ORGANISM: Artificial Sequence
<220> FEATURE:
<223> OTHER INFORMATION: Synthetic Cry Gene

<400> SEQUENCE: 15

| | |
|---|---|
| atgaatagga ataaccagga cgagtacgag atcattgacg cttcgacttg cgggtgcagc | 60 |
| tcagacgatg ttgttcagta ccccctcgct cgcgatccca atgccgtgtt ccagaacatg | 120 |
| cactacaagg actacctcca gacatacgac ggcgattaca ctgggtcgct cattaaccca | 180 |
| aatctgtcta tcaatcctcg cgacgtcctg cagacgggaa tcaacattgt tgggaggctc | 240 |
| ctgggcttcc tcggggttcc gttcgctggc cagctggtga cattctacac tttcctcctg | 300 |
| aaccagctct ggcccaccaa cgacaatgcg gtctgggagg ccttcatggc gcagatcgag | 360 |
| gagctgatta accagcgcat ctccgaggct gtggtcggca ccgctgctga tcacctcacg | 420 |
| gggctgcatg acaactacga gctttacgtg gaggctctcg aggagtggct ggagaggcca | 480 |
| aacgctgcta ggacgaacct cctgttcaat aggttcacca cgctcgactc cctgttcaca | 540 |
| cagttcatgc catcattcgg gactggcccc ggctcccaga actacgccgt ccctctcctg | 600 |
| accgtttacg cgcaggcggc taacctccac ctcctgctcc tgaaggacgc tgagatctac | 660 |
| ggcgctcgct gggggctgaa ccagaatcag atcaacagct ccacacaag gcagcaggag | 720 |
| cggacccagt actacacgaa tcattgcgtg acaacttaca acaccggcct cgataggctg | 780 |
| aggggggacca atacggagtc ctggctcaac taccataggt tccgcaggga gatgaccctg | 840 |
| atggcgatgg acctcgtggc gctgttcccg tactacaacg tccggcagta cccaaacggc | 900 |
| gctaatccac agctcacccg cgagatctac acggacccaa tcgtcttcaa cccaccagct | 960 |
| aatgttggcc tgtgcaggcg ctgggggaac atccttaca atcgcttcag cgagctggag | 1020 |
| aacgccttca tcaggccacc tcacctgttc gatcggctca atacactgac tatttcgagg | 1080 |
| aaccggttcg acgtcggcag caatttcatc gagccgtggt cgggccatac gctgaggagg | 1140 |
| tcctacagca caaattcaac agtgtacgag gattcctacg ccagattac cgctacgagg | 1200 |
| accacgatca acctccctgc caatggcaca gggcgggtgg agtctactgc tgtcgacttc | 1260 |
| cgctcagccc tggttggcat ctacgggtg aacaggcga gcttcatccc gggcggggtc | 1320 |
| ttcagcggca caactcagcc atcgaccggc gggtgcaggg acctctacga ttccagcgac | 1380 |
| gagctgccac cagacgagag cacgggctcg ttcgctcaca ggctctctca tgtcacattc | 1440 |
| ctgtcattca ccacgaacca ggctggctcg atcgccaatt ctgggagggt tccgacatac | 1500 |
| gtgtggactc accgggacgt ggatttcaac aataccatca acccaaatcg catcacgcag | 1560 |

| | | |
|---|---|---|
| attcctgttg tgaaggcgta cgagctgtcc tccggcgcta ccgtcgttaa gggcccgggg | 1620 |
| ttcacgggcg gggacgtgat tcgcaggaca aacatcggcg ggttcggcgc tatcagggtc | 1680 |
| tccgttaccg gccccctgac gcagcgctac aggattcggt tccgctacgc ctccactatc | 1740 |
| gacttcgatt tcttcgtcac ccggggcggg acaactatca acaatttccg cttcacaagg | 1800 |
| actatgaaca ggggccagga gtcacggtac gagtcctacc gcaccgtgga gttcaccacg | 1860 |
| cccttcaact tcacgcagtc ccaggacatc attaggacat ccattcaggg cctcagcggc | 1920 |
| aacgggagg tttacctgga tcgcatcgag atcattccag tgaaccctac gagggaggct | 1980 |
| gaggaggacc tcgaggctgc gaagaaggct gtggctagcc tcttcaccag gacgagggat | 2040 |
| ggcctgcaag tgaatgtcac cgattaccag gtggaccagg ctgccaacct cgtctcttgc | 2100 |
| ctgtcagatg agcagtacgg ccacgacaag aagatgctcc tggaggccgt ccgcgctgct | 2160 |
| aagaggctgt ccagggagag gaacctcctg caggacccag atttcaacac aatcaatagc | 2220 |
| actgaggaga atggctggaa ggcgtccaac ggggtgacca tcagcgaggg cgggcctttc | 2280 |
| tacaagggcc gcgctctcca gctggcttcg gctagggaga attacccaac ttacatctac | 2340 |
| cagaaggtca cgcctctga gctgaagcct tacgcgcgct accgcctgga tggcttcgtg | 2400 |
| aagtcatccc aggatctcga gatcgacctg attcaccatc acaaggtgca cctcgtcaag | 2460 |
| aacgttccgg acaatctggt cagcgatacg tactcggacg gctcgtgctc tgggatgaat | 2520 |
| cgctgcgagg agcagcagat ggtgaacgcg cagctcgaga cagagcatca ccatccgatg | 2580 |
| gactgctgcg aggccgcgca gactcatgag ttcagctcgt acattaatac cggcgatctg | 2640 |
| aactcttcag tcgaccaggg catctgggtg gtcctcaagg ttcgcacaac tgatggctac | 2700 |
| gccacgctgg ggaacctcga gctggttgaa gtgggcccac tctccgggga gagcctggag | 2760 |
| agggagcaga gggacaacgc gaagtggtcc gctgagctgg gcaggaagcg ggctgagacc | 2820 |
| gataggtt accaggacgc taagcagtcc atcaatcacc tcttcgtgga ttaccaggac | 2880 |
| cagcagctga acccggagat tggcatggct gatatcattg acgcccagaa cctcgtcgcg | 2940 |
| tcaatctccg atgtctacag cgacgccgtt ctgcagatcc ccggcattaa ttacgagatc | 3000 |
| tacacggagc tgtcgaacag gctgcagcag gcctcgtacc tctacacatc tcggaacgcg | 3060 |
| gtgcagaatg gcgatttcaa ctctgggctg gactcatgga atgctaccgg cggggctacg | 3120 |
| gtgcagcagg atggcaacac ccacttcctc gtcctgtccc attgggacgc tcaggtgagc | 3180 |
| cagcagttcc gggtccagcc gaactgcaag tatgtgctga gggtcactgc tgagaaggtt | 3240 |
| ggcggggcg atggctacgt gaccatcagg gacggggctc accatacaga gaagctcact | 3300 |
| ttcaacgcct gcgactacga tatcaatggc acctacgtca cggacaacac atacatcact | 3360 |
| aaggaggttg tgttctactc gcacactgag catatgtggg tcgaggtttc tgagaccgag | 3420 |
| ggcgccttcc acctcgactc aattgagttc gtggagaccg agaagtga | 3468 |

<210> SEQ ID NO 16
<211> LENGTH: 1168
<212> TYPE: PRT
<213> ORGANISM: Bacillus thuringiensis

<400> SEQUENCE: 16

Met Asn Arg Asn Asn Gln Asn Glu Tyr Glu Val Ile Asp Ala Pro His
1               5                   10                  15

Cys Gly Cys Pro Ala Asp Asp Val Val Lys Tyr Pro Leu Thr Asp Asp
            20                  25                  30

```
Pro Asn Ala Gly Leu Gln Asn Met Asn Tyr Lys Glu Tyr Leu Gln Thr
            35                  40                  45

Tyr Gly Gly Asp Tyr Thr Asp Pro Leu Ile Asn Pro Asn Leu Ser Val
 50                  55                  60

Ser Gly Lys Asp Val Ile Gln Val Gly Ile Asn Ile Val Gly Arg Leu
 65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
            100                 105                 110

Asp Ala Phe Met Glu Arg Val Glu Glu Leu Ile Asp Gln Lys Ile Ser
            115                 120                 125

Glu Ala Val Lys Gly Arg Ala Leu Asp Asp Leu Thr Gly Leu Gln Tyr
            130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190

Gln Asn Tyr Ala Thr Ile Leu Leu Pro Val Tyr Ala Gln Ala Ala Asn
            195                 200                 205

Leu His Leu Leu Leu Leu Lys Asp Ala Asp Ile Tyr Gly Ala Arg Trp
            210                 215                 220

Gly Leu Asn Gln Thr Gln Ile Asp Gln Phe His Ser Arg Gln Gln Ser
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Ser Val Ala Ser Trp Leu Lys Tyr His
            260                 265                 270

Gln Tyr Arg Arg Glu Met Thr Val Thr Ala Met Asp Leu Val Ala Leu
            275                 280                 285

Phe Pro Tyr Tyr Asn Val Arg Gln Tyr Pro Asn Gly Ala Asn Pro Gln
290                 295                 300

Leu Thr Arg Glu Val Tyr Thr Asp Pro Ile Val Phe Asn Pro Pro Glu
305                 310                 315                 320

Arg Pro Ser Gly Ala Phe Cys Glu Ser Phe Tyr Thr Ile Arg Ala Ala
                325                 330                 335

Arg Glu Arg Leu Thr Phe Ser Gln Leu Glu His Ala Ile Ile Arg Pro
            340                 345                 350

Pro Arg Leu Phe Glu Arg Phe Gln Ala Leu Gly Ile Tyr Thr Gly Glu
            355                 360                 365

Ala Arg Leu Asn Ala Asn Ser Ala Pro Met Asn Tyr Trp Ile Gly His
370                 375                 380

Phe Ile Arg Asn Thr Arg Leu Gly Asp Ser Thr Thr Ile Thr Thr Asn
385                 390                 395                 400

Tyr Gly Thr Thr Asn Asn Arg Leu Thr Asn Phe Ser Met Pro Ser Asp
                405                 410                 415

Val Tyr Gln Ile Asn Ser Thr Ser Asn Leu Ala Ala Ile Leu Gly
            420                 425                 430

Thr Leu Tyr Gly Val Thr Arg Ala Gln Phe His Phe Gly Ser Gly Ser
            435                 440                 445

Phe Ser Thr Tyr Val Gly Gln Asn Ser Val Leu Pro Gln Cys His Gln
```

```
            450                 455                 460
Asn Tyr Asn Ser Ile Glu Glu Leu Pro Asn Gln Ser Asp Glu Pro Thr
465                 470                 475                 480

Val Arg Ser Tyr Ser His Arg Leu Ser His Ile Thr Ser Phe Asn Phe
                    485                 490                 495

Asn Val Gln Leu Asn Asn Pro Leu Ile Ser Ala Gly Asn Met Pro Val
                500                 505                 510

Tyr Val Trp Thr His Arg Ser Val Asp Leu Thr Asn Arg Ile Ser Ser
            515                 520                 525

Asp Arg Ile Thr Gln Ile Pro Val Val Lys Ala Tyr Glu Leu Ser Ser
        530                 535                 540

Gly Ala Thr Val Val Lys Gly Pro Gly Phe Thr Gly Asp Val Ile
545                 550                 555                 560

Arg Arg Thr Asn Thr Gly Gly Phe Gly Ala Ile Arg Val Ser Val Thr
                    565                 570                 575

Gly Pro Leu Thr Gln Arg Tyr Arg Ile Arg Phe Arg Tyr Ala Ser Thr
                580                 585                 590

Ile Asp Phe Asp Phe Phe Val Thr Arg Gly Gly Thr Thr Ile Asn Asn
            595                 600                 605

Phe Arg Phe Thr Arg Thr Met Asn Arg Gly Gln Glu Ser Arg Tyr Glu
        610                 615                 620

Ser Tyr Arg Thr Val Glu Phe Thr Thr Pro Phe Asn Phe Thr Gln Ser
625                 630                 635                 640

Gln Asp Ile Ile Arg Thr Ser Ile Gln Gly Leu Ser Gly Asn Gly Glu
                    645                 650                 655

Val Tyr Leu Asp Arg Ile Glu Ile Ile Pro Val Asn Pro Thr Arg Glu
                660                 665                 670

Ala Glu Glu Asp Leu Glu Ala Ala Lys Lys Ala Val Ala Ser Leu Phe
            675                 680                 685

Thr Arg Thr Arg Asp Gly Leu Gln Val Asn Val Lys Asp Tyr Gln Val
        690                 695                 700

Asp Gln Ala Ala Asn Leu Val Ser Cys Leu Ser Asp Glu Gln Tyr Gly
705                 710                 715                 720

Tyr Asp Lys Lys Met Leu Leu Glu Ala Val Arg Ala Ala Lys Arg Leu
                    725                 730                 735

Ser Arg Glu Arg Asn Leu Leu Gln Asp Pro Asp Phe Asn Thr Ile Asn
                740                 745                 750

Ser Thr Glu Glu Asn Gly Trp Lys Ala Ser Asn Gly Val Thr Ile Ser
            755                 760                 765

Glu Gly Gly Pro Phe Tyr Lys Gly Arg Ala Leu Gln Leu Ala Ser Ala
        770                 775                 780

Arg Glu Asn Tyr Pro Thr Tyr Ile Tyr Gln Lys Val Asp Ala Ser Glu
785                 790                 795                 800

Leu Lys Pro Tyr Thr Arg Tyr Arg Leu Asp Gly Phe Val Lys Ser Ser
                    805                 810                 815

Gln Asp Leu Glu Ile Asp Leu Ile His His Lys Val His Leu Val
                820                 825                 830

Lys Asn Val Pro Asp Asn Leu Val Ser Asp Thr Tyr Pro Asp Asp Ser
            835                 840                 845

Cys Ser Gly Ile Asn Arg Cys Gln Glu Gln Gln Met Val Asn Ala Gln
        850                 855                 860

Leu Glu Thr Glu His His His Pro Met Asp Cys Cys Glu Ala Ala Gln
865                 870                 875                 880
```

Thr His Glu Phe Ser Ser Tyr Ile Asp Thr Gly Asp Leu Asn Ser Thr
              885                 890                 895

Val Asp Gln Gly Ile Trp Val Ile Phe Lys Val Arg Thr Thr Asp Gly
              900                 905                 910

Tyr Ala Thr Leu Gly Asn Leu Glu Leu Val Glu Val Gly Pro Leu Leu
              915                 920                 925

Gly Glu Pro Leu Glu Arg Glu Gln Arg Glu Asn Ala Lys Trp Asn Ala
       930                 935                 940

Glu Leu Gly Arg Lys Arg Ala Glu Thr Asp Arg Val Tyr Gln Asp Ala
945                 950                 955                 960

Lys Gln Ser Ile Asn His Leu Phe Val Asp Tyr Gln Asp Gln Gln Leu
              965                 970                 975

Asn Pro Glu Ile Gly Met Ala Asp Ile Met Asp Ala Gln Asn Leu Val
              980                 985                 990

Ala Ser Ile Ser Asp Val Tyr Ser Asp Ala Val Leu Gln Ile Pro Gly
              995                 1000                1005

Ile Asn Tyr Glu Ile Tyr Thr Glu Leu Ser Asn Arg Leu Gln Gln
       1010                1015                1020

Ala Ser Tyr Leu Tyr Thr Ser Arg Asn Ala Val Gln Asn Gly Asp
       1025                1030                1035

Phe Asn Asn Gly Leu Asp Ser Trp Asn Ala Thr Ala Gly Ala Ser
       1040                1045                1050

Val Gln Gln Asp Gly Asn Thr His Phe Leu Val Leu Ser His Trp
       1055                1060                1065

Asp Ala Gln Val Ser Gln Gln Phe Arg Val Gln Pro Asn Cys Lys
       1070                1075                1080

Tyr Val Leu Arg Val Thr Ala Glu Lys Val Gly Gly Gly Asp Gly
       1085                1090                1095

Tyr Val Thr Ile Arg Asp Asp Ala His His Thr Glu Thr Leu Thr
       1100                1105                1110

Phe Asn Ala Cys Asp Tyr Asp Ile Asn Gly Thr Tyr Val Thr Asp
       1115                1120                1125

Asn Thr Tyr Leu Thr Lys Glu Val Val Phe Tyr Ser His Thr Asp
       1130                1135                1140

His Met Trp Val Glu Val Ser Glu Thr Glu Gly Ala Phe His Ile
       1145                1150                1155

Asp Ser Ile Glu Phe Val Glu Thr Glu Lys
       1160                1165

<210> SEQ ID NO 17
<211> LENGTH: 1156
<212> TYPE: PRT
<213> ORGANISM: Bacillus thuringiensis

<400> SEQUENCE: 17

Met Asn Gln Asn Lys His Gly Ile Ile Gly Ala Ser Asn Cys Gly Cys
1               5                   10                  15

Ala Ser Asp Asp Val Ala Lys Tyr Pro Leu Ala Asn Asn Pro Tyr Ser
              20                  25                  30

Ser Ala Leu Asn Leu Asn Ser Cys Gln Asn Ser Ser Ile Leu Asn Trp
         35                  40                  45

Ile Asn Ile Ile Gly Asp Ala Ala Lys Glu Ala Val Ser Ile Gly Thr
     50                  55                  60

Thr Ile Val Ser Leu Ile Thr Ala Pro Ser Leu Thr Gly Leu Ile Ser

-continued

```
                65                  70                  75                  80
        Ile Val Tyr Asp Leu Ile Gly Lys Val Leu Gly Gly Ser Ser Gly Gln
                        85                  90                  95
        Ser Ile Ser Asp Leu Ser Ile Cys Asp Leu Ser Ile Ile Asp Leu
                       100                 105                 110
        Arg Val Ser Gln Ser Val Leu Asn Asp Gly Ile Ala Asp Phe Asn Gly
                       115                 120                 125
        Ser Val Leu Leu Tyr Arg Asn Tyr Leu Glu Ala Leu Asp Ser Trp Asn
                       130                 135                 140
        Lys Asn Pro Asn Ser Ala Ser Ala Glu Glu Leu Arg Thr Arg Phe Arg
        145                 150                 155                 160
        Ile Ala Asp Ser Glu Phe Asp Arg Ile Leu Thr Arg Gly Ser Leu Thr
                               165                 170                 175
        Asn Gly Gly Ser Leu Ala Arg Gln Asn Ala Gln Ile Leu Leu Leu Pro
                       180                 185                 190
        Ser Phe Ala Ser Ala Ala Phe Phe His Leu Leu Leu Arg Asp Ala
                       195                 200                 205
        Thr Arg Tyr Gly Thr Asn Trp Gly Leu Tyr Asn Ala Thr Pro Phe Ile
                210                 215                 220
        Asn Tyr Gln Ser Lys Leu Val Glu Leu Ile Glu Leu Tyr Thr Asp Tyr
        225                 230                 235                 240
        Cys Val His Trp Tyr Asn Arg Gly Phe Asn Glu Leu Arg Gln Arg Gly
                               245                 250                 255
        Thr Ser Ala Thr Ala Trp Leu Glu Phe His Arg Tyr Arg Arg Glu Met
                       260                 265                 270
        Thr Leu Met Val Leu Asp Ile Val Ala Ser Phe Ser Ser Leu Asp Ile
                       275                 280                 285
        Thr Asn Tyr Pro Ile Glu Thr Asp Phe Gln Leu Ser Arg Val Ile Tyr
                       290                 295                 300
        Thr Asp Pro Ile Gly Phe Val His Arg Ser Ser Leu Arg Gly Glu Ser
        305                 310                 315                 320
        Trp Phe Ser Phe Val Asn Arg Ala Asn Phe Ser Asp Leu Glu Asn Ala
                               325                 330                 335
        Ile Pro Asn Pro Arg Pro Ser Trp Phe Leu Asn Asn Met Ile Ile Ser
                       340                 345                 350
        Thr Gly Ser Leu Thr Leu Pro Val Ser Pro Ser Thr Asp Arg Ala Arg
                       355                 360                 365
        Val Trp Tyr Gly Ser Arg Asp Arg Ile Ser Pro Ala Asn Ser Gln Phe
                370                 375                 380
        Ile Thr Glu Leu Ile Ser Gly Gln His Thr Thr Ala Thr Gln Thr Ile
        385                 390                 395                 400
        Leu Gly Arg Asn Ile Phe Arg Val Asp Ser Gln Ala Cys Asn Leu Asn
                               405                 410                 415
        Asp Thr Thr Tyr Gly Val Asn Arg Ala Val Phe Tyr His Asp Ala Ser
                       420                 425                 430
        Glu Gly Ser Gln Arg Ser Val Tyr Glu Gly Tyr Ile Arg Thr Thr Gly
                       435                 440                 445
        Ile Asp Asn Pro Arg Val Gln Asn Ile Asn Thr Tyr Leu Pro Gly Glu
                       450                 455                 460
        Asn Ser Asp Ile Pro Thr Pro Glu Asp Tyr Thr His Ile Leu Ser Thr
        465                 470                 475                 480
        Thr Ile Asn Leu Thr Gly Gly Leu Arg Gln Val Ala Ser Asn Arg Arg
                               485                 490                 495
```

```
Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
            515                 520                 525

Asp Thr Arg Gly Thr Gly Val Ser Tyr Val Asn Asp Pro Gly Phe Ile
530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
            595                 600                 605

Leu Arg Tyr Gly Ser Phe Ala Ile Arg Glu Phe Asn Thr Ser Ile Arg
            610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
            660                 665                 670

Ala Ser Leu Phe Thr Arg Thr Arg Asp Gly Leu Gln Val Asn Val Lys
            675                 680                 685

Asp Tyr Gln Val Asp Gln Ala Ala Asn Leu Val Ser Cys Leu Ser Asp
            690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Ile Gln
            755                 760                 765

Leu Ala Ser Ala Arg Glu Asn Tyr Pro Thr Tyr Ile Tyr Gln Lys Val
            770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Val Pro Asp Asn Leu Val Leu Asp Thr Tyr
            820                 825                 830

Pro Asp Asp Ser Cys Asn Gly Ile Asn Arg Cys Asp Glu Gln Lys Met
            835                 840                 845

Val Asn Ala Gln Leu Glu Thr Glu His His Pro Met Asp Cys Cys
            850                 855                 860

Glu Ala Ala Gln Thr His Glu Phe Ser Ser Tyr Ile Asn Thr Gly Asp
865                 870                 875                 880

Leu Asn Ala Ser Val Asp Gln Gly Ile Trp Val Val Leu Lys Val Arg
                885                 890                 895

Thr Thr Asp Gly Tyr Ala Thr Leu Gly Asn Leu Glu Leu Val Glu Val
            900                 905                 910
```

Gly Pro Leu Ser Gly Glu Ser Leu Glu Arg Glu Gln Arg Asp Asn Ala
    915                 920                 925

Lys Trp Ser Ala Glu Leu Gly Arg Lys Arg Ala Glu Thr Glu Arg Val
930                 935                 940

Tyr Tyr Ala Ala Lys Gln Ser Ile Asn His Leu Phe Val Asp Tyr Arg
945                 950                 955                 960

Asp Gln Gln Leu Asn Pro Gln Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
        995                 1000                1005

Leu Gln Gln Ala Ser Tyr Leu His Met Ser Arg Asn Ala Met Gln
    1010                1015                1020

Asn Gly Asp Phe Asn Ser Gly Leu Asp Ser Trp Asn Ala Thr Ala
    1025                1030                1035

Gly Ala Thr Val Gln Gln Asp Gly Asn Thr His Phe Leu Val Leu
    1040                1045                1050

Ser His Trp Asp Ala Gln Val Ser Gln Gln Phe Arg Val Gln Pro
    1055                1060                1065

Asn Cys Lys Tyr Val Leu Arg Val Thr Ala Glu Lys Val Gly Gly
    1070                1075                1080

Gly Asp Gly Tyr Val Thr Ile Arg Asp Gly Ala His His Thr Glu
    1085                1090                1095

Thr Leu Thr Phe Asn Ala Cys Asp Tyr Asp Ile Asn Gly Thr Tyr
    1100                1105                1110

Val Thr Asp Asn Thr Tyr Leu Thr Lys Glu Val Val Phe His Pro
    1115                1120                1125

Glu Thr Gln His Met Trp Val Glu Val Ser Glu Thr Glu Gly Val
    1130                1135                1140

Phe His Ile Asp Ser Val Glu Phe Met Glu Thr Gln Gln
    1145                1150                1155

<210> SEQ ID NO 18
<211> LENGTH: 1156
<212> TYPE: PRT
<213> ORGANISM: Bacillus thuringiensis

<400> SEQUENCE: 18

Met Asn Gln Asn Lys His Gly Ile Ile Gly Ala Ser Asn Cys Gly Cys
1               5                   10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

```
Ser Val Leu Leu Tyr Arg Asn Tyr Leu Glu Ala Leu Asp Ser Trp Asn
    130                 135                 140
Lys Asn Pro Asn Ser Ala Ser Ala Glu Glu Leu Arg Thr Arg Phe Arg
145                 150                 155                 160
Ile Ala Asp Ser Glu Phe Asp Arg Ile Leu Thr Arg Gly Ser Leu Thr
                165                 170                 175
Asn Gly Gly Ser Leu Ala Arg Gln Asn Ala Gln Ile Leu Leu Leu Pro
            180                 185                 190
Ser Phe Ala Ser Ala Ala Phe Phe His Leu Leu Leu Arg Asp Ala
        195                 200                 205
Thr Arg Tyr Gly Thr Asn Trp Gly Leu Tyr Asn Ala Thr Pro Phe Ile
    210                 215                 220
Asn Tyr Gln Ser Lys Leu Val Glu Leu Ile Glu Leu Tyr Thr Asp Tyr
225                 230                 235                 240
Cys Val His Trp Tyr Asn Arg Gly Phe Asn Glu Leu Arg Gln Arg Gly
                245                 250                 255
Thr Ser Ala Thr Ala Trp Leu Glu Phe His Arg Tyr Arg Arg Glu Met
            260                 265                 270
Thr Leu Met Val Leu Asp Ile Val Ala Ser Phe Ser Ser Leu Asp Ile
        275                 280                 285
Thr Asn Tyr Pro Ile Glu Thr Asp Phe Gln Leu Ser Arg Val Ile Tyr
    290                 295                 300
Thr Asp Pro Ile Gly Phe Val His Arg Ser Ser Leu Arg Gly Glu Ser
305                 310                 315                 320
Trp Phe Ser Phe Val Asn Arg Ala Asn Phe Ser Asp Leu Glu Asn Ala
                325                 330                 335
Ile Pro Asn Pro Arg Pro Ser Trp Phe Leu Asn Asn Met Ile Ile Ser
            340                 345                 350
Thr Gly Ser Leu Thr Leu Pro Val Ser Pro Ser Thr Asp Arg Ala Arg
        355                 360                 365
Val Trp Tyr Gly Ser Arg Asp Arg Ile Ser Pro Ala Asn Ser Gln Phe
    370                 375                 380
Ile Thr Glu Leu Ile Ser Gly Gln His Thr Thr Ala Thr Gln Thr Ile
385                 390                 395                 400
Leu Gly Arg Asn Ile Phe Arg Val Asp Ser Gln Ala Cys Asn Leu Asn
                405                 410                 415
Asp Thr Thr Tyr Gly Val Asn Arg Ala Val Phe Tyr His Asp Ala Ser
            420                 425                 430
Glu Gly Ser Gln Arg Ser Val Tyr Glu Gly Tyr Ile Arg Thr Thr Gly
        435                 440                 445
Ile Asp Asn Pro Arg Val Gln Asn Ile Asn Thr Tyr Leu Pro Gly Glu
    450                 455                 460
Asn Ser Asp Ile Pro Thr Pro Glu Asp Tyr Thr His Ile Leu Ser Thr
465                 470                 475                 480
Thr Ile Asn Leu Thr Gly Gly Leu Arg Gln Val Ala Ser Asn Arg Arg
                485                 490                 495
Ser Ser Leu Val Met Tyr Gly Trp Thr His Lys Ser Leu Ala Arg Asn
            500                 505                 510
Asn Thr Ile Asn Pro Asp Arg Ile Thr Gln Ile Pro Leu Thr Lys Val
        515                 520                 525
Asp Thr Arg Gly Thr Gly Val Ser Tyr Val Asn Asp Pro Gly Phe Ile
    530                 535                 540
```

```
Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
                580                 585                 590

Gly Thr Ile Ser Gln Asn Leu Pro Ser Thr Met Arg Leu Gly Glu Asp
                595                 600                 605

Leu Arg Tyr Gly Ser Phe Ala Ile Arg Glu Phe Asn Thr Ser Ile Arg
610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
                660                 665                 670

Ala Ser Leu Phe Thr Arg Thr Arg Asp Gly Leu Gln Val Asn Val Lys
                675                 680                 685

Asp Tyr Gln Val Asp Gln Ala Ala Asn Leu Val Ser Cys Leu Ser Asp
690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
                740                 745                 750

Val Thr Ile Ser Glu Gly Gly Pro Phe Tyr Lys Gly Arg Ala Ile Gln
                755                 760                 765

Leu Ala Ser Ala Arg Glu Asn Tyr Pro Thr Tyr Ile Tyr Gln Lys Val
770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His Lys
                805                 810                 815

Val His Leu Val Lys Asn Val Pro Asp Asn Leu Val Leu Asp Thr Tyr
                820                 825                 830

Pro Asp Asp Ser Cys Asn Gly Ile Asn Arg Cys Asp Glu Gln Lys Met
                835                 840                 845

Val Asn Ala Gln Leu Glu Thr Gly His His Pro Met Asp Cys Cys
850                 855                 860

Glu Ala Ala Gln Thr His Glu Phe Ser Ser Tyr Ile Asn Thr Gly Asp
865                 870                 875                 880

Leu Asn Ala Ser Val Asp Gln Gly Ile Trp Val Val Leu Lys Val Arg
                885                 890                 895

Thr Thr Asp Gly Tyr Ala Thr Leu Gly Asn Leu Glu Leu Val Glu Val
                900                 905                 910

Gly Pro Leu Ser Gly Glu Ser Leu Arg Glu Gln Arg Asp Asn Ala
                915                 920                 925

Lys Trp Ser Ala Glu Leu Gly Arg Lys Arg Ala Glu Thr Glu Arg Val
                930                 935                 940

Tyr Tyr Ala Ala Lys Gln Ser Ile Asn His Leu Phe Val Asp Tyr Gln
945                 950                 955                 960

Asp Gln Gln Leu Asn Pro Gln Ile Gly Met Ala Asp Ile Met Asp Ala
```

```
              965                 970                 975
Gln Asn Leu Val Ala Ser Ile Ser Asp Val Tyr Ser Asp Ala Val Leu
                980                 985                 990

Gln Ile Pro Gly Ile Asn Tyr Glu Ile Tyr Thr Glu Leu Ser Asn Arg
            995                1000                1005

Leu Gln Gln Ala Ser Tyr Leu His Thr Ser Arg Asn Ala Met Gln
       1010                1015                1020

Asn Gly Asp Phe Asn Ser Gly Leu Asp Ser Trp Asn Ala Thr Ala
   1025                1030                1035

Gly Ala Thr Val Gln Gln Asp Gly Asn Thr His Phe Leu Val Leu
1040                1045                1050

Ser His Trp Asp Ala Gln Val Ser Gln Gln Phe Arg Val Gln Pro
    1055                1060                1065

Asn Cys Lys Tyr Val Leu Arg Val Thr Ala Glu Lys Val Gly Gly
        1070                1075                1080

Gly Asp Gly Tyr Val Thr Ile Arg Asp Gly Ala His His Thr Glu
    1085                1090                1095

Thr Leu Thr Phe Asn Ala Cys Asp Tyr Asp Ile Asn Gly Thr Tyr
    1100                1105                1110

Val Thr Asp Asn Thr Tyr Leu Thr Lys Glu Val Val Phe His Pro
    1115                1120                1125

Glu Thr Gln His Met Trp Val Glu Val Ser Glu Thr Glu Gly Val
    1130                1135                1140

Phe His Ile Asp Ser Val Glu Phe Met Glu Thr Gln Gln
    1145                1150                1155

<210> SEQ ID NO 19
<211> LENGTH: 1152
<212> TYPE: PRT
<213> ORGANISM: Bacillus thuringiensis

<400> SEQUENCE: 19

Met Asn Arg Asn Asn Pro Asn Glu Tyr Glu Ile Ile Asp Ala Pro Tyr
1               5                  10                  15

Cys Gly Cys Pro Ser Asp Asp Val Arg Tyr Pro Leu Ala Ser Asp
            20                  25                  30

Pro Asn Ala Ala Phe Gln Asn Met Asn Tyr Lys Glu Tyr Leu Gln Thr
        35                  40                  45

Tyr Asp Gly Asp Tyr Thr Gly Ser Leu Ile Asn Pro Asn Leu Ser Ile
    50                  55                  60

Asn Pro Arg Asp Val Leu Gln Thr Gly Ile Asn Ile Val Gly Arg Ile
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
        115                 120                 125

Ala Gln Val Val Arg Asn Ala Leu Asp Asp Leu Thr Gly Leu His Asp
    130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
                165                 170                 175
```

```
Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
            195                 200                 205

Leu His Leu Leu Leu Leu Lys Asp Ala Glu Ile Tyr Gly Ala Arg Trp
            210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
            245                 250                 255

Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
            275                 280                 285

Phe Pro Tyr Tyr Asn Val Arg Gln Tyr Pro Asn Gly Ala Asn Pro Gln
            290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
            325                 330                 335

Ser Glu Leu Glu Asn Ala Phe Ile Arg Pro Pro His Leu Phe Asp Arg
            340                 345                 350

Leu Asn Arg Leu Thr Ile Ser Arg Asn Arg Tyr Thr Ala Pro Thr Thr
            355                 360                 365

Asn Ser Tyr Leu Asp Tyr Trp Ser Gly His Thr Leu Gln Ser Gln Tyr
            370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Asn Ala Ile Asp Ser
            405                 410                 415

Arg Ala Arg Asn Phe Gly Asn Leu Tyr Ala Asn Leu Tyr Gly Val Ser
            420                 425                 430

Ser Leu Asn Ile Phe Pro Thr Gly Val Met Ser Glu Ile Thr Ser Ala
            435                 440                 445

Pro Asn Thr Cys Trp Gln Asp Leu Thr Thr Thr Glu Glu Leu Pro Leu
450                 455                 460

Val Asn Asn Asn Phe Asn Leu Leu Ser His Val Thr Phe Leu Arg Phe
465                 470                 475                 480

Asn Thr Thr Gln Gly Gly Pro Leu Ala Thr Val Gly Phe Val Pro Thr
            485                 490                 495

Tyr Val Trp Thr Arg Gln Asp Val Asp Phe Asn Asn Ile Ile Thr Pro
            500                 505                 510

Asn Arg Ile Thr Gln Ile Pro Val Val Lys Ala Tyr Glu Leu Ser Ser
            515                 520                 525

Gly Ala Thr Val Val Lys Gly Pro Gly Phe Thr Gly Gly Asp Val Ile
            530                 535                 540

Arg Arg Thr Asn Thr Gly Gly Phe Gly Ala Ile Arg Val Ser Val Thr
545                 550                 555                 560

Gly Pro Leu Thr Gln Arg Tyr Arg Ile Arg Phe Arg Tyr Ala Ser Thr
            565                 570                 575

Ile Asp Phe Asp Phe Phe Val Thr Arg Gly Gly Thr Thr Ile Asn Asn
            580                 585                 590

Phe Arg Phe Thr Arg Thr Met Asn Arg Gly Gln Glu Ser Arg Tyr Glu
```

-continued

```
                595                 600                 605
Ser Tyr Arg Thr Val Glu Phe Thr Thr Pro Phe Asn Phe Thr Gln Ser
610                 615                 620

Gln Asp Ile Ile Arg Thr Ser Ile Gln Gly Leu Ser Gly Asn Gly Glu
625                 630                 635                 640

Val Tyr Leu Asp Arg Ile Glu Ile Ile Pro Val Asn Pro Thr Arg Glu
                645                 650                 655

Ala Glu Glu Asp Leu Glu Ala Ala Lys Lys Ala Val Ala Ser Leu Phe
                660                 665                 670

Thr Arg Thr Arg Asp Gly Leu Gln Val Asn Val Thr Asp Tyr Gln Val
                675                 680                 685

Asp Gln Ala Ala Asn Leu Val Ser Cys Leu Ser Asp Glu Gln Tyr Ala
                690                 695                 700

His Asp Lys Lys Met Leu Leu Glu Ala Val Arg Ala Ala Lys Arg Leu
705                 710                 715                 720

Ser Arg Glu Arg Asn Leu Leu Gln Asp Pro Asp Phe Asn Thr Ile Asn
                725                 730                 735

Ser Thr Glu Glu Asn Gly Trp Lys Ala Ser Asn Gly Val Thr Ile Ser
                740                 745                 750

Glu Gly Gly Pro Phe Tyr Lys Gly Arg Ala Leu Gln Leu Ala Ser Ala
                755                 760                 765

Arg Glu Asn Tyr Pro Thr Tyr Ile Tyr Gln Lys Val Asp Ala Ser Glu
770                 775                 780

Leu Lys Pro Tyr Thr Arg Tyr Arg Leu Asp Gly Phe Val Lys Ser Ser
785                 790                 795                 800

Gln Asp Leu Glu Ile Asp Leu Ile His His Lys Val His Leu Val
                805                 810                 815

Lys Asn Val Leu Asp Asn Leu Val Ser Asp Thr Tyr Pro Asp Asp Ser
                820                 825                 830

Cys Ser Gly Ile Asn Arg Cys Glu Glu Gln Gln Met Val Asn Ala Gln
                835                 840                 845

Leu Glu Thr Glu His His Pro Met Asp Cys Cys Glu Ala Ala Gln
                850                 855                 860

Thr His Glu Phe Ser Ser Tyr Ile Asp Thr Gly Asp Leu Asn Ser Thr
865                 870                 875                 880

Val Asp Gln Gly Ile Trp Val Ile Phe Lys Val Arg Thr Thr Asp Gly
                885                 890                 895

Tyr Ala Thr Leu Gly Asn Leu Glu Leu Val Glu Val Gly Pro Leu Leu
                900                 905                 910

Gly Glu Pro Leu Glu Arg Glu Gln Arg Glu Asn Ala Lys Trp Asn Ala
                915                 920                 925

Glu Leu Gly Arg Lys Arg Ala Glu Thr Asp Arg Val Tyr Gln Asp Ala
930                 935                 940

Lys Gln Ser Ile Asn His Leu Phe Val Asp Tyr Gln Asp Gln Leu
945                 950                 955                 960

Asn Pro Gln Ile Gly Met Ala Asp Ile Met Asp Ala Gln Asn Leu Val
                965                 970                 975

Ala Ser Ile Ser Asp Val Tyr Ser Asp Ala Val Leu Gln Ile Pro Gly
                980                 985                 990

Ile Asn Tyr Glu Ile Tyr Thr Glu Leu Ser Asn Arg Leu Gln Gln Ala
                995                 1000                1005

Ser Tyr Leu Tyr Thr Ser Arg Asn Ala Val Gln Asn Gly Asp Phe
                1010                1015                1020
```

```
Asn Asn Gly Leu Asp Ser Trp Asn Ala Thr Ala Gly Ala Ser Val
    1025            1030                1035

Gln Gln Asp Gly Asn Thr His Phe Leu Val Leu Ser His Trp Asp
    1040            1045                1050

Ala Gln Val Ser Gln Gln Phe Arg Val Gln Pro Asn Cys Lys Tyr
    1055            1060                1065

Val Leu Arg Val Thr Ala Glu Lys Val Gly Gly Gly Asp Gly Tyr
    1070            1075                1080

Val Thr Ile Arg Asp Gly Ala His His Thr Glu Thr Leu Thr Phe
    1085            1090                1095

Asn Ala Cys Asp Tyr Asp Ile Asn Gly Thr Tyr Val Thr Asp Asn
    1100            1105                1110

Thr Tyr Leu Thr Lys Glu Val Ile Phe Tyr Ser His Thr Glu His
    1115            1120                1125

Met Trp Val Glu Val Asn Glu Thr Glu Gly Ala Phe His Ile Asp
    1130            1135                1140

Ser Ile Glu Phe Val Glu Thr Glu Lys
    1145            1150
```

<210> SEQ ID NO 20
<211> LENGTH: 1155
<212> TYPE: PRT
<213> ORGANISM: Bacillus thuringiensis

<400> SEQUENCE: 20

```
Met Asn Arg Asn Asn Gln Asp Glu Tyr Glu Ile Ile Asp Ala Ser Thr
1               5                   10                  15

Cys Gly Cys Ser Ser Asp Asp Val Val Gln Tyr Pro Leu Ala Arg Asp
            20                  25                  30

Pro Asn Ala Val Phe Gln Asn Met His Tyr Lys Asp Tyr Leu Gln Thr
        35                  40                  45

Tyr Asp Gly Asp Tyr Thr Gly Ser Leu Ile Asn Pro Asn Leu Ser Ile
    50                  55                  60

Asn Pro Arg Asp Val Leu Gln Thr Gly Ile Asn Ile Val Gly Arg Leu
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asn Gln Arg Ile Ser
        115                 120                 125

Glu Ala Val Val Gly Thr Ala Ala Asp His Leu Thr Gly Leu His Asp
    130                 135                 140

Asn Tyr Glu Leu Tyr Val Glu Ala Leu Glu Glu Trp Leu Glu Arg Pro
145                 150                 155                 160

Asn Ala Ala Arg Thr Asn Leu Leu Phe Asn Arg Phe Thr Thr Leu Asp
                165                 170                 175

Ser Leu Phe Thr Gln Phe Met Pro Ser Phe Gly Thr Gly Pro Gly Ser
            180                 185                 190

Gln Asn Tyr Ala Val Pro Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Asn Gln Asn Gln Ile Asn Ser Phe His Thr Arg Gln Gln Glu
```

```
              225                 230                 235                 240
        Arg Thr Gln Tyr Tyr Thr Asn His Cys Val Thr Thr Tyr Asn Thr Gly
                        245                 250                 255

Leu Asp Arg Leu Arg Gly Thr Asn Thr Glu Ser Trp Leu Asn Tyr His
                        260                 265                 270

Arg Phe Arg Arg Glu Met Thr Leu Met Ala Met Asp Leu Val Ala Leu
                        275                 280                 285

Phe Pro Tyr Tyr Asn Val Arg Gln Tyr Pro Asn Gly Ala Asn Pro Gln
                        290                 295                 300

Leu Thr Arg Glu Ile Tyr Thr Asp Pro Ile Val Phe Asn Pro Pro Ala
        305                 310                 315                 320

Asn Val Gly Leu Cys Arg Arg Trp Gly Asn Asn Pro Tyr Asn Arg Phe
                        325                 330                 335

Ser Glu Leu Glu Asn Ala Phe Ile Arg Pro Pro His Leu Phe Asp Arg
                        340                 345                 350

Leu Asn Thr Leu Thr Ile Ser Arg Asn Arg Phe Asp Val Gly Ser Asn
                        355                 360                 365

Phe Ile Glu Pro Trp Ser Gly His Thr Leu Arg Arg Ser Tyr Ser Asn
                        370                 375                 380

Asn Ser Thr Val Tyr Glu Asp Ser Tyr Gly Gln Ile Thr Ala Thr Arg
        385                 390                 395                 400

Thr Thr Ile Asn Leu Pro Ala Asn Gly Thr Gly Arg Val Glu Ser Thr
                        405                 410                 415

Ala Val Asp Phe Arg Ser Ala Leu Val Gly Ile Tyr Gly Val Asn Arg
                        420                 425                 430

Ala Ser Phe Ile Pro Gly Gly Val Phe Ser Gly Thr Thr Gln Pro Ser
                        435                 440                 445

Thr Gly Gly Cys Arg Asp Leu Tyr Asp Ser Ser Asp Glu Leu Pro Pro
        450                 455                 460

Asp Glu Ser Thr Gly Ser Phe Ala His Arg Leu Ser His Val Thr Phe
        465                 470                 475                 480

Leu Ser Phe Thr Thr Asn Gln Ala Gly Ser Ile Ala Asn Ser Gly Arg
                        485                 490                 495

Val Pro Thr Tyr Val Trp Thr His Arg Asp Val Asp Phe Asn Asn Thr
                        500                 505                 510

Ile Asn Pro Asn Arg Ile Thr Gln Ile Pro Val Val Lys Ala Tyr Glu
                        515                 520                 525

Leu Ser Ser Gly Ala Thr Val Val Lys Gly Pro Gly Phe Thr Gly Gly
        530                 535                 540

Asp Val Ile Arg Arg Thr Asn Ile Gly Gly Phe Gly Ala Ile Arg Val
        545                 550                 555                 560

Ser Val Thr Gly Pro Leu Thr Gln Arg Tyr Arg Ile Arg Phe Arg Tyr
                        565                 570                 575

Ala Ser Thr Ile Asp Phe Asp Phe Phe Val Thr Arg Gly Gly Thr Thr
                        580                 585                 590

Ile Asn Asn Phe Arg Phe Thr Arg Thr Met Asn Arg Gly Gln Glu Ser
                        595                 600                 605

Arg Tyr Glu Ser Tyr Arg Thr Val Glu Phe Thr Pro Phe Asn Phe
                        610                 615                 620

Thr Gln Ser Gln Asp Ile Ile Arg Thr Ser Ile Gln Gly Leu Ser Gly
        625                 630                 635                 640

Asn Gly Glu Val Tyr Leu Asp Arg Ile Glu Ile Pro Val Asn Pro
                        645                 650                 655
```

```
Thr Arg Glu Ala Glu Glu Asp Leu Glu Ala Ala Lys Lys Ala Val Ala
        660                 665                 670

Ser Leu Phe Thr Arg Thr Arg Asp Gly Leu Gln Val Asn Val Thr Asp
        675                 680                 685

Tyr Gln Val Asp Gln Ala Ala Asn Leu Val Ser Cys Leu Ser Asp Glu
        690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
                725                 730                 735

Thr Ile Asn Ser Thr Glu Glu Asn Gly Trp Lys Ala Ser Asn Gly Val
        740                 745                 750

Thr Ile Ser Glu Gly Gly Pro Phe Tyr Lys Gly Arg Ala Leu Gln Leu
        755                 760                 765

Ala Ser Ala Arg Glu Asn Tyr Pro Thr Tyr Ile Tyr Gln Lys Val Asn
        770                 775                 780

Ala Ser Glu Leu Lys Pro Tyr Thr Arg Tyr Arg Leu Asp Gly Phe Val
785                 790                 795                 800

Lys Ser Ser Gln Asp Leu Glu Ile Asp Leu Ile His His His Lys Val
                805                 810                 815

His Leu Val Lys Asn Val Pro Asp Asn Leu Val Ser Asp Thr Tyr Ser
                820                 825                 830

Asp Gly Ser Cys Ser Gly Met Asn Arg Cys Glu Glu Gln Gln Met Val
                835                 840                 845

Asn Ala Gln Leu Glu Thr Glu His His His Pro Met Asp Cys Cys Glu
        850                 855                 860

Ala Ala Gln Thr His Glu Phe Ser Ser Tyr Ile Asn Thr Gly Asp Leu
865                 870                 875                 880

Asn Ser Ser Val Asp Gln Gly Ile Trp Val Val Leu Lys Val Arg Thr
                885                 890                 895

Thr Asp Gly Tyr Ala Thr Leu Gly Asn Leu Glu Leu Val Glu Val Gly
                900                 905                 910

Pro Leu Ser Gly Glu Ser Leu Glu Arg Glu Gln Arg Asp Asn Ala Lys
        915                 920                 925

Trp Ser Ala Glu Leu Gly Arg Lys Arg Ala Glu Thr Asp Arg Val Tyr
        930                 935                 940

Gln Asp Ala Lys Gln Ser Ile Asn His Leu Phe Val Asp Tyr Gln Asp
945                 950                 955                 960

Gln Gln Leu Asn Pro Glu Ile Gly Met Ala Asp Ile Ile Asp Ala Gln
                965                 970                 975

Asn Leu Val Ala Ser Ile Ser Asp Val Tyr Ser Asp Ala Val Leu Gln
                980                 985                 990

Ile Pro Gly Ile Asn Tyr Glu Ile Tyr Thr Glu Leu Ser Asn Arg Leu
        995                 1000                1005

Gln Gln Ala Ser Tyr Leu Tyr Thr Ser Arg Asn Ala Val Gln Asn
    1010                1015                1020

Gly Asp Phe Asn Ser Gly Leu Asp Ser Trp Asn Ala Thr Gly Gly
    1025                1030                1035

Ala Thr Val Gln Gln Asp Gly Asn Thr His Phe Leu Val Leu Ser
    1040                1045                1050

His Trp Asp Ala Gln Val Ser Gln Gln Phe Arg Val Gln Pro Asn
    1055                1060                1065
```

```
Cys Lys Tyr Val Leu Arg Val Thr Ala Glu Lys Val Gly Gly Gly
    1070                1075                1080

Asp Gly Tyr Val Thr Ile Arg Asp Gly Ala His His Thr Glu Lys
    1085                1090                1095

Leu Thr Phe Asn Ala Cys Asp Tyr Asp Ile Asn Gly Thr Tyr Val
    1100                1105                1110

Thr Asp Asn Thr Tyr Leu Thr Lys Glu Val Val Phe Tyr Ser His
    1115                1120                1125

Thr Glu His Met Trp Val Glu Val Ser Glu Thr Glu Gly Ala Phe
    1130                1135                1140

His Ile Asp Ser Ile Glu Phe Val Glu Thr Glu Lys
    1145                1150                1155

<210> SEQ ID NO 21
<211> LENGTH: 1168
<212> TYPE: PRT
<213> ORGANISM: Artificial Sequence
<220> FEATURE:
<223> OTHER INFORMATION: Mutant BT-0009

<400> SEQUENCE: 21

Met Asn Arg Asn Gln Asn Glu Tyr Glu Val Ile Asp Ala Pro His
1               5                   10                  15

Cys Gly Cys Pro Ala Asp Asp Val Val Lys Tyr Pro Leu Thr Asp
                20                  25                  30

Pro Asn Ala Gly Leu Gln Asn Met Asn Tyr Lys Glu Tyr Leu Gln Thr
                35                  40                  45

Tyr Gly Gly Asp Tyr Thr Asp Pro Leu Ile Asn Pro Asn Leu Ser Val
50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
                100                 105                 110

Asp Ala Phe Met Glu Arg Val Glu Glu Leu Ile Asp Gln Lys Ile Ser
                115                 120                 125

Glu Ala Val Lys Gly Arg Ala Leu Asp Asp Leu Thr Gly Leu Gln Tyr
130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
                180                 185                 190

Gln Asn Tyr Ala Thr Ile Leu Leu Pro Val Tyr Ala Gln Ala Ala Asn
                195                 200                 205

Leu His Leu Leu Leu Leu Lys Asp Ala Asp Ile Tyr Gly Ala Arg Trp
                210                 215                 220

Gly Leu Asn Gln Thr Gln Ile Asp Gln Phe His Ser Arg Gln Gln Ser
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Ser Val Ala Ser Trp Leu Lys Tyr His
                260                 265                 270
```

```
Gln Tyr Arg Arg Glu Met Thr Val Thr Ala Met Asp Leu Val Ala Leu
            275                 280                 285

Phe Pro Tyr Tyr Asn Val Arg Gln Tyr Pro Asn Gly Ala Asn Pro Gln
290                 295                 300

Leu Thr Arg Glu Val Tyr Thr Asp Pro Ile Val Phe Asn Pro Pro Glu
305                 310                 315                 320

Arg Pro Ser Gly Ala Phe Cys Glu Ser Phe Tyr Thr Ile Arg Ala Ala
                325                 330                 335

Arg Glu Arg Leu Thr Phe Ser Gln Leu Glu His Ala Ile Ile Arg Pro
            340                 345                 350

Pro Arg Leu Phe Glu Arg Phe Gln Ala Leu Gly Ile Tyr Thr Gly Glu
        355                 360                 365

Ala Arg Leu Asn Ala Asn Ser Ala Pro Met Asn Tyr Trp Ile Gly His
    370                 375                 380

Phe Ile Arg Asn Thr Arg Leu Gly Asp Ser Thr Thr Ile Thr Thr Asn
385                 390                 395                 400

Tyr Gly Thr Thr Asn Asn Arg Leu Thr Asn Phe Ser Met Pro Ser Asp
                405                 410                 415

Val Tyr Gln Ile Asn Ser Thr Ser Ser Asn Leu Ala Ala Ile Leu Gly
            420                 425                 430

Thr Leu Tyr Gly Val Thr Arg Ala Gln Phe His Phe Gly Ser Gly Ser
        435                 440                 445

Phe Ser Thr Tyr Val Gly Gln Asn Ser Val Leu Pro Gln Cys His Gln
    450                 455                 460

Asn Tyr Asn Ser Ile Glu Glu Leu Pro Asn Gln Ser Asp Glu Pro Thr
465                 470                 475                 480

Val Arg Ser Tyr Ser His Arg Leu Ser His Ile Thr Ser Phe Asn Phe
                485                 490                 495

Asn Val Gln Leu Asn Asn Pro Leu Ile Ser Ala Gly Asn Met Pro Val
            500                 505                 510

Tyr Val Trp Thr His Arg Ser Val Asp Leu Thr Asn Arg Ile Ser Ser
        515                 520                 525

Asp Arg Ile Thr Gln Ile Pro Val Val Lys Ala Tyr Glu Leu Ser Ser
    530                 535                 540

Gly Ala Thr Val Val Lys Gly Pro Gly Phe Thr Gly Gly Asp Val Ile
545                 550                 555                 560

Arg Arg Thr Asn Thr Gly Gly Phe Gly Ala Ile Arg Val Ser Val Thr
                565                 570                 575

Gly Pro Leu Thr Gln Arg Tyr Arg Ile Arg Phe Arg Tyr Ala Ser Thr
            580                 585                 590

Ile Asp Phe Asp Phe Phe Val Thr Arg Gly Gly Thr Thr Ile Asn Asn
        595                 600                 605

Phe Arg Phe Thr Arg Thr Met Asn Arg Gly Gln Glu Ser Arg Tyr Glu
    610                 615                 620

Ser Tyr Arg Thr Val Glu Phe Thr Thr Pro Phe Asn Phe Thr Gln Ser
625                 630                 635                 640

Gln Asp Ile Ile Arg Thr Ser Ile Gln Gly Leu Ser Gly Asn Gly Glu
                645                 650                 655

Val Tyr Leu Asp Arg Ile Glu Ile Ile Pro Val Asn Pro Thr Arg Glu
            660                 665                 670

Ala Glu Glu Asp Leu Glu Ala Ala Lys Lys Ala Val Ala Ser Leu Phe
        675                 680                 685

Thr Arg Thr Arg Asp Gly Leu Gln Val Asn Val Lys Asp Tyr Gln Val
```

```
                690             695             700
Asp Gln Ala Ala Asn Leu Val Ser Cys Leu Ser Asp Glu Gln Tyr Gly
705             710             715             720

Tyr Asp Lys Lys Met Leu Leu Glu Ala Val Arg Ala Ala Lys Arg Leu
            725             730             735

Ser Arg Glu Arg Asn Leu Leu Gln Asp Pro Asp Phe Asn Thr Ile Asn
            740             745             750

Ser Thr Glu Glu Asn Gly Trp Lys Ala Ser Asn Gly Val Thr Ile Ser
            755             760             765

Glu Gly Gly Pro Phe Tyr Lys Gly Arg Ala Leu Gln Leu Ala Ser Ala
            770             775             780

Arg Glu Asn Tyr Pro Thr Tyr Ile Tyr Gln Lys Val Asp Ala Ser Glu
785             790             795             800

Leu Lys Pro Tyr Thr Arg Tyr Arg Leu Asp Gly Phe Val Lys Ser Ser
            805             810             815

Gln Asp Leu Glu Ile Asp Leu Ile His His Lys Val His Leu Val
            820             825             830

Lys Asn Val Pro Asp Asn Leu Val Ser Asp Thr Tyr Pro Asp Asp Ser
            835             840             845

Cys Ser Gly Ile Asn Arg Cys Gln Glu Gln Met Val Asn Ala Gln
            850             855             860

Leu Glu Thr Glu His His His Pro Met Asp Cys Cys Glu Ala Ala Gln
865             870             875             880

Thr His Glu Phe Ser Ser Tyr Ile Asp Thr Gly Asp Leu Asn Ser Thr
            885             890             895

Val Asp Gln Gly Ile Trp Val Ile Phe Lys Val Arg Thr Thr Asp Gly
            900             905             910

Tyr Ala Thr Leu Gly Asn Leu Glu Leu Val Glu Val Gly Pro Leu Leu
            915             920             925

Gly Glu Pro Leu Glu Arg Glu Gln Arg Glu Asn Ala Lys Trp Asn Ala
            930             935             940

Glu Leu Gly Arg Lys Arg Ala Glu Thr Asp Arg Val Tyr Gln Asp Ala
945             950             955             960

Lys Gln Ser Ile Asn His Leu Phe Val Asp Tyr Gln Asp Gln Gln Leu
            965             970             975

Asn Pro Glu Ile Gly Met Ala Asp Ile Met Asp Ala Gln Asn Leu Val
            980             985             990

Ala Ser Ile Ser Asp Val Tyr Ser Asp Ala Val Leu Gln Ile Pro Gly
            995             1000            1005

Ile Asn Tyr Glu Ile Tyr Thr Glu Leu Ser Asn Arg Leu Gln Gln
            1010            1015            1020

Ala Ser Tyr Leu Tyr Thr Ser Arg Asn Ala Val Gln Asn Gly Asp
            1025            1030            1035

Phe Asn Asn Gly Leu Asp Ser Trp Asn Ala Thr Ala Gly Ala Ser
            1040            1045            1050

Val Gln Gln Asp Gly Asn Thr His Phe Leu Val Leu Ser His Trp
            1055            1060            1065

Asp Ala Gln Val Ser Gln Gln Phe Arg Val Gln Pro Asn Cys Lys
            1070            1075            1080

Tyr Val Leu Arg Val Thr Ala Glu Lys Val Gly Gly Gly Asp Gly
            1085            1090            1095

Tyr Val Thr Ile Arg Asp Asp Ala His Thr Glu Thr Leu Thr
            1100            1105            1110
```

```
Phe Asn Ala Cys Asp Tyr Asp Ile Asn Gly Thr Tyr Val Thr Asp
    1115                1120                1125

Asn Thr Tyr Ile Thr Lys Glu Val Val Phe Tyr Ser His Thr Asp
    1130                1135                1140

His Met Trp Val Glu Val Ser Glu Thr Glu Gly Ala Phe His Ile
    1145                1150                1155

Asp Ser Leu Glu Phe Val Glu Thr Glu Lys
    1160                1165

<210> SEQ ID NO 22
<211> LENGTH: 1156
<212> TYPE: PRT
<213> ORGANISM: Artificial Sequence
<220> FEATURE:
<223> OTHER INFORMATION: Mutant BT-0012

<400> SEQUENCE: 22

Met Asn Gln Asn Lys His Gly Ile Ile Gly Ala Ser Asn Cys Gly Cys
1               5                   10                  15

Ala Ser Asp Asp Val Ala Lys Tyr Pro Leu Ala Asn Asn Pro Tyr Ser
                20                  25                  30

Ser Ala Leu Asn Leu Asn Ser Cys Gln Asn Ser Ser Ile Leu Asn Trp
            35                  40                  45

Ile Asn Ile Ile Gly Asp Ala Ala Lys Glu Ala Val Ser Ile Gly Thr
        50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Ile Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe Phe His Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300
```

```
Thr Asp Pro Ile Gly Phe Val His Arg Ser Ser Leu Arg Gly Glu Ser
305                 310                 315                 320

Trp Phe Ser Phe Val Asn Arg Ala Asn Phe Ser Asp Leu Glu Asn Ala
            325                 330                 335

Ile Pro Asn Pro Arg Pro Ser Trp Phe Leu Asn Asn Met Ile Ile Ser
                340                 345                 350

Thr Gly Ser Leu Thr Leu Pro Val Ser Pro Ser Thr Asp Arg Ala Arg
            355                 360                 365

Val Trp Tyr Gly Ser Arg Asp Arg Ile Ser Pro Ala Asn Ser Gln Phe
            370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
            435                 440                 445

Ile Asp Asn Pro Arg Val Gln Asn Ile Asn Thr Tyr Leu Pro Gly Glu
450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
            515                 520                 525

Asp Thr Arg Gly Thr Gly Val Ser Tyr Val Asn Asp Pro Gly Phe Ile
530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
            595                 600                 605

Leu Arg Tyr Gly Ser Phe Ala Ile Arg Glu Phe Asn Thr Ser Ile Arg
610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
            660                 665                 670

Ala Ser Leu Phe Thr Arg Thr Arg Asp Gly Leu Gln Val Asn Val Lys
            675                 680                 685

Asp Tyr Gln Val Asp Gln Ala Ala Asn Leu Val Ser Cys Leu Ser Asp
            690                 695                 700

Glu Gln Tyr Gly Tyr Asp Lys Lys Met Leu Leu Glu Ala Val Arg Ala
705                 710                 715                 720
```

```
Ala Lys Arg Leu Ser Arg Glu Arg Asn Leu Leu Gln Asp Pro Asp Phe
            725                 730                 735

Asn Thr Ile Asn Ser Thr Glu Gly Asn Gly Trp Lys Ala Ser Asn Gly
            740                 745                 750

Val Thr Ile Ser Glu Gly Gly Pro Phe Tyr Lys Gly Arg Ala Ile Gln
            755                 760                 765

Leu Ala Ser Ala Arg Glu Asn Tyr Pro Thr Tyr Ile Tyr Gln Lys Val
            770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
            805                 810                 815

Val His Leu Val Lys Asn Val Pro Asp Asn Leu Val Leu Asp Thr Tyr
            820                 825                 830

Pro Asp Asp Ser Cys Asn Gly Ile Asn Arg Cys Asp Glu Gln Lys Met
            835                 840                 845

Val Asn Ala Gln Leu Glu Thr Glu His His Pro Met Asp Cys Cys
            850                 855                 860

Glu Ala Ala Gln Thr His Glu Phe Ser Ser Tyr Ile Asn Thr Gly Asp
865                 870                 875                 880

Leu Asn Ala Ser Val Asp Gln Gly Ile Trp Val Val Leu Lys Val Arg
            885                 890                 895

Thr Thr Asp Gly Tyr Ala Thr Leu Gly Asn Leu Glu Leu Val Glu Val
            900                 905                 910

Gly Pro Leu Ser Gly Glu Ser Leu Glu Arg Glu Gln Arg Asp Asn Ala
            915                 920                 925

Lys Trp Ser Ala Glu Leu Gly Arg Lys Arg Ala Glu Thr Glu Arg Val
            930                 935                 940

Tyr Tyr Ala Ala Lys Gln Ser Ile Asn His Leu Phe Val Asp Tyr Arg
945                 950                 955                 960

Asp Gln Gln Leu Asn Pro Gln Ile Gly Met Ala Asp Ile Met Asp Ala
            965                 970                 975

Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
            995                 1000                1005

Leu Gln Gln Ala Ser Tyr Leu His Met Ser Arg Asn Ala Met Gln
            1010                1015                1020

Asn Gly Asp Phe Asn Ser Gly Leu Asp Ser Trp Asn Ala Thr Ala
            1025                1030                1035

Gly Ala Thr Val Gln Gln Asp Gly Asn Thr His Phe Leu Val Leu
            1040                1045                1050

Ser His Trp Asp Ala Gln Val Ser Gln Gln Phe Arg Val Gln Pro
            1055                1060                1065

Asn Cys Lys Tyr Val Leu Arg Val Thr Ala Glu Lys Val Gly Gly
            1070                1075                1080

Gly Asp Gly Tyr Val Thr Ile Arg Asp Gly Ala His His Thr Glu
            1085                1090                1095

Thr Leu Thr Phe Asn Ala Cys Asp Tyr Asp Ile Asn Gly Thr Tyr
            1100                1105                1110

Val Thr Asp Asn Thr Tyr Leu Thr Lys Glu Val Val Phe His Pro
            1115                1120                1125

Glu Thr Gln His Met Trp Val Glu Val Ser Glu Thr Glu Gly Val
```

```
                1130                1135                1140
  Phe His  Leu Asp Ser Val Glu  Phe Met Glu Thr Gln  Gln
            1145                1150                1155

<210> SEQ ID NO 23
<211> LENGTH: 1156
<212> TYPE: PRT
<213> ORGANISM: Artificial Sequence
<220> FEATURE:
<223> OTHER INFORMATION: Mutant BT-0013

<400> SEQUENCE: 23

Met Asn Gln Asn Lys His Gly Ile Ile Gly Ala Ser Asn Cys Gly Cys
 1               5                  10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
    50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Ile Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
    130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Arg Asp Ala
        195                 200                 205

Thr Arg Tyr Gly Thr Asn Trp Gly Leu Tyr Asn Ala Thr Pro Phe Ile
    210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
    290                 295                 300

Thr Asp Pro Ile Gly Phe Val His Arg Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
```

```
              340                 345                 350
Thr Gly Ser Leu Thr Leu Pro Val Ser Pro Ser Thr Asp Arg Ala Arg
            355                 360                 365

Val Trp Tyr Gly Ser Arg Asp Arg Ile Ser Pro Ala Asn Ser Gln Phe
370                 375                 380

Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
                405                 410                 415

Asp Thr Thr Tyr Gly Val Asn Arg Ala Val Phe Tyr His Asp Ala Ser
            420                 425                 430

Glu Gly Ser Gln Arg Ser Val Tyr Glu Gly Tyr Ile Arg Thr Thr Gly
        435                 440                 445

Ile Asp Asn Pro Arg Val Gln Asn Ile Asn Thr Tyr Leu Pro Gly Glu
            450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
                485                 490                 495

Ser Ser Leu Val Met Tyr Gly Trp Thr His Lys Ser Leu Ala Arg Asn
            500                 505                 510

Asn Thr Ile Asn Pro Asp Arg Ile Thr Gln Ile Pro Leu Thr Lys Val
            515                 520                 525

Asp Thr Arg Gly Thr Gly Val Ser Tyr Val Asn Asp Pro Gly Phe Ile
        530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
                565                 570                 575

Arg Tyr Ala Ser Thr Thr Asn Ile Arg Leu Ser Val Asn Gly Ser Phe
            580                 585                 590

Gly Thr Ile Ser Gln Asn Leu Pro Ser Thr Met Arg Leu Gly Glu Asp
            595                 600                 605

Leu Arg Tyr Gly Ser Phe Ala Ile Arg Glu Phe Asn Thr Ser Ile Arg
        610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
                645                 650                 655

Pro Thr Arg Glu Ala Lys Glu Asp Leu Glu Ala Ala Lys Lys Ala Val
            660                 665                 670

Ala Ser Leu Phe Thr Arg Thr Arg Asp Gly Leu Gln Val Asn Val Lys
            675                 680                 685

Asp Tyr Gln Val Asp Gln Ala Ala Asn Leu Val Ser Cys Leu Ser Asp
        690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
                725                 730                 735

Asn Thr Ile Asn Ser Thr Glu Glu Asn Gly Trp Lys Ala Ser Asn Gly
            740                 745                 750

Val Thr Ile Ser Glu Gly Gly Pro Phe Tyr Lys Gly Arg Ala Ile Gln
            755                 760                 765
```

-continued

Leu Ala Ser Ala Arg Glu Asn Tyr Pro Thr Tyr Ile Tyr Gln Lys Val
            770                 775                 780

Asp Ala Ser Glu Leu Lys Pro Tyr Thr Arg Tyr Arg Leu Asp Gly Phe
785                 790                 795                 800

Val Lys Ser Ser Gln Asp Leu Glu Ile Asp Leu Ile His His His Lys
                805                 810                 815

Val His Leu Val Lys Asn Val Pro Asp Asn Leu Val Leu Asp Thr Tyr
            820                 825                 830

Pro Asp Asp Ser Cys Asn Gly Ile Asn Arg Cys Asp Glu Gln Lys Met
            835                 840                 845

Val Asn Ala Gln Leu Glu Thr Gly His His His Pro Met Asp Cys Cys
850                 855                 860

Glu Ala Ala Gln Thr His Glu Phe Ser Ser Tyr Ile Asn Thr Gly Asp
865                 870                 875                 880

Leu Asn Ala Ser Val Asp Gln Gly Ile Trp Val Val Leu Lys Val Arg
                885                 890                 895

Thr Thr Asp Gly Tyr Ala Thr Leu Gly Asn Leu Glu Leu Val Glu Val
            900                 905                 910

Gly Pro Leu Ser Gly Glu Ser Leu Glu Arg Glu Gln Arg Asp Asn Ala
            915                 920                 925

Lys Trp Ser Ala Glu Leu Gly Arg Lys Arg Ala Glu Thr Glu Arg Val
            930                 935                 940

Tyr Tyr Ala Ala Lys Gln Ser Ile Asn His Leu Phe Val Asp Tyr Gln
945                 950                 955                 960

Asp Gln Gln Leu Asn Pro Gln Ile Gly Met Ala Asp Ile Met Asp Ala
                965                 970                 975

Gln Asn Leu Val Ala Ser Ile Ser Asp Val Tyr Ser Asp Ala Val Leu
            980                 985                 990

Gln Ile Pro Gly Ile Asn Tyr Glu Ile Tyr Thr Glu Leu Ser Asn Arg
            995                 1000                1005

Leu Gln Gln Ala Ser Tyr Leu His Thr Ser Arg Asn Ala Met Gln
        1010                1015                1020

Asn Gly Asp Phe Asn Ser Gly Leu Asp Ser Trp Asn Ala Thr Ala
        1025                1030                1035

Gly Ala Thr Val Gln Gln Asp Gly Asn Thr His Phe Leu Val Leu
        1040                1045                1050

Ser His Trp Asp Ala Gln Val Ser Gln Gln Phe Arg Val Gln Pro
        1055                1060                1065

Asn Cys Lys Tyr Val Leu Arg Val Thr Ala Glu Lys Val Gly Gly
        1070                1075                1080

Gly Asp Gly Tyr Val Thr Ile Arg Asp Gly Ala His His Thr Glu
        1085                1090                1095

Thr Leu Thr Phe Asn Ala Cys Asp Tyr Asp Ile Asn Gly Thr Tyr
        1100                1105                1110

Val Thr Asp Asn Thr Tyr Leu Thr Lys Glu Val Val Phe His Pro
        1115                1120                1125

Glu Thr Gln His Met Trp Val Glu Val Ser Glu Thr Glu Gly Val
        1130                1135                1140

Phe His Leu Asp Ser Val Glu Phe Met Glu Thr Gln Gln
        1145                1150

<210> SEQ ID NO 24
<211> LENGTH: 1152

<212> TYPE: PRT
<213> ORGANISM: Artificial Sequence
<220> FEATURE:
<223> OTHER INFORMATION: Mutant BT-0023

<400> SEQUENCE: 24

```
Met Asn Arg Asn Asn Pro Asn Glu Tyr Glu Ile Ile Asp Ala Pro Tyr
1               5                   10                  15

Cys Gly Cys Pro Ser Asp Asp Val Arg Tyr Pro Leu Ala Ser Asp
            20                  25                  30

Pro Asn Ala Ala Phe Gln Asn Met Asn Tyr Lys Glu Tyr Leu Gln Thr
            35                  40                  45

Tyr Asp Gly Asp Tyr Thr Gly Ser Leu Ile Asn Pro Asn Leu Ser Ile
50                  55                  60

Asn Pro Arg Asp Val Leu Gln Thr Gly Ile Asn Ile Val Gly Arg Ile
65                  70                  75                  80

Leu Gly Phe Leu Gly Val Pro Phe Ala Gly Gln Leu Val Thr Phe Tyr
                85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
            115                 120                 125

Ala Gln Val Val Arg Asn Ala Leu Asp Asp Leu Thr Gly Leu His Asp
130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
            165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
            195                 200                 205

Leu His Leu Leu Leu Leu Lys Asp Ala Glu Ile Tyr Gly Ala Arg Trp
210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
            245                 250                 255

Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
            275                 280                 285

Phe Pro Tyr Tyr Asn Val Arg Gln Tyr Pro Asn Gly Ala Asn Pro Gln
290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
            325                 330                 335

Ser Glu Leu Glu Asn Ala Phe Ile Arg Pro Pro His Leu Phe Asp Arg
            340                 345                 350

Leu Asn Arg Leu Thr Ile Ser Arg Asn Arg Tyr Thr Ala Pro Thr Thr
            355                 360                 365

Asn Ser Tyr Leu Asp Tyr Trp Ser Gly His Thr Leu Gln Ser Gln Tyr
370                 375                 380
```

```
Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Asn Ala Ile Asp Ser
            405                 410                 415

Arg Ala Arg Asn Phe Gly Asn Leu Tyr Ala Asn Leu Tyr Gly Val Ser
        420                 425                 430

Ser Leu Asn Ile Phe Pro Thr Gly Val Met Ser Glu Ile Thr Ser Ala
            435                 440                 445

Pro Asn Thr Cys Trp Gln Asp Leu Thr Thr Thr Glu Glu Leu Pro Leu
    450                 455                 460

Val Asn Asn Asn Phe Asn Leu Leu Ser His Val Thr Phe Leu Arg Phe
465                 470                 475                 480

Asn Thr Thr Gln Gly Gly Pro Leu Ala Thr Val Gly Phe Val Pro Thr
            485                 490                 495

Tyr Val Trp Thr Arg Gln Asp Val Asp Phe Asn Asn Ile Ile Thr Pro
            500                 505                 510

Asn Arg Ile Thr Gln Ile Pro Val Val Lys Ala Tyr Glu Leu Ser Ser
            515                 520                 525

Gly Ala Thr Val Val Lys Gly Pro Gly Phe Thr Gly Gly Asp Val Ile
        530                 535                 540

Arg Arg Thr Asn Thr Gly Gly Phe Gly Ala Ile Arg Val Ser Val Thr
545                 550                 555                 560

Gly Pro Leu Thr Gln Arg Tyr Arg Ile Arg Phe Arg Tyr Ala Ser Thr
            565                 570                 575

Ile Asp Phe Asp Phe Phe Val Thr Arg Gly Gly Thr Thr Ile Asn Asn
            580                 585                 590

Phe Arg Phe Thr Arg Thr Met Asn Arg Gly Gln Glu Ser Arg Tyr Glu
            595                 600                 605

Ser Tyr Arg Thr Val Glu Phe Thr Thr Pro Phe Asn Phe Thr Gln Ser
            610                 615                 620

Gln Asp Ile Ile Arg Thr Ser Ile Gln Gly Leu Ser Gly Asn Gly Glu
625                 630                 635                 640

Val Tyr Leu Asp Arg Ile Glu Ile Ile Pro Val Asn Pro Thr Arg Glu
            645                 650                 655

Ala Glu Glu Asp Leu Glu Ala Ala Lys Lys Ala Val Ala Ser Leu Phe
            660                 665                 670

Thr Arg Thr Arg Asp Gly Leu Gln Val Asn Val Thr Asp Tyr Gln Val
            675                 680                 685

Asp Gln Ala Ala Asn Leu Val Ser Cys Leu Ser Asp Glu Gln Tyr Ala
            690                 695                 700

His Asp Lys Lys Met Leu Leu Glu Ala Val Arg Ala Ala Lys Arg Leu
705                 710                 715                 720

Ser Arg Glu Arg Asn Leu Leu Gln Asp Pro Asp Phe Asn Thr Ile Asn
            725                 730                 735

Ser Thr Glu Glu Asn Gly Trp Lys Ala Ser Asn Gly Val Thr Ile Ser
            740                 745                 750

Glu Gly Gly Pro Phe Tyr Lys Gly Arg Ala Leu Gln Leu Ala Ser Ala
            755                 760                 765

Arg Glu Asn Tyr Pro Thr Tyr Ile Tyr Gln Lys Val Asp Ala Ser Glu
            770                 775                 780

Leu Lys Pro Tyr Thr Arg Tyr Arg Leu Asp Gly Phe Val Lys Ser Ser
785                 790                 795                 800

Gln Asp Leu Glu Ile Asp Leu Ile His His His Lys Val His Leu Val
```

```
                    805                 810                 815
Lys Asn Val Leu Asp Asn Leu Val Ser Asp Thr Tyr Pro Asp Asp Ser
                820                 825                 830

Cys Ser Gly Ile Asn Arg Cys Glu Glu Gln Met Val Asn Ala Gln
            835                 840                 845

Leu Glu Thr Glu His His His Pro Met Asp Cys Cys Glu Ala Ala Gln
850                 855                 860

Thr His Glu Phe Ser Ser Tyr Ile Asp Thr Gly Asp Leu Asn Ser Thr
865                 870                 875                 880

Val Asp Gln Gly Ile Trp Val Ile Phe Lys Val Arg Thr Thr Asp Gly
                885                 890                 895

Tyr Ala Thr Leu Gly Asn Leu Glu Leu Val Glu Val Gly Pro Leu Leu
            900                 905                 910

Gly Glu Pro Leu Glu Arg Glu Gln Arg Glu Asn Ala Lys Trp Asn Ala
        915                 920                 925

Glu Leu Gly Arg Lys Arg Ala Glu Thr Asp Arg Val Tyr Gln Asp Ala
    930                 935                 940

Lys Gln Ser Ile Asn His Leu Phe Val Asp Tyr Gln Asp Gln Leu
945                 950                 955                 960

Asn Pro Gln Ile Gly Met Ala Asp Ile Met Asp Ala Gln Asn Leu Val
                965                 970                 975

Ala Ser Ile Ser Asp Val Tyr Ser Asp Ala Val Leu Gln Ile Pro Gly
            980                 985                 990

Ile Asn Tyr Glu Ile Tyr Thr Glu Leu Ser Asn Arg Leu Gln Gln Ala
        995                 1000                1005

Ser Tyr Leu Tyr Thr Ser Arg Asn Ala Val Gln Asn Gly Asp Phe
    1010                1015                1020

Asn Asn Gly Leu Asp Ser Trp Asn Ala Thr Ala Gly Ala Ser Val
    1025                1030                1035

Gln Gln Asp Gly Asn Thr His Phe Leu Val Leu Ser His Trp Asp
    1040                1045                1050

Ala Gln Val Ser Gln Gln Phe Arg Val Gln Pro Asn Cys Lys Tyr
    1055                1060                1065

Val Leu Arg Val Thr Ala Glu Lys Val Gly Gly Gly Asp Gly Tyr
    1070                1075                1080

Val Thr Ile Arg Asp Gly Ala His His Thr Glu Thr Leu Thr Phe
    1085                1090                1095

Asn Ala Cys Asp Tyr Asp Ile Asn Gly Thr Tyr Val Thr Asp Asn
    1100                1105                1110

Thr Tyr Leu Thr Lys Glu Val Leu Phe Tyr Ser His Thr Glu His
    1115                1120                1125

Met Trp Val Glu Val Asn Glu Thr Glu Gly Ala Phe His Leu Asp
    1130                1135                1140

Ser Ile Glu Phe Val Glu Thr Glu Lys
    1145                1150

<210> SEQ ID NO 25
<211> LENGTH: 1155
<212> TYPE: PRT
<213> ORGANISM: Artificial Sequence
<220> FEATURE:
<223> OTHER INFORMATION: Mutant BT-0067

<400> SEQUENCE: 25

Met Asn Arg Asn Asn Gln Asp Glu Tyr Glu Ile Ile Asp Ala Ser Thr
```

-continued

```
1               5                   10                  15
Cys Gly Cys Ser Ser Asp Asp Val Val Gln Tyr Pro Leu Ala Arg Asp
                20                  25                  30
Pro Asn Ala Val Phe Gln Asn Met His Tyr Lys Asp Tyr Leu Gln Thr
                35              40                  45
Tyr Asp Gly Asp Tyr Thr Gly Ser Leu Ile Asn Pro Asn Leu Ser Ile
 50                     55                  60
Asn Pro Arg Asp Val Leu Gln Thr Gly Ile Asn Ile Val Gly Arg Leu
 65                 70                  75                  80
Leu Gly Phe Leu Gly Val Pro Phe Ala Gly Gln Leu Val Thr Phe Tyr
                85                  90                  95
Thr Phe Leu Leu Asn Gln Leu Trp Pro Thr Asn Asp Asn Ala Val Trp
                100                 105                 110
Glu Ala Phe Met Ala Gln Ile Glu Glu Leu Ile Asn Gln Arg Ile Ser
                115                 120                 125
Glu Ala Val Val Gly Thr Ala Ala Asp His Leu Thr Gly Leu His Asp
                130                 135             140
Asn Tyr Glu Leu Tyr Val Glu Ala Leu Glu Glu Trp Leu Glu Arg Pro
145                 150                 155                 160
Asn Ala Ala Arg Thr Asn Leu Leu Phe Asn Arg Phe Thr Thr Leu Asp
                165                 170                 175
Ser Leu Phe Thr Gln Phe Met Pro Ser Phe Gly Thr Gly Pro Gly Ser
                180                 185                 190
Gln Asn Tyr Ala Val Pro Leu Leu Thr Val Tyr Ala Gln Ala Ala Asn
                195                 200                 205
Leu His Leu Leu Leu Lys Asp Ala Glu Ile Tyr Gly Ala Arg Trp
                210                 215                 220
Gly Leu Asn Gln Asn Gln Ile Asn Ser Phe His Thr Arg Gln Gln Glu
225                 230                 235                 240
Arg Thr Gln Tyr Tyr Thr Asn His Cys Val Thr Thr Tyr Asn Thr Gly
                245                 250                 255
Leu Asp Arg Leu Arg Gly Thr Asn Thr Glu Ser Trp Leu Asn Tyr His
                260                 265                 270
Arg Phe Arg Arg Glu Met Thr Leu Met Ala Met Asp Leu Val Ala Leu
                275                 280                 285
Phe Pro Tyr Tyr Asn Val Arg Gln Tyr Pro Asn Gly Ala Asn Pro Gln
                290                 295                 300
Leu Thr Arg Glu Ile Tyr Thr Asp Pro Ile Val Phe Asn Pro Pro Ala
305                 310                 315                 320
Asn Val Gly Leu Cys Arg Arg Trp Gly Asn Asn Pro Tyr Asn Arg Phe
                325                 330                 335
Ser Glu Leu Glu Asn Ala Phe Ile Arg Pro Pro His Leu Phe Asp Arg
                340                 345                 350
Leu Asn Thr Leu Thr Ile Ser Arg Asn Arg Phe Asp Val Gly Ser Asn
                355                 360                 365
Phe Ile Glu Pro Trp Ser Gly His Thr Leu Arg Arg Ser Tyr Ser Asn
                370                 375                 380
Asn Ser Thr Val Tyr Glu Asp Ser Tyr Gly Gln Ile Thr Ala Thr Arg
385                 390                 395                 400
Thr Thr Ile Asn Leu Pro Ala Asn Gly Thr Gly Arg Val Glu Ser Thr
                405                 410                 415
Ala Val Asp Phe Arg Ser Ala Leu Val Gly Ile Tyr Gly Val Asn Arg
                420                 425                 430
```

```
Ala Ser Phe Ile Pro Gly Gly Val Phe Ser Gly Thr Thr Gln Pro Ser
        435                 440                 445
Thr Gly Gly Cys Arg Asp Leu Tyr Asp Ser Ser Asp Glu Leu Pro Pro
    450                 455                 460
Asp Glu Ser Thr Gly Ser Phe Ala His Arg Leu Ser His Val Thr Phe
465                 470                 475                 480
Leu Ser Phe Thr Thr Asn Gln Ala Gly Ser Ile Ala Asn Ser Gly Arg
                485                 490                 495
Val Pro Thr Tyr Val Trp Thr His Arg Asp Val Asp Phe Asn Asn Thr
            500                 505                 510
Ile Asn Pro Asn Arg Ile Thr Gln Ile Pro Val Val Lys Ala Tyr Glu
        515                 520                 525
Leu Ser Ser Gly Ala Thr Val Val Lys Gly Pro Gly Phe Thr Gly Gly
    530                 535                 540
Asp Val Ile Arg Arg Thr Asn Ile Gly Gly Phe Gly Ala Ile Arg Val
545                 550                 555                 560
Ser Val Thr Gly Pro Leu Thr Gln Arg Tyr Arg Ile Arg Phe Arg Tyr
                565                 570                 575
Ala Ser Thr Ile Asp Phe Asp Phe Phe Val Thr Arg Gly Gly Thr Thr
            580                 585                 590
Ile Asn Asn Phe Arg Phe Thr Arg Thr Met Asn Arg Gly Gln Glu Ser
        595                 600                 605
Arg Tyr Glu Ser Tyr Arg Thr Val Glu Phe Thr Thr Pro Phe Asn Phe
    610                 615                 620
Thr Gln Ser Gln Asp Ile Ile Arg Thr Ser Ile Gln Gly Leu Ser Gly
625                 630                 635                 640
Asn Gly Glu Val Tyr Leu Asp Arg Ile Glu Ile Ile Pro Val Asn Pro
                645                 650                 655
Thr Arg Glu Ala Glu Glu Asp Leu Glu Ala Ala Lys Lys Ala Val Ala
            660                 665                 670
Ser Leu Phe Thr Arg Thr Arg Asp Gly Leu Gln Val Asn Val Thr Asp
        675                 680                 685
Tyr Gln Val Asp Gln Ala Ala Asn Leu Val Ser Cys Leu Ser Asp Glu
    690                 695                 700
Gln Tyr Gly His Asp Lys Lys Met Leu Leu Glu Ala Val Arg Ala Ala
705                 710                 715                 720
Lys Arg Leu Ser Arg Glu Arg Asn Leu Leu Gln Asp Pro Asp Phe Asn
                725                 730                 735
Thr Ile Asn Ser Thr Glu Glu Asn Gly Trp Lys Ala Ser Asn Gly Val
            740                 745                 750
Thr Ile Ser Glu Gly Gly Pro Phe Tyr Lys Gly Arg Ala Leu Gln Leu
        755                 760                 765
Ala Ser Ala Arg Glu Asn Tyr Pro Thr Tyr Ile Tyr Gln Lys Val Asn
    770                 775                 780
Ala Ser Glu Leu Lys Pro Tyr Thr Arg Tyr Arg Leu Asp Gly Phe Val
785                 790                 795                 800
Lys Ser Ser Gln Asp Leu Glu Ile Asp Leu Ile His His Lys Val
                805                 810                 815
His Leu Val Lys Asn Val Pro Asp Asn Leu Val Ser Asp Thr Tyr Ser
            820                 825                 830
Asp Gly Ser Cys Ser Gly Met Asn Arg Cys Glu Glu Gln Gln Met Val
        835                 840                 845
```

Asn Ala Gln Leu Glu Thr Glu His His His Pro Met Asp Cys Cys Glu
    850                 855                 860

Ala Ala Gln Thr His Glu Phe Ser Ser Tyr Ile Asn Thr Gly Asp Leu
865                 870                 875                 880

Asn Ser Ser Val Asp Gln Gly Ile Trp Val Val Leu Lys Val Arg Thr
            885                 890                 895

Thr Asp Gly Tyr Ala Thr Leu Gly Asn Leu Glu Leu Val Glu Val Gly
        900                 905                 910

Pro Leu Ser Gly Glu Ser Leu Glu Arg Glu Gln Arg Asp Asn Ala Lys
            915                 920                 925

Trp Ser Ala Glu Leu Gly Arg Lys Arg Ala Glu Thr Asp Arg Val Tyr
    930                 935                 940

Gln Asp Ala Lys Gln Ser Ile Asn His Leu Phe Val Asp Tyr Gln Asp
945                 950                 955                 960

Gln Gln Leu Asn Pro Glu Ile Gly Met Ala Asp Ile Ile Asp Ala Gln
            965                 970                 975

Asn Leu Val Ala Ser Ile Ser Asp Val Tyr Ser Asp Ala Val Leu Gln
        980                 985                 990

Ile Pro Gly Ile Asn Tyr Glu Ile Tyr Thr Glu Leu Ser Asn Arg Leu
    995                 1000                1005

Gln Gln Ala Ser Tyr Leu Tyr Thr Ser Arg Asn Ala Val Gln Asn
    1010                1015                1020

Gly Asp Phe Asn Ser Gly Leu Asp Ser Trp Asn Ala Thr Gly Gly
    1025                1030                1035

Ala Thr Val Gln Gln Asp Gly Asn Thr His Phe Leu Val Leu Ser
    1040                1045                1050

His Trp Asp Ala Gln Val Ser Gln Gln Phe Arg Val Gln Pro Asn
    1055                1060                1065

Cys Lys Tyr Val Leu Arg Val Thr Ala Glu Lys Val Gly Gly Gly
    1070                1075                1080

Asp Gly Tyr Val Thr Ile Arg Asp Gly Ala His His Thr Glu Lys
    1085                1090                1095

Leu Thr Phe Asn Ala Cys Asp Tyr Asp Ile Asn Gly Thr Tyr Val
    1100                1105                1110

Thr Asp Asn Thr Tyr Ile Thr Lys Glu Val Val Phe Tyr Ser His
    1115                1120                1125

Thr Glu His Met Trp Val Glu Val Ser Glu Thr Glu Gly Ala Phe
    1130                1135                1140

His Leu Asp Ser Ile Glu Phe Val Glu Thr Glu Lys
    1145                1150                1155

<210> SEQ ID NO 26
<211> LENGTH: 26
<212> TYPE: DNA
<213> ORGANISM: Artificial Sequence
<220> FEATURE:
<223> OTHER INFORMATION: OAR2613a Forward Primer

<400> SEQUENCE: 26
aaacatgaac cgaaataatc aaaatg                                        26

<210> SEQ ID NO 27
<211> LENGTH: 22
<212> TYPE: DNA
<213> ORGANISM: Artificial Sequence
<220> FEATURE:
<223> OTHER INFORMATION: OAR2615a Reverse Primer

```
<400> SEQUENCE: 27
atccgtccct tgtgcgtgta aa                                               22

<210> SEQ ID NO 28
<211> LENGTH: 30
<212> TYPE: DNA
<213> ORGANISM: Artificial Sequence
<220> FEATURE:
<223> OTHER INFORMATION: OAR2611a-F forward primer

<400> SEQUENCE: 28
gtttaaacat gaatcgaaat aatcaaaatg                                       30

<210> SEQ ID NO 29
<211> LENGTH: 29
<212> TYPE: DNA
<213> ORGANISM: Artificial Sequence
<220> FEATURE:
<223> OTHER INFORMATION: OAR2612a-R reverse primer

<400> SEQUENCE: 29
ggcgcgccct actcttgtgt ttcaataaa                                        29

<210> SEQ ID NO 30
<211> LENGTH: 29
<212> TYPE: DNA
<213> ORGANISM: Artificial Sequence
<220> FEATURE:
<223> OTHER INFORMATION: OAR2768-F forward primer

<400> SEQUENCE: 30
gtttaaacat gaatcaaaat aaacacgga                                        29

<210> SEQ ID NO 31
<211> LENGTH: 31
<212> TYPE: DNA
<213> ORGANISM: Artificial Sequence
<220> FEATURE:
<223> OTHER INFORMATION: OAR2769-R reverse primer

<400> SEQUENCE: 31
ggcgcgcctt actgttgggt ttccatgaac t                                     31
```

COMPOSITIONS AND METHODS FOR CONTROLLING PLANT PESTS

RELATED APPLICATION INFORMATION

This application is a 371 of International Application No. PCT/US2015/063620 filed Dec. 3, 2015, which claims priority to U.S. Provisional Application No. 62/090,900, filed Dec. 12, 2014, the contents of which are incorporated herein by reference.

REFERENCE TO SEQUENCE LISTING SUBMITTED ELECTRONICALLY

The official copy of the sequence listing is submitted electronically via EFS-Web as an ASCII formatted sequence listing with a file named "80670-WO-REG-ORG-P-1.txt", created on Dec. 5, 2014, and having a size of 171 kilobytes and is filed concurrently with the specification. The sequence listing contained in this ASCII formatted document is part of the specification and is herein incorporated by reference in its entirety.

FIELD OF THE INVENTION

This invention relates to pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran larvae. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc. The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature.

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for lepidopteran-active Cry proteins and 60-80 kDa for coleopteran-active Cry proteins. Protoxins are converted into mature toxic fragments (approximately 60-70 kDa N terminal region) by gut proteases in the target pest. Many of these proteins are quite toxic to specific target insects, but harmless to plants and other non-targeted organisms.

Cry proteins generally have five conserved sequence domains, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or compliment to chemical pesticides. The genes coding for some of these Cry proteins have been isolated and their expression in heterologous hosts such as transgenic plants have been shown to provide another tool for the control of economically important insect pests.

Good insect control can thus be reached, but certain chemicals can sometimes also affect non-target beneficial insects and certain biologicals have a very narrow spectrum of activity. In addition, the continued use of certain chemical and biological control methods heightens the chance for insect pests to develop resistance to such control measures. This has been partially alleviated by various resistance management practices, but there remains a need to discover new and effective pest control agents that provide an economic benefit to farmers and that are environmentally acceptable. Particularly needed are control agents that are targeted to a wider spectrum of economically important insect pests and that efficiently control insect strains that are or could become resistant to existing insect control agents.

SUMMARY

In view of these needs, it is an object of the present invention to provide new pest control agents by providing novel genes and pesticidal proteins that may be used to control a variety of plant pests.

The invention provides compositions and methods for conferring pesticidal activity to bacteria, plants, plant cells, tissues and seeds. In particular, chimeric genes comprising novel polynucleotides that encode Cry proteins isolated from *Bacillus thuringiensis* (Bt) and sequences substantially identical thereto, whose expression results in proteins with toxicity to economically important insect pests, particularly insect pests that infest plants, are provided. The invention is further drawn to the novel Cry proteins resulting from the expression of the nucleic acid sequences, and to compositions and formulations containing the Cry proteins, which are toxic to insects by inhibiting the ability of insect pests to survive, grow and reproduce, or of limiting insect-related damage or loss to crop plants. Cry proteins of the invention include native Cry proteins and mutant Cry proteins that have one or more amino acid substitutions, additions or deletions. Examples of mutant Cry proteins includes without limitation those that are mutated to have a broader spectrum of activity than their native Cry protein counterparts or those mutated to introduce an epitope to generate antibodies that differentially recognize the mutated protein from the native protein. The novel Cry proteins of the invention are highly active against insect pests. For example, the Cry proteins of the invention can be used to control one or more economically important insects pests such as black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea* saccharalis), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like.

The invention also provides synthetic polynucleotides that encode the Cry proteins of the invention and have one or more codons optimized for expression in transgenic organisms such as bacteria and plants.

The invention is further drawn to expression cassettes and recombinant vectors comprising a polynucleotide that encodes a Cry protein of the invention. The invention also provides transformed bacteria, plants, plant cells, tissues, and seeds comprising a chimeric gene, or an expression cassette or a recombinant vector which comprise a polynucleotide encoding a Cry protein of the invention.

The invention is also drawn to methods of using the polynucleotides, for example in DNA constructs or chimeric genes or expression cassettes or recombinant vectors for transformation and expression in organisms, including microorganisms and plants. The nucleotide or amino acid sequences may be synthetic sequences that have been designed for expression in an organism including, but not limited to, a microorganism or a plant or in making hybrid toxins with enhanced pesticidal activity. The invention is further drawn to methods of making the Cry proteins and to methods of using the nucleic acid sequences, for example in microorganisms to control insects or in transgenic plants to confer protection from insect damage, and to methods of using the Cry proteins, and compositions and formulations comprising the Cry proteins, for example applying the Cry proteins or compositions or formulations to insect-infested areas, or to prophylactically treat insect-susceptible areas or plants to confer protection against the insect pests. The nucleotide or amino acid sequences may be synthetic sequences that have been designed for expression in an organism including, but not limited to, a microorganism or a plant.

The compositions and methods of the invention are useful for the production of organisms that are toxic to insects, specifically bacteria and plants. These organisms and compositions derived from them are desirable for agricultural purposes. The compositions of the invention are also useful for generating altered or improved Cry proteins that have pesticidal activity, or for detecting the presence of Cry protein or nucleic acids in products or organisms.

These and other features, aspects, and advantages of the invention will become better understood with reference to the following detailed description and claims.

BRIEF DESCRIPTION OF THE SEQUENCES IN THE SEQUENCE LISTING

SEQ ID NO: 1 represents a nucleotide sequence encoding a BT-0009 protein.

SEQ ID NO: 2 represents a nucleotide sequence encoding a BT-0012 protein.

SEQ ID NO: 3 represents a nucleotide sequence encoding a BT-0013 protein.

SEQ ID NO: 4 represents a nucleotide sequence encoding a BT-0023 protein.

SEQ ID NO: 5 represents a nucleotide sequence encoding a BT-0067 protein.

SEQ ID NO:6 represents a codon optimized sequence encoding a BT-0009 protein.

SEQ ID NO: 7 represents a codon optimized sequence encoding a BT-0012 protein.

SEQ ID NO:8 represents a codon optimized sequence encoding a BT-0013 protein.

SEQ ID NO:9 represents a codon optimized sequence encoding a BT-0023 protein.

SEQ ID NO:10 represents a codon optimized sequence encoding a BT-0067 protein.

SEQ ID NO:11 represents a nucleotide sequence encoding a mutant BT-0009 protein.

SEQ ID NO:12 represents a nucleotide sequence encoding a mutant BT-0012 protein.

SEQ ID NO:13 represents a nucleotide sequence encoding a mutant BT-0013 protein.

SEQ ID NO:14 represents a nucleotide sequence encoding a mutant BT-0023 protein.

SEQ ID NO:15 represents a nucleotide sequence encoding a mutant BT-0067 protein

SEQ ID NO:16 represents an amino acid sequence of a BT-0009 protein.

SEQ ID NO:17 represents an amino acid sequence of a BT-0012 protein.

SEQ ID NO:18 represents an amino acid sequence of a BT-0013 protein.

SEQ ID NO:19 represents an amino acid sequence of a BT-0023 protein.

SEQ ID NO:20 represents an amino acid sequence of a BT-0067 protein.

SEQ ID NO:21 represents an amino acid sequence of a mutant BT-0009 protein.

SEQ ID NO:22 represents an amino acid sequence of a mutant BT-0012 protein.

SEQ ID NO:23 represents an amino acid sequence of a mutant BT-0013 protein.

SEQ ID NO:24 represents an amino acid sequence of a mutant BT-0023 protein

SEQ ID NO:25 represents an amino acid sequence of a mutant BT-0067 protein.

SEQ ID NOS:26-31 represent primers useful in the invention.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. It is also to be understood that the terminology used herein is for the purpose of describing particular embodiments only, and is not intended to limit the scope of the present invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

By "activity" of a toxic Cry protein of the invention is meant that the toxic protein functions as an orally active insect control agent, has a toxic effect, or is able to disrupt or deter insect feeding, which may or may not cause death of the insect. When a toxic protein of the invention is delivered to the insect, the result is typically death of the insect, or the insect does not feed upon the source that makes the toxic protein available to the insect.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, and/or reproduce, or to limit insect-related damage or loss in crop plants or to protect the yield potential of a crop when grown in the presence of insect pests. To "control" insects may or may not mean killing the insects, although it preferably means killing the insects.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant Cry proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO:16 is the reference sequence and is aligned with SEQ ID NO:17, the Ala150 of SEQ ID NO:17 "corresponds to" Ala163 of SEQ ID NO:16.

To "deliver" a composition or toxic protein means that the composition or toxic protein comes in contact with an insect, resulting in a toxic effect and control of the insect. The composition or toxic protein can be delivered in many recognized ways, e.g., orally by ingestion by the insect or by contact with the insect via transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

"Effective insect-controlling amount" means that concentration of toxic protein that inhibits, through a toxic effect, the ability of insects to survive, grow, feed and/or reproduce, or to limit insect-related damage or loss in crop plants or protects the yield potential of a crop when grown in the presence of insect pests. "Effective insect-controlling amount" may or may not mean killing the insects, although it preferably means killing the insects.

"Expression cassette" as used herein means a nucleic acid molecule capable of directing expression of at least one polynucleotide of interest in an appropriate host cell, comprising a promoter operably linked to the polynucleotide of interest which is linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit consisting of a polynucleotide that occupies a specific location on a chromosome or plasmid and that contains the genetic instruction for a particular characteristic or trait in an organism.

A "gut protease" is a protease naturally found in the digestive tract of an insect. This protease is usually involved in the digestion of ingested proteins.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Homologous recombination" is the exchange ("crossing over") of DNA fragments between two DNA molecules or chromatids of paired chromosomes in a region of identical polynucleotides. A "recombination event" is herein understood to mean a meiotic crossing-over.

A nucleic acid sequence is "isocoding" with a reference nucleic acid sequence when the nucleic acid sequence encodes a polypeptide having the same amino acid sequence as the polypeptide encoded by the reference nucleic acid sequence.

The term "isolated" nucleic acid molecule, polynucleotide or toxin is a nucleic acid molecule, polynucleotide or toxic protein that no longer exists in its natural environment. An isolated nucleic acid molecule, polynucleotide or toxin of the invention may exist in a purified form or may exist in a recombinant host such as in a transgenic bacterial cell or a transgenic plant.

A "nucleic acid molecule" is single- or double-stranded DNA or RNA that can be isolated from any source. In the context of the present invention, the nucleic acid molecule is preferably a segment of DNA.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a Cry protein of the invention to control a pest organism or an amount of a Cry protein that can control a pest organism as defined herein. Thus, a pesticidal Cry protein can kill or inhibit the ability of a pest organism (e.g., insect pest) to survive, grow, feed, and/or reproduce.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g. a plant, confers upon the organism a desired characteristic such as antibiotic resistance, virus resistance, insect resistance, disease resistance, or resistance to other pests, herbicide tolerance, improved nutritional value, improved performance in an industrial process, production of commercially valuable enzymes or metabolites or altered reproductive capability.

The term "promoter" refers to a polynucleotide, usually upstream (5') of its coding polynucleotide, which controls the expression of the coding polynucleotide by providing the recognition for RNA polymerase and other factors required for proper transcription.

A "protoplast" is an isolated plant cell without a cell wall or with only parts of the cell wall.

As used herein, the term "recombinant" refers to a form of nucleic acid (e.g. DNA or RNA) and/or protein and/or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, and/or a nucleic acid molecule that is artificially synthesized and comprises a polynucleotide that deviates from the polynucleotide that would normally exist in nature, and/or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA and/or protein molecule in that organism. As used herein, a "recombinant plant" is a plant that would not normally exist in nature, is the result of human intervention, and contains a transgene and/or heterologous nucleic acid molecule incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

The term "identical" or "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1× SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising bases and/or structural features that are not present in the natural sequence. For example, an artificial sequence encoding a Cry protein of the invention that resembles more closely the G+C content and the normal codon distribution of dicot and/or monocot plant genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

This invention provides compositions and methods for controlling harmful plant pests. Particularly, the invention relates to Cry proteins that are toxic to plant pests and to polynucleotides that comprise nucleotide sequences that encode the Cry proteins, and to the making and using of the polynucleotides and Cry proteins to control plant pests.

Accordingly, in some embodiments, a chimeric gene is provided that comprises a heterologous promoter operably linked to a polynucleotide comprising a nucleotide sequence that encodes a protein toxic to at least European corn borer (*Ostrinia nubilalis*), wherein the nucleotide sequence (a) has at least 80% (e.g. 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:1-5; or (b) encodes a protein comprising an amino acid sequence that has at least 80% (e.g. 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:16-20; or (c) is a synthetic sequence of (a) or (b) that has codons optimized for expression in a transgenic organism.

In other embodiments, the heterologous promoter is a plant-expressible promoter. For example, without limitation, the plant-expressible promoter can be selected from the group consisting of ubiquitin, cmp, corn TrpA, bacteriophage T3 gene 9 5' UTR, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, *petunia* chalcone isomerase, bean glycine rich protein 1, Potato patatin, lectin, CaMV 35S, and the S-E9 small subunit RuBP carboxylase promoter.

In additional embodiments, the protein encoded by the chimeric gene is additionally toxic to one or more insect species selected from the group consisting of black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In further embodiments, the polynucleotide comprises a nucleotide sequence that has at least 80% to at least 99% sequence identity with SEQ ID NO:1, or has at least 80% to at least 99% sequence identity with SEQ ID NO:2, or has at least 80% to at least 99% sequence identity with SEQ ID NO:3, or has at least 80% to at least 99% sequence identity with SEQ ID NO:4, or has at least 80% to at least 99% sequence identity with SEQ ID NO:5.

In other embodiments, the polynucleotide comprises a nucleotide sequence that encodes a protein comprising an amino acid sequence that has at least 80% to at least 99% sequence identity with any one of SEQ ID NOS:16-20.

In still other embodiments, the amino acid sequence has at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:16.

In further embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:17.

In still further embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:18.

In other embodiments, the amino acid sequence has at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:19.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:20.

In some embodiments, the chimeric gene of the invention comprises a polynucleotide comprising a synthetic sequence of a nucleotide sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% with any of SEQ ID NOS:6-15, wherein the synthetic sequence has codons optimized for expression is a transgenic organism. In other embodiments, the chimeric gene of the invention comprises a polynucleotide comprising a synthetic sequence of a nucleotide sequence that encodes a protein comprising an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOS:16-25, wherein the synthetic sequence has codons optimized for expression is a transgenic organism. In further embodiments, the transgenic organism is a transgenic bacteria or a transgenic plant.

In some embodiments, the invention provides a synthetic polynucleotide comprising, consisting essentially of or consisting of a nucleotide sequence that encodes a protein that is active against at least European corn borer (*Ostrinia nubilalis*), wherein the nucleotide sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:6-15.

In other embodiments, the invention provides a synthetic polynucleotide comprising, consisting essentially of or consisting of a nucleotide sequence that encodes a protein that is active against at least European corn borer (*Ostrinia nubilalis*), wherein the nucleotide sequence encodes an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:16-25.

According to some embodiments, the invention provides an isolated protein that is toxic to at least European corn borer (*Ostrinia nubilalis*), wherein the protein comprises, consists essentially of or consists of (a) an amino acid sequence that has at least 80% sequence identity to at least 99% sequence identity with an amino acid sequence represented by any one of SEQ ID NOs:16-25 or (b) an amino acid sequence that is encoded by a nucleotide sequence that has at least 80% sequence identity to at least 99% sequence identity with a nucleotide sequence represented by any one of SEQ ID NOs:6-15.

In other embodiments, the isolated protein comprises, consists essentially of or consists of an amino acid sequence that has at least 80% to at least 99% sequence identity with any one of SEQ ID NOS:16-20. In still other embodiments, the amino acid sequence has at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:16.

In other embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:17.

In further embodiments, the amino acid sequence has at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:18.

In still further embodiments, the amino acid sequence has at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:19.

In still other embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:20.

In some embodiments, the amino acid sequence comprises, consists essentially of or consists of any one of SEQ ID NOs:16-25.

Antibodies raised in response to immune challenge by a native or mutant BT-0009, BT-0012, BT-0013, BT-0023 and BT-0067 and the like or related proteins of the present invention may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988) and as in Goding (1986). The present invention encompasses insecticidal proteins that cross-react with antibodies raised against one or more of the insecticidal Cry proteins of the present invention.

The antibodies produced in the present invention are also useful in immunoassays for determining the amount or presence of a native or mutant BT-0009, BT-0012, BT-0013, BT-0023 and BT-0067 or related protein in a biological sample. Such assays are also useful in quality-controlled production of compositions containing one or more of the toxic proteins of the present invention or related toxic proteins. In addition, the antibodies can be used to assess the efficacy of recombinant production of one or more of the proteins of the present invention or a related protein, as well as for screening expression libraries for the presence of a nucleotide sequence encoding one or more of the proteins of the invention or related protein coding sequences. Antibodies are useful also as affinity ligands for purifying and/or isolating any one or more of the proteins of the present invention and related proteins. The proteins of the present invention and proteins containing related antigenic epitopes may be obtained by over expressing full or partial lengths of a sequence encoding all or part of a protein of the present invention or a related protein in a preferred host cell.

It is recognized that DNA sequences that encode a native Cry protein of the invention may be altered by various methods, and that these alterations may result in DNA sequences encoding proteins with amino acid sequences different than that encoded by a native Cry protein of the invention. This protein may be altered in various ways including amino acid substitutions, deletions, truncations, and insertions of one or more amino acids of any of SEQ ID NOs:13-16, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a native Cry protein can be prepared by mutations in a polynucleotide that encodes the protein. This may also be accomplished by one of several forms of mutagenesis and/or in directed evolution. In some aspects, the changes encoded in the amino acid sequence will not substantially affect the function of the protein. Such variants will possess the desired insecticidal activity. In one embodiment of the invention, nucleotide sequences represented by SEQ ID NOs: 1-5 are altered to introduce amino acid substitutions in the encoded protein. In some embodiments, the resulting mutant protein is encoded by a synthetic mutant polynucleotide comprising a nucleotide sequence represented by any one of SEQ ID NOs:11-15. In other embodiments, the mutant proteins comprise, consist essentially of or consist of an amino acid sequence represented by any one of SEQ ID NOs:21-25.

It is understood that the ability of an insecticidal protein to confer insecticidal activity may be improved by the use of such techniques upon the compositions of this invention. For example, one may express a Cry protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the Cry protein mutations in a non-mutagenic strain, and identify mutated genes with insecticidal activity, for example by performing an assay to test for insecticidal activity. Generally, the protein is mixed and used in feeding assays. See, for example Marrone et al. (1985) J. of Economic Entomology 78:290-293. Such assays can include contacting plants with one or more pests and determining the plant's ability to survive and/or cause the death of the pests. Examples of mutations that result in increased toxicity are found in Schnepf et al. (1998) Microbiol. Mol. Biol. Rev. 62:775-806.

Alternatively, alterations may be made to an amino acid sequence of the invention at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

A Cry protein of the invention can also be mutated to introduce an epitope to generate antibodies that recognize the mutated protein. Therefore, in some embodiments, the invention provides a mutated Cry protein, wherein an amino acid substitution in a native Cry protein produces a mutant Cry protein having an antigenic region that allows the mutant Cry protein to be distinguished from the native Cry protein in a protein detection assay.

In some embodiments, the invention provides a method of making an antibody that differentially recognizes a mutated Cry protein from the native Cry protein from which the mutated Cry protein is derived, the method comprising the steps of substituting amino acids in an antigenic loop of a native Cry protein and raising antibodies that specifically recognize the mutated antigenic loop in the mutated Cry protein and does not recognize the native Cry protein. In one embodiment, the antigenic loop is identified in non-conserved regions outside of domain I of the native Cry protein. In another embodiment, the antigenic loop is not a loop involved in the Cry protein's insect gut receptor recognition or involved in the protease activation of the Cry protein.

Variant nucleotide and amino acid sequences of the present invention also encompass sequences derived from mutagenic and recombinogenic procedures such as DNA shuffling. With such a procedure, one or more different toxic protein coding regions can be used to create a new toxic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

Domain swapping or shuffling is another mechanism for generating altered Cry proteins of the invention. Domains may be swapped between Cry proteins, resulting in hybrid or chimeric toxic proteins with improved pesticidal activity or target spectrum. Methods for generating recombinant proteins and testing them for pesticidal activity are well known in the art (see, for example, Naimov et al. (2001) Appl. Environ. Microbiol. 67:5328-5330; de Maagd et al. (1996) Appl. Environ. Microbiol. 62:1537-1543; Ge et al. (1991) J. Biol. Chem. 266:17954-17958; Schnepf et al. (1990) J. Biol. Chem. 265:20923-20930; Rang et al. 91999) Appl. Environ. Microbiol. 65:2918-2925).

In some embodiments, the invention provides a recombinant vector comprising a polynucleotide, a nucleic acid molecule, an expression cassette or a chimeric gene of the invention. In other embodiments, the vector is further defined as a plasmid, cosmid, phagemid, artificial chromosome, phage or viral vector. Certain vectors for use in transformation of plants and other organisms are known in the art.

Thus, some embodiments of the invention are directed to expression cassettes designed to express the polynucleotides and nucleic acid molecules of the invention. As used herein, "expression cassette" means a nucleic acid molecule having at least a control sequence operatively linked to a nucleotide sequence of interest. In this manner, for example, plant promoters operably linked to the nucleotide sequences to be expressed are provided in expression cassettes for expression in a plant, plant part and/or plant cell.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of this invention also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, termination signals, and polyadenylation signal sequences.

In some embodiments, an expression cassette of the invention also can include nucleotide sequences that encode other desired traits. Such nucleotide sequences can be stacked with any combination of nucleotide sequences to create plants, plant parts or plant cells having the desired phenotype. Stacked combinations can be created by any method including, but not limited to, cross breeding plants by any conventional methodology, or by genetic transformation (i.e. molecular stacking). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

The expression cassette also can include a coding sequence for one or more polypeptides for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1 Ac, Cry1B, Cry1C, Cry1D, Cry1 Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In one embodiment, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

In some embodiments, the invention provides a transgenic non-human host cell comprising a polynucleotide, a nucleic acid molecule, a chimeric gene, an expression cassette or a recombinant vector of the invention. The transgenic non-human host cell can include, but is not limited to, a plant cell, a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc,* or *Alcaligenes*. Thus, for example, as biological insect control agents, the Cry proteins of the invention can be produced by expression of the chimeric gene encoding the Cry proteins of the invention in a bacterial cell. For example, in one embodiment, a *Bacillus thuringiensis* cell comprising a chimeric gene of the invention is provided.

In further embodiments, the invention provides a plant cell that is a dicot plant cell or a monocot plant cell. In additional embodiments, the dicot plant cell is selected from the group consisting of a soybean cell, sunflower cell, tomato cell, cole crop cell, cotton cell, sugar beet cell and tobacco cell. In further embodiments, the monocot cell is selected from the group consisting of a barley cell, maize cell, oat cell, rice cell, sorghum cell, sugar cane cell and wheat cell. In some embodiments, the invention provides a plurality of dicot cells or monocot cells expressing a toxic protein of the invention encoded by a chimeric gene of the invention. In other embodiments the plurality of cells are juxtaposed to form an apoplast and are grown in natural sunlight.

In another embodiment of the invention, a toxic protein of the invention is expressed in a higher organism, for example, a plant. In this case, transgenic plants expressing effective amounts of the toxic protein protect themselves from plant pests such as insect pests. When the insect starts feeding on such a transgenic plant, it also ingests the expressed toxin. This can deter the insect from further biting into the plant tissue or may even harm or kill the insect. A polynucleotide of the invention is inserted into an expression cassette, which is then stably integrated in the genome of the plant. In another embodiment, the polynucleotide is included in a non-pathogenic self-replicating virus. Plants transformed in accordance with the invention may be monocots or dicots and include, but are not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, *papaya*, mango, banana, and specialty plants, such as *Arabidopsis*, and woody plants such as coniferous and deciduous trees. Preferably, plants of the of the invention are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using traditional breeding techniques.

A polynucleotide of the invention is expressed in transgenic plants, thus causing the biosynthesis of the corresponding Cry protein in the transgenic plants. In this way, transgenic plants with enhanced yield protection in the presence of insect pressure are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, high expression in plants, for example corn plants, is best achieved from coding sequences that have at least about 35% GC content, or at least about 45%, or at least about 50%, or at least about 60%. Microbial nucleotide sequences that have low GC contents may express poorly in plants due to the existence of ATTTA motifs that may destabilize messages, and AATAAA motifs that may cause inappropriate polyadenylation. Although certain gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described for example in U.S. Pat. Nos. 5,625,136; 5,500,365 and 6,013,523.

In some embodiments, the invention provides synthetic genes made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are represented by any one of SEQ ID NOs: 6-15. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part synthetic optimized sequence.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

The novel cry protein coding sequences of the invention, either as their native sequence or as synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Examples of constitutive promoters useful in the invention include the CaMV 35S and 19S promoters (Fraley et al., U.S. Pat. No. 5,352,605, incorporated herein by reference). Additionally, a promoter is derived from any one of several of the actin genes, which are expressed in most cell types. The promoter expression cassettes described by McElroy et al. (Mol. Gen. Genet. 231: 150-160 (1991)) can be easily modified for the expression of the novel toxin gene and are particularly suitable for use in monocotyledonous hosts. Yet another constitutive promoter is derived from ubiquitin, which is another gene product known to accumulate in many cell types. A ubiquitin promoter has been cloned from several species for use in transgenic plants, for example, sunflower (Binet et al., 1991. Plant Science 79: 87-94), maize (Christensen et al., 1989. Plant Molec. Biol. 12: 619-632), and *arabidopsis* (Norris et al. 1993. Plant Molec. Biol. 21:895-906). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel cry protein coding sequences of the invention in plants, particularly maize, are those that direct expression in root, pith, leaf or pollen. Such promoters are disclosed in U.S. Pat. No. 5,625,136, herein incorporated by reference in its entirety. Other tissue specific promoters useful in the present invention include the cotton rubisco promoter disclosed in U.S. Pat. No. 6,040,504; the rice sucrose synthase promoter disclosed in U.S. Pat. No. 5,604,121; and the cestrum yellow leaf curling virus promoter disclosed in U.S. Pat. No. 7,166,770, all incorporated by reference in their entirety. Chemically inducible promoters useful for directing the expression of the novel toxin gene in plants are disclosed in U.S. Pat. No. 5,614,395 herein incorporated by reference in its entirety.

The nucleotide sequences of this invention can also be expressed under the regulation of promoters that are chemically regulated. This enables the Cry proteins of the invention to be synthesized only when the crop plants are treated with the inducing chemicals. Examples of such technology for chemical induction of gene expression is detailed in the published application EP 0 332 104 and U.S. Pat. No. 5,614,395. In one embodiment, the chemically regulated promoter is the tobacco PR-la promoter.

Another category of promoters useful in the invention is that which is wound inducible. Numerous promoters have been described which are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Non-limiting examples of promoters that cause tissue specific expression patterns that are useful in the invention include green tissue specific, root specific, stem specific, and/or flower specific. Promoters suitable for expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition to the selection of a suitable promoter, constructs for expression of an insecticidal toxin in plants require an appropriate transcription terminator to be operably linked downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Plant Transformation

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or glufosinate). However, the choice of selectable marker is not critical to the invention.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In another embodiment, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Nati. Acad. Sci. USA* 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransf erase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells and/or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is well known in the art, intact transgenic plants can be regenerated from transformed plant cells, plant tissue culture and/or cultured protoplasts using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic seeds and plants, plant parts, and/or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part and/or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Additional embodiments of the invention include harvested products produced from the transgenic plants and/or parts thereof of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention, wherein said seed or other plant part comprises a nucleic acid molecule/polynucleotide/nucleotide sequence of this invention.

In other embodiments, the invention provides an extract from a transgenic seed and/or a transgenic plant of the invention, wherein the extract comprises a nucleic acid molecule, a polynucleotide, a nucleotide sequence or a toxic protein of the invention. Extracts from plants or plant parts can be made according to procedures well known in the art (See, de la Torre et al., *Food, Agric. Environ.* 2(1):84-89 (2004); Guidet, *Nucleic Acids Res.* 22(9): 1772-1773 (1994); Lipton et al., *Food Agric. Immun.* 12:153-164 (2000)).

Insecticidal Compositions

In some embodiments, the invention provides an insecticidal composition comprising a Cry protein of the invention in an agriculturally acceptable carrier. As used herein an "agriculturally-acceptable carrier" can include natural or synthetic, organic or inorganic material which is combined with the active component to facilitate its application to the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. Another agriculturally acceptable carrier may be a transgenic plant or plant part.

In further embodiments, the insecticidal composition comprises a transgenic bacterial cell of the invention, wherein the bacterial cell comprises a chimeric gene of the invention. For example, such an insecticidal composition can be prepared by desiccation, lyophilization, homogenization, extraction, filtration, centrifugation, sedimentation, or concentration of a culture of *Bacillus thuringiensis* cells comprising a polynucleotide of the invention. In additional embodiments, the composition comprises from about 1% to about 99% by weight of the Cry protein of the invention.

The Cry proteins of the invention can be used in combination with other pest control agents to increase pest target range or for the prevention and/or management of insect resistance. Therefore, in some embodiments, the invention provides a composition that controls one or more plant pests, wherein the composition comprises a first Cry protein of the invention and a second pest control agent different from the first Cry protein. In other embodiments, the composition is a formulation for topical application to a plant. In still other embodiments, the composition is a transgenic plant. In further embodiments, the composition is a combination of a formulation topically applied to a transgenic plant. In one embodiment, the formulation comprises the first Cry protein of the invention when the transgenic plant comprises the second pest control agent. In another embodiment, the formulation comprises the second pest control agent when the transgenic plant comprises the first Cry protein of the invention.

In some embodiments, the second pest control agent can be an agent selected from the group consisting of a chemical pesticide, a *Bacillus thuringiensis* (Bt) insecticidal protein, a Xenorhabdus insecticidal protein, a *Photorhabdus* insecticidal protein, a *Brevibacillus laterosporus* insecticidal protein, a *Bacillus sphaericus* insecticidal protein, a protease inhibitors (both serine and cysteine types), lectins, alpha-amylase, peroxidase and cholesterol oxidase.

In other embodiments, the second pest control agent is a chemical pesticide selected from the group consisting of pyrethroids, carbamates, neonicotinoids, neuronal sodium channel blockers, insecticidal macrocyclic lactones, .gamma.-aminobutyric acid (GABA) antagonists, insecticidal ureas and juvenile hormone mimics. In another embodiment, the chemical pesticide is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In another embodiment, the chemical pesticide is selected from the group consisting of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1 Cb, Cry1Da, Cry1Db, Cry1Dc, Cry1Dd, Cry1Ea, Cry1Eb, Cry1Fa, Cry1Fb, Cry1Ga, Cry1 Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Ga, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa.

In further embodiments, the second pest control agent is a Vip3 vegetative insecticidal protein selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3.

In still further embodiments, the first Cry protein of the invention and the second pest control agent are co-expressed in a transgenic plant. This co-expression of more than one pesticidal principle in the same transgenic plant can be achieved by genetically engineering a plant to contain and express all the genes necessary. Alternatively, a plant, Parent 1, can be genetically engineered for the expression of the Cry protein of the invention. A second plant, Parent 2, can be genetically engineered for the expression of the second pest control agent. By crossing Parent 1 with Parent 2, progeny plants are obtained which express all the genes introduced into Parents 1 and 2.

In additional embodiments, a method of producing a protein toxic to at least European corn borer (*Ostrinia nubilalis*) is provided, the method comprising: culturing a transgenic non-human host cell that comprises polynucleotide or a chimeric gene or nucleic acid molecule or a recombinant vector of the invention under conditions in which the host produces a protein toxic to at least European corn borer (*Ostrinia nubilalis*). In some embodiments, the transgenic non-human host cell is a plant cell. In one embodiment, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In other embodiments, the produced protein has insecticidal activity against at least one additional insect, wherein the additional insect is selected from the group consisting of black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) or rice leaffolder (*Cnaphalocrocis medinalis*), and any combination thereof.

In other embodiments, the chimeric gene comprises any of SEQ ID NOs:1-5. In still other embodiments, the produced protein comprises an amino acid sequence of any of SEQ ID NOs: 16-20.

In some embodiments, the chimeric gene comprises a nucleotide sequence that is codon optimized for expression in a plant. In other embodiments, the chimeric gene comprises any of SEQ ID NOs:6-15. In further embodiments, the produced protein comprises an amino acid sequence of any of SEQ ID NOs:16-25.

In further embodiments, the invention provides a method of producing a pest-resistant (e.g., an insect-resistant) transgenic plant, comprising: introducing into a plant a polynucleotide, a chimeric gene, a recombinant vector, an expression cassette or a nucleic acid molecule of the invention comprising a nucleotide sequence that encodes a Cry protein of the invention, wherein the nucleotide sequence is expressed in the plant, thereby conferring to the plant resistance to at least European corn borer, and producing a pest-resistant (e.g., an insect-resistant) transgenic plant. In some embodiments, a pest-resistant transgenic plant is resistant to at least black cutworm (*Agrotis ipsilon*) as compared to a control plant lacking the polynucleotide, chimeric gene, recombinant vector, expression cassette or nucleic acid molecule of the invention. In some embodiments, the introducing is achieved by transforming the plant. In other embodiments, the introducing is achieved by crossing a first plant comprising the chimeric gene, recombinant vector, expression cassette or nucleic acid molecule of the invention with a different second plant.

In some embodiments, a transgenic plant of the invention that is resistant to at least European corn borer (*Ostrinia nubilalis*) is further resistant to at one additional insect, wherein the additional insect includes, but is not limited to, black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) or rice leaffolder (*Cnaphalocrocis medinalis*), and any combination thereof.

In further embodiments, a method of controlling at least black cutworm (*Agrotis ipsilon*) insects is provided, the method comprising delivering to the insects an effective amount of a Cry protein of the invention. To be effective, the Cry protein is first orally ingested by the insect. However, the Cry protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; (5) via injection into the insect; or (6) any other art-recognized protein delivery system. Thus, any method of oral delivery to an insect can be used to deliver the toxic Cry proteins of the invention. In some particular embodiments, the Cry protein of the invention is delivered orally to an insect, wherein the insect ingests one or more parts of a transgenic plant.

In other embodiments, the Cry protein of the invention is delivered orally to an insect, wherein the insect ingests one or more parts of a plant sprayed with a composition comprising the Cry proteins of the invention. Delivering the compositions of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In some embodiments, the invention encompasses a method of providing a farmer with a means of controlling a lepidopteran insect pest, the method comprising supplying or selling to the farmer plant material such as a seed, the plant material comprising a polynucleotide, chimeric gene, expression cassette or a recombinant vector capable of expressing a Cry protein of the invention, as described above.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1. Identification of Active Bt Strains

*Bacillus thuringiensis* isolates were cultured from spores present in current collections and maintained on T3+penicillin agar plates. Each isolate was grown aerobically in 24 well deep blocks for about 10 days at 28° C. until sporulation, which was verified by staining with Coomasie blue/acetic acid and visualization with a microscope. After sporulation both the soluble and insoluble fractions were tested for activity against lepidopteran species of interest. Fractions were tested in a surface contamination bioassay, where the fractions were overlaid onto a multispecies artificial diet. Each isolate was screened against at least four lepidopteran species, including *Helicoverpa zea* (corn earworm), *Agrotis ipsilon* (black cutworm), *Ostrinia nubilalis* (European corn borer), and *Spodoptera frugiperda* (fall armyworm) with a sample size of 12 neonate larvae. The duration of each assay was about 7 days at room temperature; the plates were scored for mortality as well as larval growth inhibition. Observed mortality at an increase of 30% over the negative control was considered active. Based on the initial insect testing, strains C0588, C0633, C0680 and M0262 were selected for further analysis.

Example 2: Isolation and Sequencing of Bt Genes

Fosmid Genomic Library Construction:

For some Bt strains that were identified in Example 1, genes encoding the putatively active proteins were isolated using a fosmid library method described in Park et al. (FEMS Microbiol. Lett. 284:28-34 (2008). The fosmid library was constructed using a CopyControl™ Fosmid Library Production Kit (Epicentre, Madison, Wis.) according to the manufacturer's protocol. Briefly, purified DNA from each Bt strain (approximately 0.5 μg) was treated enzymatically to end repair the blunt ends, and was then ligated into the fosmid vector pCC1FOS (Epicentre). After in vitro packaging into lambda phages and infection of *Escherichia coli* (*E. coli*) EPI1300-T1®, the bacterial cells were plated on Luria-Bertani (LB) that contained 12.5 μg/ml chloramphenicol. The plates were incubated at about 37° C. for 24 h before the selection of colonies. Transfected *E. coli* colonies were transferred to 96-well plates that contained 150 μl of chloramphenicol-containing LB medium and were incubated at 37° C. for 24 h.

Colony Hybridization Screen:

A fosmid library was plated at a density of 300 cfu per 100×15 mm L-agar plus 15 μg/ml chloramphenicol plate. A total of 3000 fosmids were plated. The filter hybridizations were performed using Immobilon-Ny+87 mm filter circles (EMD Millipore, Billerica, Mass.). Colony lifts were completed as follows: filters were placed on plates for about 5 min, then using forceps, filters were lifted from the agar surface and placed colony side up on Whatman filter paper soaked with 0.5 M NaOH for 5 min. Colony filters were then placed on Whatman filter paper soaked in 2×SSC for 5 min. DNA was immobilized to the membrane with a UV Stratalinker® set at 2000×100 μJ (Stratagene, Inc., La Jolla, Calif.). The filters are then air dried on Whatman filter paper. Filters were pre-hybridized and hybridized in 250 mM NaPO4, pH 7.0, 7% SDS, 1% BSA at 65° C. as described by the supplier. Hybridization filters were washed in 2×SSC, 0.5% SDS for 30 min at 65° C., followed by 0.2×SSC, 0.2% SDS for 30 min at 65° C. Filters were exposed to X-ray film (Kodak® BIOMAX® XAR, Fisher Scientific, Pittsburgh, Pa.) overnight with intensifying screens at −80° C. Positive colonies were patched to L agar with plus 15 μg/ml chloramphenicol.

Hybridization Probes:

PCR primers were designed to amplify a 720 bp fragment of a cry9B-like gene from the genomic DNA of a Bt strain designated C0633. The primer pair included a forward primer designated OAR2613a having the sequence AAACATGAACCGAAATAATCAAAATG (SEQ ID NO:26) and a reverse primer designated OAR2615a having the sequence ATCCGTCCCTTGTGCGTGTAAA (SEQ ID NO:27). The PCR reaction was run under the following cycle conditions: [94° C., 5 min], 12×[94° C., 30 sec, 57° C. to 51° C., dropping 0.5° C. per cycle, 30 sec, 72° C. 2.5 min], and 35×[94° C., 30 sec, 52° C., 30 sec, 72° C., 2.5 min]. The reaction contained 1× One Taq® buffer (New England Biolabs, Beverly, Mass.), 200 um dNTP, 80 ng DNA, 2.5U One Taq® DNA polymerase, 50 ng each primer and sterile distilled water to 50 μl total reaction.

The resulting amplicon was separated on 1% agarose TAE gel containing ethidium bromide. The amplicon was viewed under UV light and cut out of the gel. The DNA was isolated using a gel extraction kit as described by the supplier (Qiagen, Valencia, Calif.). Probes were labeled with EasyTide (α-32P) dCTP 3000 Ci/mmol (Perkin Elmer, Waltham, Mass.) using Rediprime II random prime labeling system (GE Healthcare, Pittsburgh, Pa.). Unincorporated nucleotides were removed using Micro Bio-Spin 30 Chromatography columns (Biorad, Hercules, Calif.). Probes were heated at 95° C. for 5 min before addition to hybridization solution.

Bt Gene Sequencing:

DNA preps for 2-4 independent clones are prepped following the manufacturer's instructions (Qiagen). Sequencing reactions with primers designed to both strands of the predicted nucleotide sequence of interest were carried out using the BigDye™ Terminator Kit (Applied Biosystems, Foster City, Calif.) according to manufacturer's instructions. Reaction products were electrophoresed on ABI373 or ABI377 sequencing instruments. All sequencing data are analyzed using the Phred/Phrap/Consed software package (University of Washington) to an error ratio equal to or less than $10^{-4}$ at the consensus sequence level. The sequence was assembled with the program Sequencher™ (Version 4.7, Gene Codes Corp., Ann Arbor, Mich.). Each gene was sequenced to 4× coverage.

Example 3. Bt Gene Cloning and Synthesis

Cry9-specific primer pairs were designed to facilitate the identification and cloning of cry9-type genes. Primer pairs were designed to hybridize to a 5' end of a cry9-type gene with the addition of a PmeI restriction site and to a 3' end with the addition of an AscI restriction site. The primer pair used to amplify a 5' end included a forward primer having the sequence <u>GTTTAAAC</u>ATGAATCGAAATAATCAAAATG (SEQ ID NO:28) and a reverse primer having the sequence <u>GGCGCGCC</u>CTACTCTTGTGTTTCAATAAA (SEQ ID NO:29). The primer pair used to amplify a 3' end included a forward primer having the sequence <u>GTTTAAAC</u>ATGAATCAAAATAAACACGGA (SEQ ID NO:30) and a reverse primer having the sequence <u>GGCGCGCC</u>TTACTGTTGGGTTTCCATGAACT (SEQ ID NO:31). The inserted restriction sites are underlined in the respective primers. The PCR reactions were carried out using the following cycle conditions: [94° C., 5 min] and 30×[94° C., 30 sec, 45° C., 30 sec, 72° C., 3.5 min]. The reaction contained 1× OneTaq buffer, 200 um dNTP, 80 ng DNA, 2.5 U OneTaq DNA polymerase (New England Biolabs), 50 ng each primer and sterile distilled water to 50 μl total reaction.

The resulting amplicon was cloned into the TOPO pCR 4.0 vector as described by the supplier (Life Technologies). Isolated plasmid DNA was digested with PmeI and AscI as described by the supplier (New England Biolabs).

The PmeI/AscI fragment was cloned into a shuttle vector designated pCIB5634' designed for expression in both *E. coli* and *B. thuringiensis*. The pCIB5634' vector was digested with PmeI and AscI. The digested vector and the gene fragment were purified by running on a 1% agarose Tris Acetate EDTA buffer based gel. The fragments were cutout from the gel and cleaned up using the QIAGEN gel extraction kit as described by the supplier. The fragments were ligated together using a ligation kit from New England Biolabs as described by the supplier. The ligation reaction was transformed into TOP10 cells (Life Technologies) as described by the supplier and plated on L-agar containing 100 mg/ml ampicillin. Plasmid DNA was isolated from a single colony and the identified clone was sequenced again to 2× coverage to confirm the correct sequence.

Some Bt genes that were selected for recombinant production but were not directly cloned out of genomic DNA were submitted to third party vendors for whole gene synthesis. These synthesized Bt genes were sub-cloned into the above-described shuttle vectors for subsequent expression and testing for further biological activity.

Example 4. Genome Assembly and Analysis

Some Bt genes of the invention were identified using a whole genome sequencing approach. Briefly, *Bacillus* DNA was sheared using a Covaris S2 ultrasonic device (Covaris, Inc., Woburn, Mass.) with the program DNA_400 bp set at duty cycle: 10%; intensity: 4; cycles/burst: 200. The DNA was treated with the NEBNext® Ultra™ End Repair/dA-tailing module (New England Biolabs, Inc. Ipswich, Mass.). Bioscience indexes 1-57 adapters (1-27 Brazil, 28-57 USA, UK and Switzerland) were ligated using NEB Quick Ligation™ as described by the supplier (New England Biolabs, Inc. Ipswich, Mass.). Ligations were cleaned up using Agencourt AMPure XP beads as described by the supplier (Beckman Coulter, Inc., Indianapolis, Ind.).

The library was size fractionated as follows: A 50 uL sample was mixed with 45 ul 75% bead mix (25% AMPure beads plus 75% NaCl/PEG solution TekNova cat #P4136). The mix was stirred and placed on magnetic rack. The resulting supernatant was transferred to a new well and 45 ul 50% bead mix (50% AMPure beads plus 50% NaCl/PEG solution TekNova cat #P4136) was added. This mix was stirred and placed on a magnetic rack. The resulting supernatant was removed and the beads were washed with 80% ethanol. 25 uL of elution buffer (EB) buffer was added and the mix placed on a magnetic rack. The final resulting supernatant was removed and placed in 1.5 mL tube. This method yielded libraries in the 525 DNA base pairs (bp) (insert plus adapter) size range.

The sized DNA library was amplified using KAPA Biosystem HiFi Hot Start (Kapa Biosystems, Inc., Wilmington, Mass.) using the following cycle conditions: [98° C., 45 s]; 12×[98° C., 15 s, 60° C., 30 s, 72° C., 30 s]; [72° C., 1 min]. Each reaction contained: 5 ul DNA library, 1 uL Bioscience universal primer (25 uM), 18 uL sterile water, 1 uL Bioscience indexed primer (25 uM), 25 ul 2×KAPA HiFi polymerase.

Libraries were run on the Agilent 2100 Bioanalyzer (Agilent Technologies, Santa Clara, Calif.) using High Sensitivity chips to determine the library size range and average insert size. All libraries were processed for paired end (PE) sequencing (100 cycles per read; 12-24 libraries per lane) on a HiSeq 2500 sequencing system using standard manufacturer's sequencing protocols (Illumina, Inc., San Diego, Calif.).

A *Bacillus* computational analysis tool was developed in order to identify and characterize likely toxin genes for prioritization of leads for further laboratory testing.

The genome assembly and analysis as well as the genomic library analysis described above led to the identification of five Cry9-like genes in the *Bacillus thuringiensis* strains with toxicity to at least European corn borer (*Ostrinia nubilalis*). Identifying characteristics of the Cry9-like genes and proteins are shown in Table 1.

TABLE 1

Cry9-like genes identified in *Bacillus thuringiensis* strains.

| Strain | Protein/Gene Name | Molecular Weight (kD) | Nucleotide SEQ ID NO: | Amino Acid SEQ ID NO: |
|---|---|---|---|---|
| C0588 | BT0009 | 132.2 | 1 | 16 |
| C0633 | BT0012 | 129.7 | 2 | 17 |
| C0633 | BT0013 | 129.6 | 3 | 18 |
| C0680 | BT0023 | 130.8 | 4 | 19 |
| M0262 | BT0067 | 130.3 | 5 | 20 |

Example 5. Homology of BT0009, BT0012, BT0013, BT0023 and BT0067 to Known Bt Cry Proteins A search of protein databases with the amino acid sequences of the proteins of the invention reveal that they are homologous to known insecticidal proteins. Comparison of the amino acid sequences of the proteins of the invention to the non-redundant (nr) database maintained by the NCBI using the BLAST algorithm revealed the following proteins as having the strongest block of amino acid identity to the sequences of the invention (Table 2).

TABLE 2

Percent identity of Cry proteins of the invention with known Cry proteins.

| | Percent Identity | | | | | | | |
|---|---|---|---|---|---|---|---|---|
| | Cry9Aa1 | Cry9Ba1 | Cry9Bb1 | Cry9Ca1 | Cry9Da1 | Cry9Db1 | Cry9Ea1 | CryFa1 | CryGa1 |
| 0009 | 60 | 70 | 66 | 66 | 82 | 88 | 67 | 64 | 36 |
| 0012 | 97 | 57 | 53 | 56 | 56 | 56 | 56 | 52 | 62 |
| 0013 | 97 | 57 | 53 | 56 | 56 | 56 | 56 | 52 | 62 |
| 0023 | 59 | 70 | 65 | 70 | 73 | 71 | 86 | 67 | 36 |
| 0067 | 59 | 69 | 66 | 75 | 76 | 74 | 76 | 69 | 36 |

Example 6. Bt Protein Expression in Recombinant Host Cells

*Bacillus* Expression. Genes of interest were expressed in an acrystalliferous *Bacillus* strain with no observable coleopteran or lepidopteran activity via the pCIB5634' expression vector described above, which contains an appropriate Cry protein promoter and erythromycin resistance marker. Constructs were transformed into the host strain via electroporation and subsequent selection on erythromycin containing agar plates. These recombinant strains were grown to sporulation phase in T3 media at 28° C. for 4-5 days. Cell pellets were harvested and washed iteratively before solubilization in high pH carbonate buffer (50 mM) containing 2 mM DTT.

E. coli Expression.

Genes of interest were expressed in various E. coli strains using the pET28a or pET29a vectors (EMD Millipore). Constructs were transformed by electroporation and subsequent selection on kanamycin-containing agar plates. These recombinant strains were grown and expression induced using IPTG induction at 28° C. Cells were resuspended in high pH carbonate buffer (50 mM) containing 2 mM DTT and then broken using a Microfluidics LV-1 homogenizer.

Expression Analysis.

Resulting cell lysates (from either host) were then clarified via centrifugation and samples were analyzed for purity via SDS-PAGE and electropherogram (BioRad Experion). Total protein concentrations were determined via Bradford or Thermo 660 assay. Purified Cry proteins were then tested in bioassays.

Example 7. Activity of Cry Proteins in Bioassays

The proteins produced in Example 6 were tested against one or more of the following insect pest species using an art-recognized artificial diet bioassay method: fall armyworm (FAW; *Spodoptera frugiperda*), corn earworm (CEW; *Helicoverpa zea*), European corn borer (ECB; *Ostrinia nubilalis*), black cutworm (BCW; *Agrotis ipsilon*), sugarcane borer (SCB; *Diatraea saccharlis*), velvet bean caterpillar (VBC; *Anticarsia gemmatalis*), soybean looper (SBL; *Pseudoplusia includens*), southwestern corn borer (SWCB; *Diatraea grandiosella*), western bean cutworm (WBCW; *Striacosta albicosta*), tobacco budworm (TBW; *Heliothis virescens*), Asian corn borer (ACB; *Ostrinia furnacalis*), cotton bollworm (CBW; *Helicoverpa armigera*), striped stem borer (SSB; *Chilo suppressalis*), pink stem borer (PSB; *Sesamia inferens*) and rice leaf folder (RLF; *Cnaphalocrocis medinails*).

An equal amount of protein in solution was applied to the surface of an artificial insect diet (Bioserv, Inc., Frenchtown, N.J.) in 24 well plates. After the diet surface dried, larvae of the insect species being tested were added to each well. The plates were sealed and maintained at ambient laboratory conditions with regard to temperature, lighting and relative humidity. A positive-control group consisted of larvae exposed to a very active and broad-spectrum wild-type *Bacillus* strain. Negative control groups consisted of larvae exposed to insect diet treated with only the buffer solution and larvea on untreated insect diet; i.e. diet alone. Mortality was assessed after about 120 hours and scored relative to the controls.

Results are shown in Table 3, where a "−" means no activity compared to check, a "+/−" means 0-10% activity compared to check (this category also includes 0% mortality with strong larval growth inhibition), a "+" means 10-25% activity compared to check, a "++" means 25-75% activity compared to check, and a "+++" 75-100% activity compared to check.

TABLE 3

Results of bioassay with Cry Proteins.

| Insect | BT Proteins | | | | |
|---|---|---|---|---|---|
| | 0009 | 0012 | 0013 | 0023 | 0067 |
| FAW | − | − | − | − | +/− |
| CEW | − | ++ | + | + | − |
| ECB | +++ | +++ | +++ | +++ | +++ |
| BCW | − | − | − | − | − |

TABLE 3-continued

Results of bioassay with Cry Proteins.

| Insect | BT Proteins | | | | |
|---|---|---|---|---|---|
| | 0009 | 0012 | 0013 | 0023 | 0067 |
| SCB | ++ | | | ++ | + |
| VBC | +++ | +++ | | | − |
| SBL | − | +++ | | | − |
| SWCB | ++ | | | +++ | +/− |
| WBCW | | | | | |
| TBW | | +++ | | | ++ |
| ACB | | | | | |
| CBW | | | | | |
| SSB | | | | | |
| PSB | | | | | |
| RLF | | | | | |

Example 8. Fate of Cry Proteins in Simulated Gastric Fluid Assay

Certain Cry proteins have been expressed in plants and seed from such plants are sold annually to farmers for use in controlling various insect pests. Such self-protected pesticidal products are subject to review and registration by various regulatory agencies including, for example, the US Environmental Protection Agency (EPA).

Dietary exposure is the major route by which humans can be exposed to Cry proteins expressed in transgenic plants. Acute oral mammalian toxicity and protein digestibility are the end points for EPA's human health risk assessment. Further scientific evidence of the safety of Cry proteins is that they have been shown to be rapidly degraded in vitro using simulated gastric fluids. Results of seven in vitro assays conducted with representative Cry1, Cry2, and Cry3 proteins establish that the proteins are rapidly degraded, typically within 30 seconds. These results support the broader conclusion that members of these groups of Cry proteins (that share significant amino acid sequence identity) are likely to be rapidly degraded following ingestion by humans. Another area of consideration is whether Cry proteins may induce an allergenic reaction. The demonstrated rapid in vitro degradation of Cry proteins should minimize the potential for such an occurrence. By comparison, food allergens generally persisted in the in vitro gastrointestinal model, whereas common food proteins with no allergenic history degraded rapidly in simulated gastric fluid (Metcalfe et al. 1996).

Additional insights into the potential allergenicity of a protein can be gained through an analysis of the protein's digestibility in simulated gastric fluid (SGF). Almost all Cry proteins expressed in transgenic plants that have been tested to date are rapidly digested and therefore have been determined to be non-allergenic. However, a Cry9C protein found in the transgenic corn product known as Starlink was found to be partially stable to SGF. Although Starlink Cry9C is not toxic to animals, the properties of partial digestibility and partial processing stability made it difficult for the EPA to absolutely preclude the possibility that the Starlink Cry9C protein could act a food allergen ultimately leading the company that developed Starlink to recall products from the US market.

Currently, no definitive tests for determining the allergenic potential of novel proteins exist. Therefore, EPA uses a weight-of-evidence approach where the following factors are considered: source of the trait; amino acid sequence comparison with known allergens; and biochemical properties of the protein, including in vitro digestibility in simulated gastric fluid (SGF) and glycosylation.

A simulated gastric fluid (SGF) assay measures the in vitro digestibility of a test protein at tightly controlled conditions representative of the upper mammalian digestive tract. In brief, bacterially produced test Cry protein (at a concentration of 0.5-5 mg/ml) was exposed to the enzyme pepsin (from porcine gastric mucosa, solubilized in 2 mg/ml NaCl, pH 1.2) at a ratio of 10 Units of pepsin activity/µg test protein over a time period of one hour at 37° C. Samples are removed at 1, 2, 5, 10, 30, and 60 minutes and immediately quenched with the addition of pre-heated (95° C.—2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin.

Results of the SGF assays demonstrated that all of the Cry proteins of the invention were degraded very rapidly. These results provide evidence that although the Cry proteins of the invention are related to the Cry9 protein family, they are quite different in their response to the SGF assay compared to certain published results, for example Cry9C in Starlink, suggesting significant structural differences at key pepsin cleavage sites in the protein. These results further suggest that the potential for the Cry proteins of the invention to be allergenic is minimal.

Example 9. Vectoring of Genes for Plant Expression

Prior to expression in plants, a synthetic polynucleotide comprising a nucleotide sequence encoding each of the Bt Cry proteins, BT-0009, BT-0012, BT-0013, BT-0023 and BT-0067 (SEQ ID NOs:16-20, respectively), and a synthetic polynucleotide comprising a nucleotide sequence encoding each of the mutant Bt Cry proteins, mBT-0009, mBT-0012, mBT-0013, mBT-0023 and mBT-0067 (SEQ ID NOs:21-25, respectively) was synthesized on an automated gene synthesis platform (Genscript, Inc., Piscataway, N.J.). For this example, a first expression cassette was made comprising a maize ubiquitin promoter (Ubi1) operably linked to the Cry protein coding sequence which was operably linked to a Nos terminator and a second expression cassette was made comprising a Ubi1 promoter operably linked to a phosphomannose isomerase (PMI) coding sequence which was operably linked to a Nos terminator. Expression of PMI allows for positive selection of transgenic plants on mannose. Both expression cassettes were cloned into a suitable vector for *Agrobacterium*-mediated maize transformation.

Example 11. Expression of Cry Proteins in Plants

Transformation of immature maize embryos is performed essentially as described in Negrotto et al., 2000, Plant Cell Reports 19: 798 803. Briefly, *Agrobacterium* strain LBA4404 (pSB1) comprising a vector described in Example 12 is grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* cells are suspended in LS-inf media supplemented with 100 μM As. Bacteria are pre-induced in this medium for approximately 30-60 minutes.

Immature embryos from an inbred maize line are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/1) and silver nitrate (1.6 mg/1) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the Bt cry gene by PCR. Positive plants from the PCR assay are transferred to a greenhouse for further evaluation.

Transgenic plants are evaluated for copy number (determined by Taqman analysis), protein expression level (determined by ELISA), and efficacy against insect species of interest in leaf excision bioassays. Specifically, leaf tissue is excised from single copy events (V3-V4 stage) and infested with neonate larvae, then incubated at room temperature for 5 days. Sample size for leaf disk bioassay varies depending on the insect species tested (European corn borer (ECB), n=10; corn earworm (CEW), n=3, black cutworm (BCW), n=5). Readings to assess tissue damage and mortality are taken at approximately day 3 and day 5; samples are rated for damage relative to the negative control using the following scale: "+": <5% tissue damage, all larvae dead; "+/−": 5-20% tissue damage, all larvae dead; or "−": >20% tissue damage, some larvae alive and/or progressing to $2^{nd}$ instar.

Results of the transgenic plant tissue bioassay confirm that the Cry proteins of the invention when expressed in transgenic plants are toxic to target insects. For example, mBT-0012 expressed in maize stably transformed with a chimeric gene of the invention is active against at least European corn borer (*Ostrinia nubilalis*).

What is claimed is:

1. A chimeric gene comprising a heterologous promoter operably linked to a nucleic acid molecule comprising a nucleotide sequence that encodes a protein toxic to at least European corn borer (*Ostrinia nubilalis*), wherein the nucleotide sequence (a) comprises SEQ ID NO:1; or (b) encodes a protein comprising an amino acid sequence that has at least 95% sequence identity across its full length with SEQ ID NO:21; or (c) is a synthetic sequence of (a) or (b) that has codons optimized for expression in a transgenic organism.

2. The chimeric gene of claim 1, wherein the nucleotide sequence comprises SEQ ID NO:1.

3. The chimeric gene of claim 1, wherein the nucleotide sequence encodes a protein comprising SEQ ID NO:16 or SEQ ID NO:21.

4. A synthetic nucleic acid molecule comprising a nucleotide sequence that encodes a protein that is toxic to at least European corn borer (*Ostrinia nubilalis*), wherein the nucleotide sequence has codons optimized for expression in a transgenic organism compared to SEQ ID NO:1 and encodes an amino acid sequence that has at least 95% sequence identity across its full length with SEQ ID NO:21.

5. A mutant insecticidal protein that is toxic to at least European corn borer (*Ostrinia nubilalis*), wherein the protein comprises an amino acid sequence that has at least 95% sequence identity across its full length to SEQ ID NO:21 and has one or more amino acid substitutions compared to SEQ ID NO:16.

6. The protein of claim 5, wherein the amino acid sequence comprises SEQ ID NO:21.

7. An insecticidal composition comprising the protein of claim 5 and an agriculturally acceptable carrier.

8. A recombinant vector comprising the chimeric gene of claim 1.

9. A transgenic plant comprising the chimeric gene of claim 1.

10. Transgenic seed of the transgenic plant of claim 9, wherein said seed comprises the chimeric gene.

11. A harvested product derived from the transgenic plant of claim 9, wherein the harvested product comprises the protein.

12. A processed product derived from the harvested product of claim 11, wherein the processed product is selected from the group consisting of flour, meal, oil, and wherein the processed product comprises the protein.

13. An extract from the transgenic plant of claim 9, wherein the extract comprises the chimeric gene or the protein.

14. A method of producing an insect-resistant transgenic plant, said method comprising: introducing into a plant the chimeric gene of claim 1, wherein the insecticidal protein is expressed in the plant, thereby conferring to the plant resistance to at least European corn borer (*Ostrinia nubilalis*), and producing an insect-resistant transgenic plant.

15. A method of controlling at least European corn borer (*Ostrinia nubilalis*) insects, said method comprising delivering to the insects an effective amount of a protein encoded by the chimeric gene of claim 1.

16. The synthetic nucleic acid molecule of claim 4, wherein the nucleotide sequence comprises SEQ ID NO:11.

17. The synthetic nucleic acid molecule of claim 4, wherein the nucleotide sequence encodes SEQ ID NO:16 or SEQ ID NO:21.

\* \* \* \* \*